(12) United States Patent
Jo et al.

(10) Patent No.: US 6,552,068 B1
(45) Date of Patent: Apr. 22, 2003

(54) 3-ETHYL-, 3-PROPYL- OR 3-BUTYL-CHROMAN AND THIOCHROMAN DERIVATIVES

(75) Inventors: JaeChon Jo, Seoul (KR); JongMin Kim, Kyonggi-do (KR); SungOh Ahn, Seoul (KR); JaeYoung Choi, Seoul (KR); Kazumi Morikawa, Shizuoka (JP); Yoshitake Kanbe, Shizuoka (JP); Masahiro Nishimoto, Shizuoka (JP); MyungHwa Kim, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/149,749
(22) PCT Filed: Dec. 13, 2000
(86) PCT No.: PCT/JP00/08809
§ 371 (c)(1), (2), (4) Date: Jun. 13, 2002
(87) PCT Pub. No.: WO01/42235
PCT Pub. Date: Jun. 14, 2001

(30) Foreign Application Priority Data

Dec. 13, 1999 (JP) .......................... 11-353592

(51) Int. Cl.[7] .................... A61K 31/38; A61K 31/35; C07D 335/04; C07D 311/04
(52) U.S. Cl. ................. 514/432; 514/456; 549/23; 549/406
(58) Field of Search ............. 549/23, 406; 514/432, 514/456

(56) References Cited

U.S. PATENT DOCUMENTS 6,156,788 A * 12/2000 Bernardon
6,218,427 B1 * 5/2001 Ishizuka et al.
6,316,494 B1 * 11/2001 Jacobsen et al.
6,369,225 B1 * 5/2002 Vasudevan et al.
6,417,223 B1 * 7/2002 Sanders et al.

* cited by examiner

Primary Examiner—Deborah C. Lambkin
(74) Attorney, Agent, or Firm—Browdy and Neimark PLLC

(57) ABSTRACT

A compound having the following general formula (1):

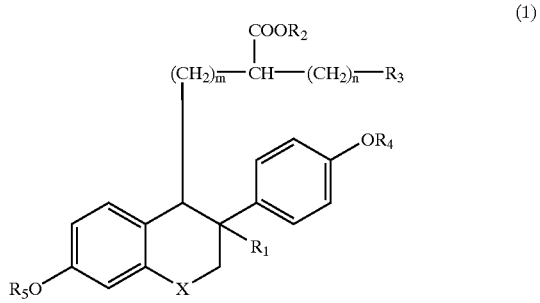

in which
- $R_1$ represents an ethyl group, etc.;
- $R_2$ represents a hydrogen atom, etc.;
- $R_3$ represents a $C_1$–$C_5$ perhalogenoalkyl group, etc.;
- each of $R_4$ and $R_5$ independently represents a hydrogen atom, etc.;
- X represents an oxygen atom or a sulfur atom;
- m represents an integer of 2 to 14; and
- n represents an integer of 2 to 7;

or an enantiomer of the compound, or a hydrate or a pharmaceutically acceptable salt of the compound or its enantiomer is advantageous in pharmaceutical use because of its anti-estrogenic activity.

20 Claims, No Drawings

3-ETHYL-, 3-PROPYL- OR 3-BUTYL-CHROMAN AND THIOCHROMAN DERIVATIVES

CROSS-REFERENCE TO RELATED APPLICATIONS

This application is a 371 of PCT/JP00/08809, filed Dec. 13, 2000, which claims priority from Japanses application 11-353592, filed Dec. 13, 1999.

TECHNICAL FIELD

The present invention relates to chroman or thiochroman derivatives having anti-estrogenic activity.

BACKGROUND ART

In treating diseases caused by abnormal tissue growth that is dependent upon a certain sexual steroidal hormone such as estrogen, it is highly important to significantly inhibit, more preferably completely eliminate, the effect induced by the hormone. For this purpose, it is desirable to reduce the level of hormone capable of acting on the steroidal hormone receptor site. For instance, anti-estrogenic agents are commonly administered for alternative or combination therapy to limit the production of estrogen to the amount less than required to activate the receptor site. However, such conventional technique for blocking estrogen production could not sufficiently inhibit the effect induced through the estrogen receptor. Practically, even when estrogen is completely absent, some of the receptors may be activated. It was therefore considered that estrogen antagonists could provide better therapeutic effect in comparison to the technique for blocking only the production of sexual steroidal hormone. Thus, numerous estrogen antagonists have been developed. For example, many patent publications including U.S. Pat. Nos. 4,760,061, 4,732,912, 4,904,661, 5,395,842 and WO 96/22092 disclose various anti-estrogenic compounds. Sometimes, however, prior art antagonists may themselves act as agonists, and therefore activate rather than block the receptor. For example, Tamoxifen has been most widely used as an anti-estrogenic agent. However, this agent has a disadvantage that it exhibits estrogenic activity in some organs (see, M. Harper and A. Walpole, J. Reprod. Fertile., 1967, 13, 101).

As another non-steroidal anti-estrogenic compound, WO 93/10741 discloses a benzopyran derivative having an aminoethoxyphenyl substituent(s) (Endorecherche), the typical compound of which is EM-343 having the following structure:

EM-343

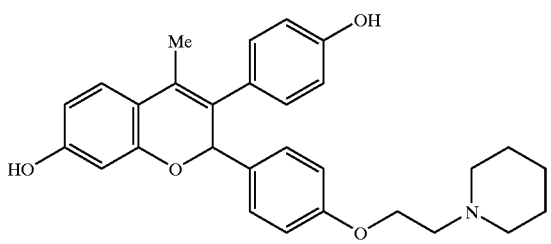

Said compound also has the agonistic effect. It is therefore required to develop an anti-estrogenic compound which is substantially or completely free of agonistic effect and which can effectively block the estrogen receptor.

In addition, it has been known that 7α-substituted derivatives of estradiol, for example, 7α-$(CH_2)_{10}$CONMeBu derivatives, are steroidal anti-estrogenic agents without agonistic effect (see, EP-A 0138504, U.S. Pat. No. 4,659,516). Further, an estradiol derivative having a 7α-$(CH_2)_9SOC_5H_6F_5$ substituent has also been disclosed (see, Wakeling et al., Cancer Res., 1991, 51, 3867).

Non-steroidal anti-estrogenic agents without agonistic effect have been first reported by Wakeling et al. in 1987 (see, A. Wakeling and Bowler, J. Endocrinol., 1987, 112, R7). Meanwhile, U.S. Pat. No. 4,904,661 discloses phenol derivatives having anti-estrogenic activity. These phenol derivatives generally have a naphthalene scaffold and include, typically, the following compounds:

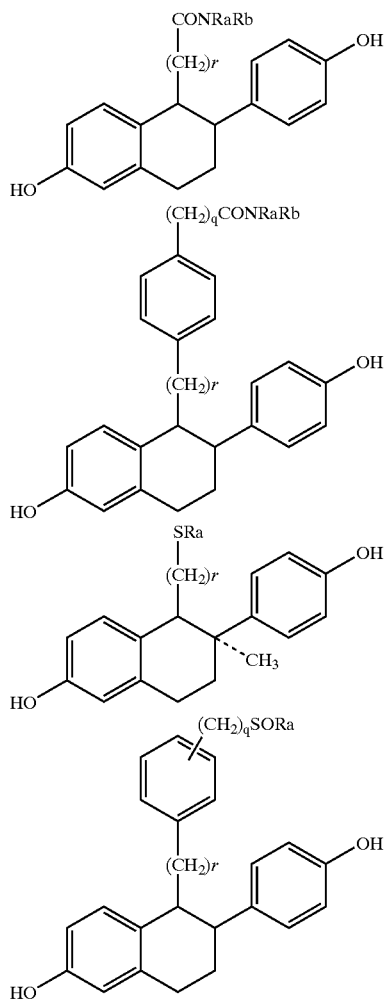

Some chroman and thiochroman derivatives have been reported as anti-estrogenic compounds having no agonistic effect (WO 98/25916). Although the existing anti-estrogenic compounds having no agonistic effect show a substantial therapeutic effect when administered via intravenous or subcutaneous injection, they show a highly reduced therapeutic effect when administered orally, probably due to their low bioavailability by oral route, etc. Therefore, for convenience's sake in the case of administration, it is desired to develop anti-estrogenic compounds which show a sufficient effect when administered orally and at the same time have no agonistic effect.

DISCLOSURE OF THE INVENTION

The object of the present invention is to provide chroman or thiochroman derivatives which have anti-estrogenic activity and are advantageous in pharmaceutical use.

The present inventors have researched anti-estrogenic activity of compounds having various structures. As a result, we have found that chroman and thiochroman derivatives of general formula (1) could show a good anti-estrogenic activity in substantial absence of agonistic effect and that they provided a sufficiently high activity even when administered orally. The present invention has been accomplished on the basis of this finding.

Namely, the present invention provides a compound having the following general formula (1):

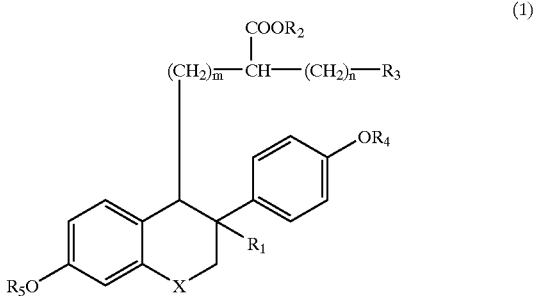

in which
 $R_1$ represents an ethyl group, a n-propyl group, an i-propyl group or a butyl group;
 $R_2$ represents a hydrogen atom or a salt-forming metal;
 $R_3$ represents a linear or branched $C_1$–$C_7$ halogenoalkyl group;
 each of $R_4$ and $R_5$ independently represents a hydrogen atom, an optionally substituted linear or branched $C_1$–$C_3$ alkyl group, an acyl group or a salt-forming metal;
 X represents an oxygen atom or a sulfur atom;
 m represents an integer of 2 to 14; and
 n represents an integer of 2 to 7;
or enantiomers of the compound, or hydrates or pharmaceutically acceptable salts of the compound or its enantiomers.

In addition, the present invention provides a pharmaceutical composition comprising a compound of general formula (1) as an active ingredient. Further, the present invention provides an anti-estrogenic pharmaceutical composition comprising the above compound as an active ingredient. The present invention also provides a therapeutic agent for breast cancer comprising the above compound as an active ingredient.

A butyl group as $R_1$ encompasses a n-butyl group, an i-butyl group, a s-butyl group and a t-butyl group, with a n-butyl group and an i-butyl group being preferred.

In the definition of a compound having general formula (1), $R_1$ may preferably be an ethyl group, a n-propyl group or a n-butyl group.

Salt-forming metals as $R_2$ include, but are not limited to, alkali metals such as sodium and potassium, alkaline earth metals such as magnesium and calcium, rare earth metals such as cerium and samarium, as well as zinc and tin. Among these, preferred are alkali metals and alkaline earth metals, particularly sodium, potassium and calcium.

$R_2$ may preferably be a hydrogen atom, an alkali metal or an alkaline earth metal.

Halogens in the linear or branched $C_1$–$C_7$ halogenoalkyl groups as $R_3$ include fluorine, chlorine, bromine and iodine, with fluorine being preferred. Alkyls in the linear or branched $C_1$–$C_7$ halogenoalkyl groups under consideration include, for example, methyl, ethyl, n-propyl, i-propyl, n-butyl, i-butyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl and n-heptyl. Preferred are linear or branched $C_1$–$C_5$ alkyls, more specifically linear or branched $C_2$–$C_4$ alkyls, i.e., ethyl, n-propyl, i-propyl and n-butyl. Particularly preferred are ethyl and n-butyl.

Examples of the linear or branched $C_1$–$C_7$ halogenoalkyl group as $R_3$ include the above-listed linear or branched $C_1$–$C_7$ alkyl groups, provided that they are halogenated, preferably perhalogenated, more preferably perfluorinated. Also preferred are perhalogenated linear or branched $C_1$–$C_5$ alkyl groups, particularly perhalogenated linear or branched $C_2$–$C_4$ alkyl groups, or a group of the following general formula (2):

in which each of $R_6$ and $R_7$ is a linear or branched $C_1$–$C_3$ perhalogenoalkyl group. Among them, perfluorinated groups are preferred. More specifically, a perfluoroethyl group, a perfluoro-n-propyl group and a perfluoro-n-butyl group are particularly preferred.

In the case where $R_3$ is a group of general formula (2), halogens in the linear or branched $C_1$–$C_3$ perhalogenoalkyl groups as $R_6$ and $R_7$ include fluorine, chlorine, bromine and iodine, with fluorine being preferred. Alkyls in the linear or branched $C_1$–$C_3$ perhalogenoalkyl groups under consideration include, methyl, ethyl, n-propyl and i-propyl, with methyl being preferred.

In the case where $R_3$ is a group of general formula (2), examples of the linear or branched $C_1$–$C_3$ perhalogenoalkyl group as $R_6$ and $R_7$ include the above-listed linear or branched $C_1$–$C_3$ alkyl groups, provided that they are perhalogenated, preferably perfluorinated. Further, perhalogenated $C_1$ alkyl groups are preferred and a perfluorinated group is particularly preferred. More specifically, a perfluoromethyl group is preferred.

A group of general formula (2) as $R_3$ is preferably a 1,1,1,3,3,3-hexafluoroisopropyl group.

Having the definition given above, $R_3$ is preferably a perfluoroethyl group, a perfluoro-n-propyl group, a perfluoro-n-butyl group or a 1,1,1,3,3,3-hexafluoroisopropyl group.

Alkyls in the optionally substituted linear or branched $C_1$–$C_3$ alkyl groups as $R_4$ and $R_5$ include, methyl, ethyl, n-propyl and i-propyl.

Substituents on the optionally substituted linear or branched $C_1$–$C_3$ alkyl groups as $R_4$ and $R_5$ include, an alkoxy group having a linear or branched $C_1$–$C_5$ alkyl as its alkyl moiety and a hydroxyl group, more specifically a methoxy group.

Examples of the optionally substituted linear or branched $C_1$–$C_3$ alkyl group as $R_4$ and $R_5$ include the above-listed alkyl groups, provided that they may be substituted with the above-listed substituents. Specific examples of the substituted alkyl group include a methoxymethyl group.

Examples of the acyl group as $R_4$ and $R_5$ include, an acetyl group, a benzoyl group and a pivaloyl group.

Salt-forming metals as $R_4$ and $R_5$ include, alkali metals such as sodium and potassium, alkaline earth metals such as magnesium and calcium, rare earth metals such as cerium and samarium, as well as zinc and tin. Among these, preferred are alkali metals and alkaline earth metals, particularly sodium, potassium and calcium.

Preferably, $R_4$ and $R_5$ are independently a hydrogen atom or a salt-forming metal. In a suitable combination of $R_2$, $R_4$ and $R_5$, at least one or all of them may be a hydrogen atom and the remainder may be a salt-forming metal. Examples of such combination include the following: a combination where $R_2$, $R_4$ and $R_5$ are each a hydrogen atom; a combination where $R_2$ is a salt-forming metal (e.g., an alkali metal such as sodium) and $R_4$ and $R_5$ are each a hydrogen atom; and a combination where $R_2$, $R_4$ and $R_5$ are each a salt-forming metal (e.g., an alkali metal such as sodium).

X may preferably be an oxygen atom or a sulfur atom.

m may preferably be an integer of 6 to 10, particularly 8 to 10, more particularly 8 or 9.

n may preferably be an integer of 2 to 6, particularly 2 to 5.

Compounds of general formula (1) have enantiomers. All individual enantiomers and mixtures thereof are intended to be within the scope of the present invention. Among the enantiomers, preferred are compounds where the configuration of 3- and 4-position chiral carbons in the parent scaffold (i.e., chroman or thiochroman ring) in general formula (1) is (3RS,4RS), (3R,4R) or (3S,4S). Also compounds having R- or S-configuration at the carbon to which the carboxylic acid is bonded, wherein said carbon is the carbon on the side chain which is bonded to 4-position of the parent scaffold (i.e., chroman or thiochroman ring) in general formula (1) and mixtures of such compounds at any ratio are preferable.

Among compounds of general formula (1), preferred are those compounds in which $R_1$ is an ethyl group, a n-propyl group or a n-butyl group; $R_2$ is a hydrogen atom, an alkali metal or an alkaline earth metal; $R_3$ is a perfluoroethyl group, a perfluoro-n-propyl group, a perfluoro-n-butyl group or a 1,1,1,3,3,3-hexafluoroisopropyl group; X is an oxygen atom or a sulfur atom; m is an integer of 8 or 9; and n is an integer of 2 to 6. Particularly preferred are compounds in which:

a) $R_1$ is an ethyl group; $R_2$ is a hydrogen atom, $R_3$ is a perfluoroethyl group, X is a sulfur atom, m is 8, and n is 3;

b) $R_1$ is an ethyl group, $R_2$ is a hydrogen atom, $R_3$ is a perfluoroethyl group, X is a sulfur atom, m is 8, and n is 4;

c) $R_1$ is an ethyl group, $R_2$ is a hydrogen atom, $R_3$ is a perfluoroethyl group, X is a sulfur atom, m is 8, and n is 5;

d) $R_1$ is an ethyl group, $R_2$ is a hydrogen atom, $R_3$ is a perfluorobutyl group, X is a sulfur atom, m is 8, and n is 2;

e) $R_1$ is an ethyl group, $R_2$ is a hydrogen atom, $R_3$ is a perfluoroethyl group, X is a sulfur atom, m is 9, and n is 3;

f) $R_1$ is an ethyl group, $R_2$ is a hydrogen atom, $R_3$ is a perfluorobutyl group, X is a sulfur atom, m is 9, and n is 2;

g) $R_1$ is a n-propyl group, $R_2$ is a hydrogen atom, $R_3$ is a perfluoroethyl group, X is a sulfur atom, m is 8, and n is 3;

h) $R_1$ is an ethyl group, $R_2$ is a hydrogen atom, $R_3$ is a perfluoroethyl group, X is an oxygen atom, m is 9, and n is 5;

i) $R_1$ is an ethyl group, $R_2$ is a hydrogen atom, $R_3$ is a perfluorobutyl group, X is an oxygen atom, m is 9, and n is 2;

j) $R_1$ is an ethyl group, $R_2$ is a hydrogen atom, $R_3$ is a perfluorobutyl group, X is an oxygen atom, m is 8, and n is 3;

k) $R_1$ is an ethyl group, $R_2$ is a hydrogen atom, $R_3$ is a perfluorobutyl group, X is an oxygen atom, m is 9, and n is 3;

l) $R_1$ is a n-propyl group, $R_2$ is a hydrogen atom, $R_3$ is a perfluoroethyl group, X is a sulfur atom, m is 8, and n is 4;

m) $R_1$ is a n-propyl group, $R_2$ is a hydrogen atom, $R_3$ is a perfluorobutyl group, X is a sulfur atom, m is 8, and n is 2;

n) $R_1$ is a n-propyl group, $R_2$ is a hydrogen atom, $R_3$ is a perfluoroethyl group, X is a sulfur atom, m is 9, and n is 3;

o) $R_1$ is a n-propyl group, $R_2$ is a hydrogen atom, $R_3$ is a perfluorobutyl group, X is a sulfur atom, m is 9, and n is 2;

p) $R_1$ is a n-propyl group, $R_2$ is a hydrogen atom, $R_3$ is a perfluoroethyl group, X is an oxygen atom, m is 8, and n is 4;

q) $R_1$ is a n-propyl group, $R_2$ is a hydrogen atom, $R_3$ is a perfluorobutyl group, X is an oxygen atom, m is 8, and n is 2;

s) $R_1$ is a n-propyl group, $R_2$ is a hydrogen atom, $R_3$ is a perfluorobutyl group, X is an oxygen atom, m is 8, and n is 3;

t) $R_1$ is a n-propyl group, $R_2$ is a hydrogen atom, $R_3$ is a perfluoroethyl group, X is an oxygen atom, m is 9, and n is 3;

u) $R_1$ is a n-propyl group, $R_2$ is a hydrogen atom, $R_3$ is a perfluoroethyl group, X is an oxygen atom, m is 9, and n is 4;

v) $R_1$ is a n-propyl group, $R_2$ is a hydrogen atom, $R_3$ is a perfluorobutyl group, X is an oxygen atom, m is 9, and n is 2;

w) $R_1$ is a n-propyl group, $R_2$ is a hydrogen atom, $R_3$ is a perfluorobutyl group, X is an oxygen atom, m is 9, and n is 3;

x) $R_1$ is a n-butyl group, $R_2$ is a hydrogen atom, $R_3$ is a perfluorobutyl group, X is an oxygen atom, m is 8, and n is 3; or y) $R_1$ is a n-propyl group, $R_2$ is a hydrogen atom, $R_3$ is a perfluorobutyl group, X is an oxygen atom, m is 8, and n is 3.

The compounds of the present invention may be obtained as hydrates.

As typical examples of these compounds, the following compounds can be mentioned:

10-[(3RS,4RS)-3-ethyl-7-hydroxy-3-(4-hydroxyphenyl)thiochroman-4-yl]-2-(4,4,5,5,5-pentafluoropentyl)decanoic acid;

10-[(3RS,4RS)-3-ethyl-7-hydroxy-3-(4-hydroxyphenyl)thiochroman-4-yl]-2-(5,5,6,6,6-pentafluorohexyl)decanoic acid;

10-[(3RS,4RS)-3-ethyl-7-hydroxy-3-(4-hydroxyphenyl)thiochroman-4-yl]-2-(6,6,7,7,7-pentafluoroheptyl)decanoic acid;

10-[(3RS,4RS)-3-ethyl-7-hydroxy-3-(4-hydroxyphenyl)thiochroman-4-yl]-2-(3,3,4,4,5,5,6,6,6-nonafluorohexyl)decanoic acid;

11-[(3RS,4RS)-3-ethyl-7-hydroxy-3-(4-hydroxyphenyl)thiochroman-4-yl]-2-(4,4,5,5,5-pentafluoropentyl)undecanoic acid;

11-[(3RS,4RS)-3-ethyl-7-hydroxy-3-(4-hydroxyphenyl)
thiochroman-4-yl]-2-(3,3,4,4,5,5,6,6,6-
nonafluorohexyl)undecanoic acid;

10-[(3RS,4RS)-7-hydroxy-3-(4-hydroxyphenyl)-3-
propylthiochroman-4-yl]-2-(4,4,5,5,5-
pentafluoropentyl)decanoic acid;

11-[(3RS,4RS)-3-ethyl-7-hydroxy-3-(4-hydroxyphenyl)
chroman-4-yl]-2-(6,6,7,7,7-pentafluoroheptyl)
undecanoic acid;

11-[(3RS,4RS)-3-ethyl-7-hydroxy-3-(4-hydroxyphenyl)
chroman-4-yl]-2-(3,3,4,4,5,5,6,6,6-nonafluorohexyl)
undecanoic acid;

10-[(3RS,4RS)-3-ethyl-7-hydroxy-3-(4-hydroxyphenyl)
chroman-4-yl]-2-(4,4,5,5,6,6,7,7,7-nonafluoroheptyl)
decanoic acid;

11-[(3RS,4RS)-3-ethyl-7-hydroxy-3-(4-hydroxyphenyl)
chroman-4-yl]-2-(4,4,5,5,6,6,7,7,7-nonafluoroheptyl)
undecanoic acid;

10-[(3RS,4RS)-7-hydroxy-3-(4-hydroxyphenyl)-3-
propylthiochroman-4-yl]-2-(5,5,6,6,6-
pentafluorohexyl)decanoic acid;

10-[(3RS,4RS)-7-hydroxy-3-(4-hydroxyphenyl)-3-
propylthiochroman-4-yl]-2-(3,3,4,4,5,5,6,6,6-
nonafluorohexyl)decanoic acid;

11-[(3RS,4RS)-7-hydroxy-3-(4-hydroxyphenyl)-3
-propylthiochroman-4-yl]-2-(4,4,5,5,5,-
pentafluoropentyl)undecanoic acid;

11-[(3RS,4RS)-7-hydroxy-3-(4-hydroxyphenyl)-3-
propylthiochroman-4-yl]-2-(3,3,4,4,5,5,6,6,6-
nonafluorohexyl)undecanoic acid;

10-[(3RS,4RS)-7-hydroxy-3-(4-hydroxyphenyl)-3-
propylchroman-4-yl]-2-(5,5,6,6,6-pentafluorohexyl)
decanoic acid;

10-[(3RS,4RS)-7-hydroxy-3-(4-hydroxyphenyl)-3-
propylchroman-4-yl]-2-(3,3,4,4,5,5,6,6,6-
nonafluorohexyl)decanoic acid;

10-[(3RS,4RS)-7-hydroxy-3-(4-hydroxyphenyl)-3-
propylchroman-4-yl]-2-(4,4,5,5,6,6,7,7,7-
nonafluoroheptyl)decanoic acid;

11-[(3RS,4RS)-7-hydroxy-3-(4-hydroxyphenyl)-3-
propylchroman-4-yl]-2-(4,4,5,5,5-pentafluoropentyl)
undecanoic acid;

11-[(3RS,4RS)-7-hydroxy-3-(4-hydroxyphenyl)-3-
propylchroman-4-yl]-2-(5,5,6,6,6-pentafluorohexyl)
undecanoic acid;

11-[(3RS,4RS)-7-hydroxy-3-(4-hydroxyphenyl)-3-
propylchroman-4-yl]-2-(3,3,4,4,5,5,6,6,6-
nonafluorohexyl)undecanoic acid;

11-[(3RS,4RS)-7-hydroxy-3-(4-hydroxyphenyl)-3-
propylchroman-4-yl]-2-(4,4,5,5,6,6,7,7,7-
nonafluoroheptyl)undecanoic acid;

10-[(3RS,4RS)-3-butyl-7-hydroxy-3-(4-hydroxyphenyl)
chroman-4-yl]-2-(4,4,5,5,6,6,7,7,7-nonafluoroheptyl)
decanoic acid;

10-[(3RS,4RS)-7-hydroxy-3-(4-hydroxyphenyl)-3-
propylthiochroman-4-yl]-2-(4,4,5,5,6,6,7,7,7-
nonafluoroheptyl)decanoic acid.

As an optically active compound of general formula (1) that has chiral carbons at positions 3 and 4 of the parent scaffold and at α-position to the carboxyl group of the side chain, each of the compounds represented by Peaks 1 and 2 in Examples 50 and 52 stated below is preferred.

Pharmaceutically acceptable salts include, the above-mentioned metal salts, for example, sodium, potassium and calcium salts. Such metal salts may be formed with a carboxyl group and/or a phenolic hydroxyl group in the compound of the present invention.

The compound of general formula (1) may be administered as a pharmaceutical composition in any dosage form suitable for the intended route of administration, in combination with one or more pharmaceutically acceptable diluents, wetting agents, emulsifiers, dispersants, auxiliary agents, preservatives, buffers, binders, stabilizers and the like. The compound and composition may be administered parenterally or orally.

The dose of the compound can be suitably determined according to the physique, age and physical condition of a patient, severity of the disease to be treated, elapsed time after onset of the disease, etc. For example, the compound is generally used in an amount of 0.1 to 500 mg/day when orally administered and in an amount of 1 to 1000 mg/month when parenterally administered (by intravenous, intramuscular, or subcutaneous route) for adult patient.

BEST MODE FOR CARRYING OUT THE INVENTION

The compound of general formula (1) can be prepared according to any one of the following Reaction Schemes 1 to 10 (Processes 1 to 10).

Reaction Scheme 1

(Process 1)

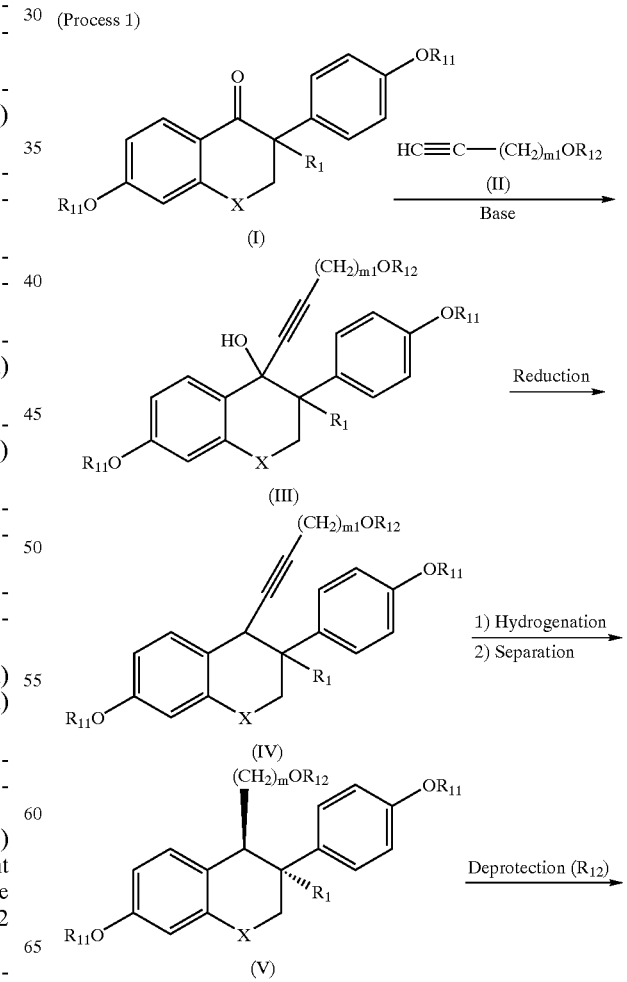

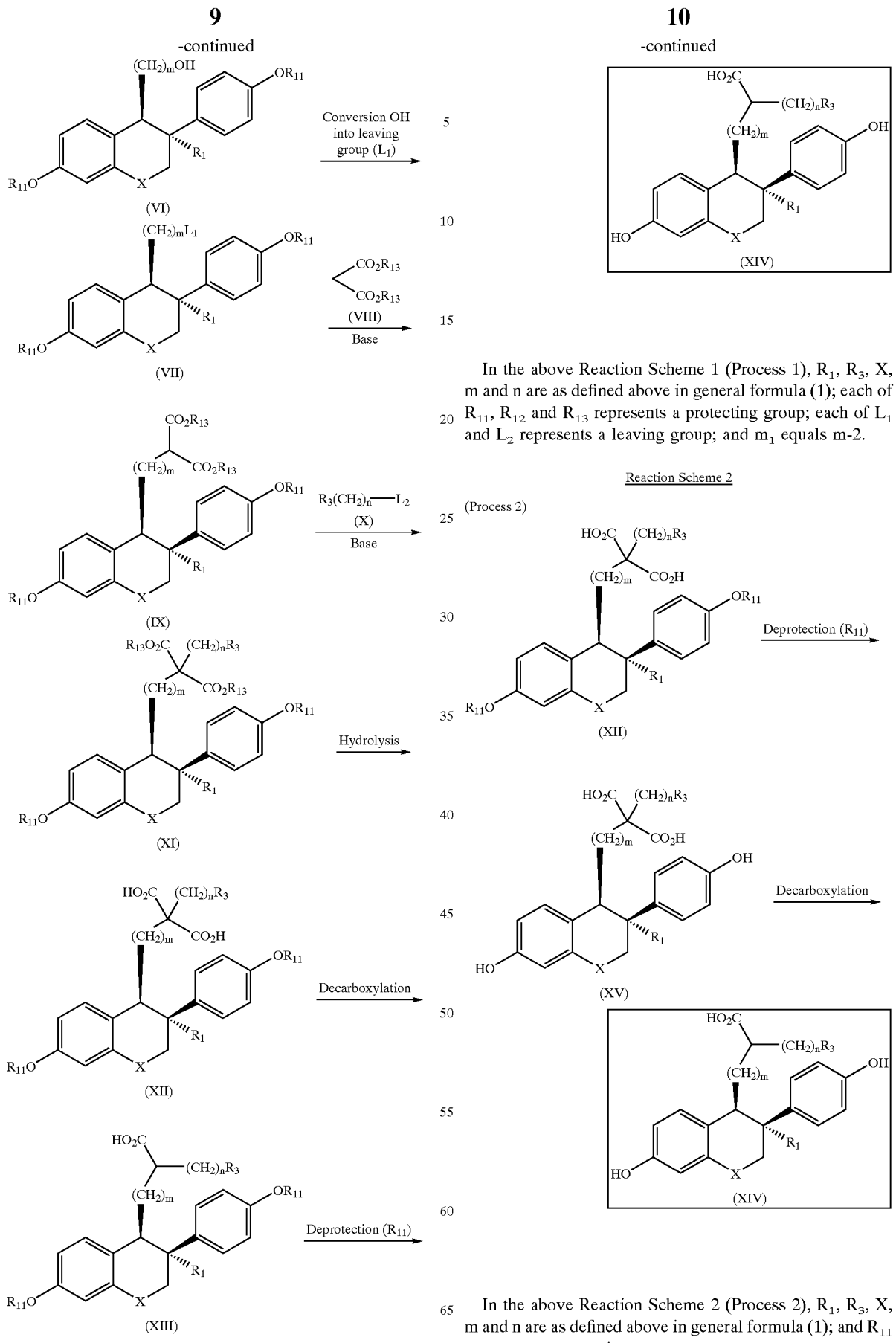
In the above Reaction Scheme 1 (Process 1), $R_1$, $R_3$, X, m and n are as defined above in general formula (1); each of $R_{11}$, $R_{12}$ and $R_{13}$ represents a protecting group; each of $L_1$ and $L_2$ represents a leaving group; and $m_1$ equals m-2.
In the above Reaction Scheme 2 (Process 2), $R_1$, $R_3$, X, m and n are as defined above in general formula (1); and $R_{11}$ represents a protecting group.

Reaction Scheme 3

(Process 3)

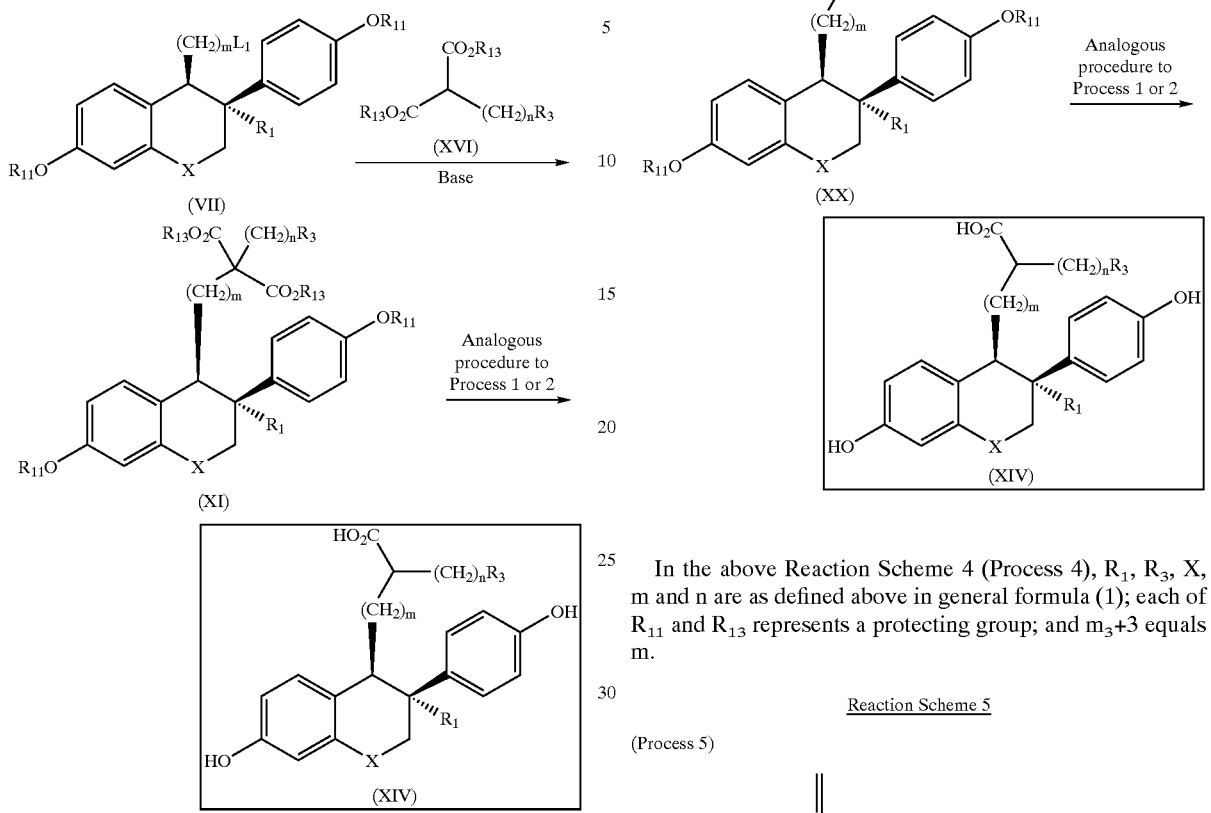

In the above Reaction Scheme 3 (Process 3), $R_1$, $R_3$, X, m and n are as defined above in general formula (1); each of $R_{11}$ and $R_{13}$ represents a protecting group; and $L_1$ represents a leaving group.

Reaction Scheme 4

(Process 4)

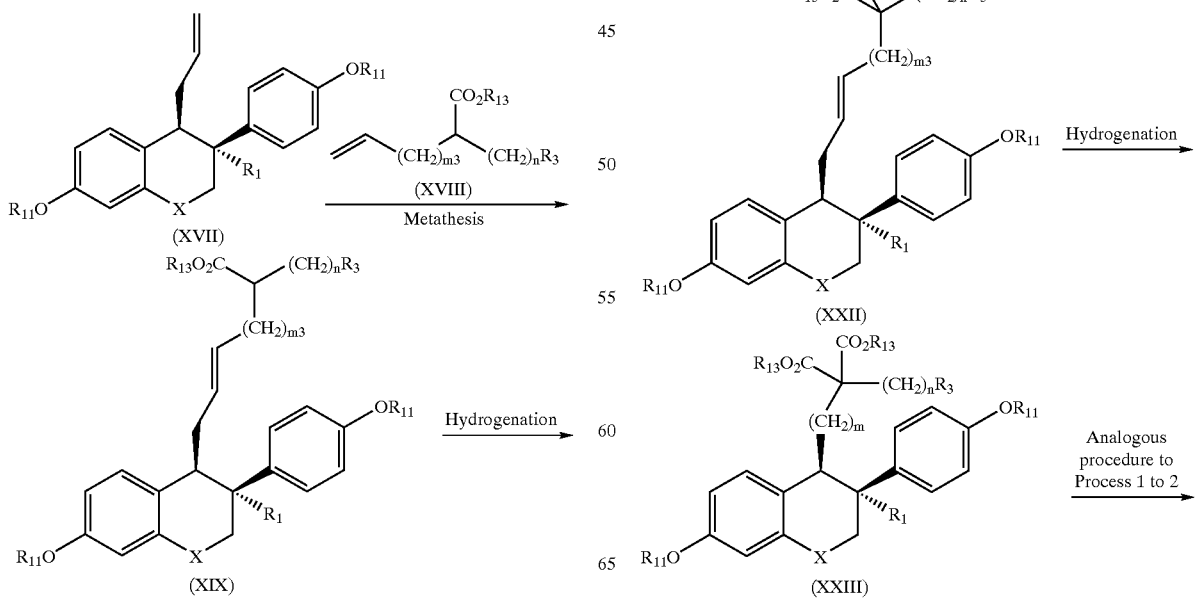

In the above Reaction Scheme 4 (Process 4), $R_1$, $R_3$, X, m and n are as defined above in general formula (1); each of $R_{11}$ and $R_{13}$ represents a protecting group; and $m_3+3$ equals m.

Reaction Scheme 5

(Process 5)

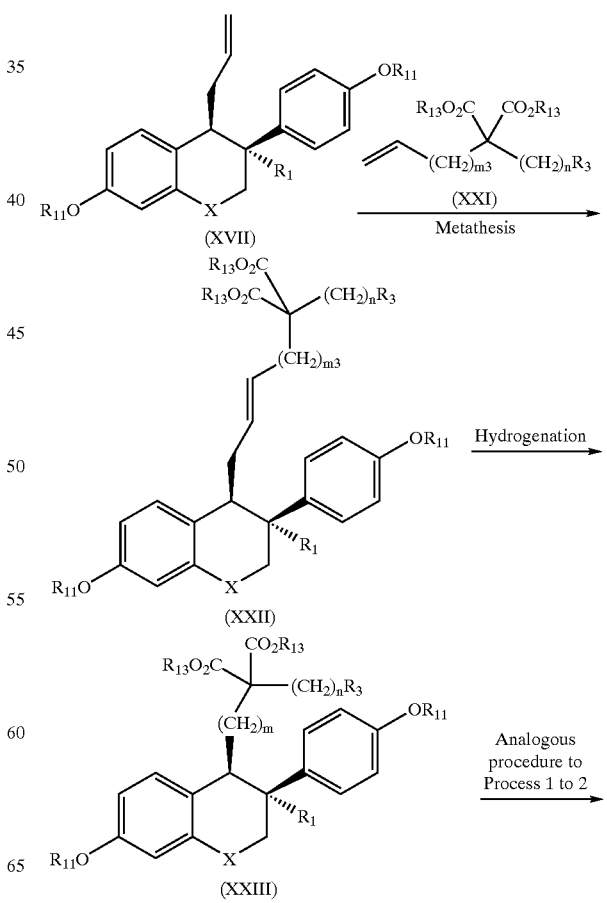

-continued

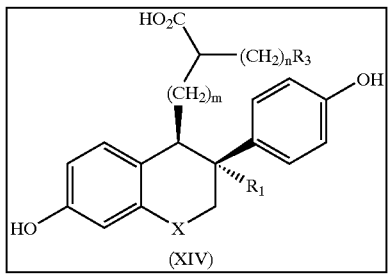

In the above Reaction Scheme 5 (Process 5), $R_1$, $R_3$, X, m and n are as defined above in general formula (1); each of $R_{11}$ and $R_{13}$ represents a protecting group; and $m_3+3$ equals m.

The preparation of the compounds according to the present invention will be illustrated below in more detail, in line with the above-mentioned reaction schemes.

Process 1

In the presence of a base (e.g., n-butyllithium, s-butyllithium, sodium hydride), compound (I) is reacted with alkyne (II) in an inert solvent (e.g., tetrahydrofuran, diethyl ether, dioxane, dichloromethane, chloroform, preferably tetrahydrofuran or dioxane) at a temperature ranging from −78° C. to the boiling point of the reaction mixture, preferably from −78° C. to room temperature, to give compound (III).

In the presence of a Lewis acid such as zinc iodide, compound (III) is reduced with sodium cyanoborohydride ($NaBH_3CN$) in an inert solvent (e.g., tetrahydrofuran, diethyl ether, dioxane, dichloromethane, dichloroethane or chloroform, preferably dichloroethane) at a temperature ranging from −78° C. to the boiling point of the reaction mixture, preferably from 0° C. to room temperature, to give compound (IV).

Using a catalyst (e.g., palladium on activated carbon, palladium hydroxide, platinum oxide), compound (IV) is hydrogenated in an inert solvent (e.g., methanol, ethanol, ethyl acetate, tetrahydrofuran, dioxane, preferably tetrahydrofuran, ethyl acetate) at a temperature ranging from room temperature to the boiling point of the reaction mixture, preferably at room temperature, to give compound (V). Compound (V) can be directly prepared from compound (III) through hydrogenation using a catalyst (e.g., palladium on activated carbon, palladium hydroxide or platinum oxide) in an inert solvent (e.g., methanol, ethanol, ethyl acetate, tetrahydrofuran, dioxane, preferably tetrahydrofuran, ethyl acetate) at a temperature ranging from room temperature to the boiling point of the reaction mixture, preferably at room temperature.

Compound (V) is subjected to deprotection of the alcoholic hydroxyl group in an inert solvent to give compound (VI).

In the presence of a base (e.g., triethylamine or pyridine), compound (VI) is treated with methanesulfonyl chloride or p-toluenesulfonyl chloride in an inert solvent (e.g., tetrahydrofuran, dioxane, dichloromethane, dichloroethane or chloroform, preferably dichloromethane) at a temperature ranging from room temperature to the boiling point of the reaction mixture, preferably at room temperature, to convert $(CH_2)_m OH$ in compound (VI) into $(CH_2)_m—O—SO_2CH_3$ or $(CH_2)_m—O—SO_2—C_6H_4—p—CH_3$. The compound thus obtained is then treated with a metal halide (e.g., sodium iodide or potassium iodide) in an inert solvent (e.g., acetone, tetrahydrofuran, dioxane, dichloromethane, dichloroethane or chloroform, preferably acetone) at a temperature ranging from room temperature to the boiling point of the reaction mixture, preferably at the boiling point of the reaction mixture, to give compound (VII).

In the presence of a base (e.g., sodium hydride, sodium hydroxide or potassium t-butoxide), compound (VII) is reacted with a malonic ester of formula (VIII) (e.g., diethyl malonate or dimethyl malonate) in an inert solvent (e.g., tetrahydrofuran, dioxane, dimethylformamide, dichloromethane, dichloroethane or chloroform, preferably tetrahydrofuran) at a temperature ranging from room temperature to the boiling point of the reaction mixture to give compound (IX).

In the presence of a base (e.g., sodium hydride, sodium hydroxide or potassium t-butoxide), compound (IX) is reacted with an alkylating agent of formula (X) in an inert solvent (e.g., tetrahydrofuran, diethyl ether, dioxane, dimethylformamide, dichloromethane, dichloroethane or chloroform, preferably tetrahydrofuran) at a temperature ranging from room temperature to the boiling point of the reaction mixture to give compound (XI).

Compound (XI) is treated with sodium hydroxide or potassium hydroxide in a solvent (e.g., water, ethanol, methanol, a water/ethanol mixture or a water/methanol mixture) at a temperature ranging from room temperature to the boiling point of the reaction mixture, preferably at the boiling point of the reaction mixture, to give compound (XII).

In a solvent (e.g., dimethyl sulfoxide, dimethylformamide, benzene, toluene, xylene, dioxane or tetrahydrofuran) and, if necessary, in the presence of an acid (e.g., hydrogen chloride, sulfuric acid or p-toluenesulfonic acid), compound (XII) is heated to a temperature ranging from 50° C. to the boiling point of the reaction mixture to give compound (XIII).

Next, compound (XIII) is subjected to deprotection of the phenolic hydroxyl group to give compound (XIV).

Process 2

Compound (XIV) may also be synthesized from compound (XII) in the following manner. A procedure analogous to Process 1 is repeated until compound (XII) is prepared.

Compound (XII) is subjected to deprotection of the phenolic hydroxyl group to give compound (XV).

In a solvent (e.g., dimethyl sulfoxide, dimethylformamide, benzene, toluene, xylene, dioxane or tetrahydrofuran) and, if necessary, in the presence of an acid (e.g., hydrogen chloride, sulfuric acid or p-toluenesulfonic acid), compound (XV) is heated to a temperature ranging from 50° C. to the boiling point of the reaction mixture to give compound (XIV).

Process 3

Compound (XIV) can also be prepared from compound (VII) in the following manner.

In the presence of a base (e.g., sodium hydride, sodium hydroxide or potassium t-butoxide), compound (VII) is reacted with compound (XVI) in an inert solvent (e.g., tetrahydrofuran, dioxane, dimethylformamide, dichloromethane, dichloroethane or chloroform, preferably tetrahydrofuran) at a temperature ranging from −78° C. to the boiling point of the reaction mixture to give compound (XI).

Compound (XI) is converted into compound (XIV) as in Process 1 or 2.

Process 4

Compound (XIV) may also be prepared in the following manner.

In the presence of a catalyst such as benzylidene-bis(tricyclohexylphosphine)dichlororuthenium, compound (XVII) is reacted with compound (XVIII) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XIX).

Using a catalyst (e.g., palladium on activated carbon, palladium hydroxide, platinum oxide or Wilkinson's catalyst), compound (XIX) is hydrogenated in an inert solvent (e.g., methanol, ethanol, ethyl acetate, tetrahydrofuran, dioxane or benzene) at a temperature ranging from room temperature to the boiling point of the reaction mixture, preferably at room temperature, to give compound (XX).

Compound (XX) is converted into compound (XIV) as in Process 1 or 2 where compound (XI) is converted into compound (XIV).

Process 5

Further, compound (XIV) may also be prepared in the following manner.

In the presence of a catalyst such as benzylidene-bis(tricyclohexylphosphine)dichlororuthenium, compound (XVII) is reacted with compound (XXI) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XXII).

Using a catalyst (e.g., palladium on activated carbon, palladium hydroxide, platinum oxide or Wilkinson's catalyst), compound (XXII) is hydrogenated in an inert solvent (e.g., methanol, ethanol, ethyl acetate, tetrahydrofuran, dioxane, dichloromethane, dichloroethane or benzene) at a temperature ranging from room temperature to the boiling point of the reaction mixture, preferably at room temperature, to give compound (XXIII).

Compound (XXIII), which is identical with compound (XI) in Process 1, is converted into compound (XIV) as in Process 1 or 2 where compound (XI) is converted into compound (XIV).

Compound (XVII) used in Processes 4 and 5 can be prepared by either Process 6 or 7 shown below.

Reaction Scheme 6

(Process 6)

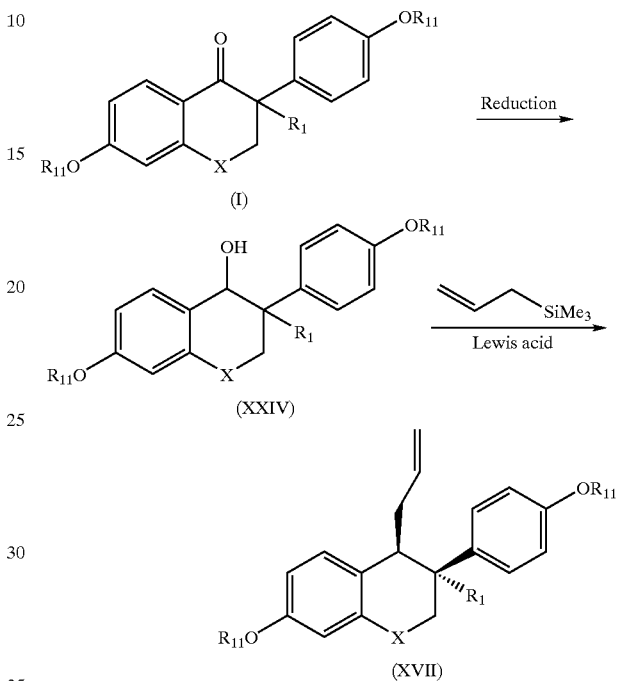

Reaction Scheme 7

(Process 7)

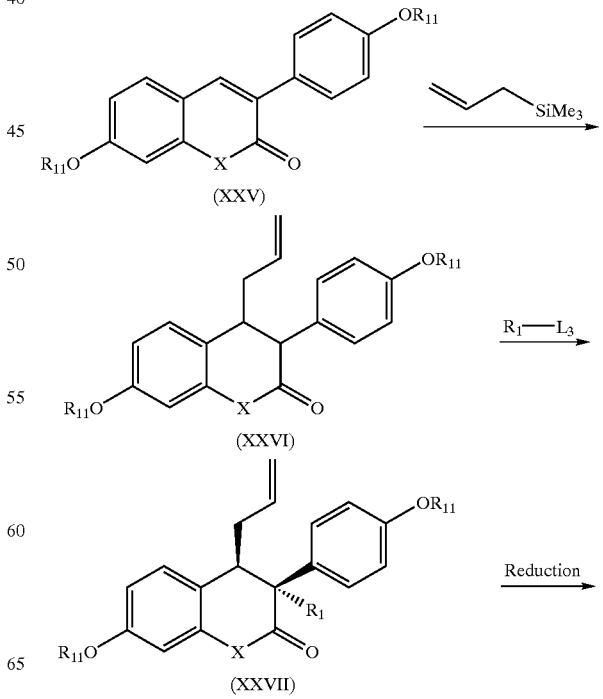

-continued

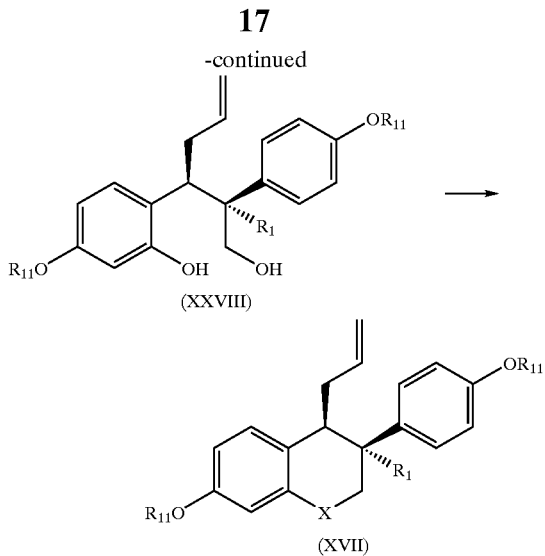

In the above Reaction Scheme 7 (Process 7), X is as defined above in general formula (1); $R_{11}$ represents a protecting group; and $L_3$ represents a leaving group.

Process 6

Preparation of Compound (XVII)—Part I

Compound (I) is reduced with lithium aluminum hydride or diisobutylaluminum hydride in an inert solvent (e.g., diethyl ether, benzene, toluene, xylene, dioxane or tetrahydrofuran) at a temperature ranging from −78° C. to the boiling point of the reaction mixture to give compound (XXIV).

In the presence of a Lewis acid such as zinc iodide, compound (XXIV) is reacted with allyltrimethylsilane in an inert solvent (e.g., tetrahydrofuran, dioxane, dichloromethane, dichloroethane or chloroform, preferably dichloroethane) at a temperature ranging from −78° C. to the boiling point of the reaction mixture, preferably from 0° C. to room temperature, to give compound (XVII).

Process 7

Preparation of Compound (XVII)—Part II

In the presence of anhydrous TBAF and, if necessary, accompanied by addition of HMPA, compound (XXV) is reacted with allyltrimethylsilane in an inert solvent (e.g., dimethylformamide, dimethyl sulfoxide, tetrahydrofuran, dioxane, dichloromethane, dichloroethane or chloroform) at a temperature ranging from −78° C. to the boiling point of the reaction mixture, preferably from 0° C. to room temperature, to give compound (XXVI).

In the presence of a base (e.g., lithium hexamethyldisilazide, n-butyllithium, s-butyllithium, sodium hydride), compound (XXVI) is reacted with an alkylating agent ($R_1$-$L_3$) in an inert solvent (e.g., tetrahydrofuran, ether, dioxane, dichloromethane, chloroform, preferably tetrahydrofuran or dioxane) at a temperature ranging from −78° C. to the boiling point of the reaction mixture, preferably from −78° C. to room temperature, to give compound (XXVII).

Compound (XXVII) is reduced with lithium aluminum hydride in an inert solvent (e.g., tetrahydrofuran, dioxane or diethyl ether) at a temperature ranging from −78° C. to the boiling point of the reaction mixture to give compound (XXVIII).

Compound (XXVIII) is reacted with diethyl azodicarboxylate and triphenylphosphine in an inert solvent (e.g., toluene, dioxane, dimethylformamide, dimethyl sulfoxide, tetrahydrofuran, dichloromethane, dichloroethane or chloroform) at a temperature ranging from −78° C. to the boiling point of the reaction mixture, preferably from 0° C. to room temperature, to give compound (XVII).

Compound (XIV) given by the above Processes 1 to 5 may also be converted into a salt form because it has a carboxyl group. Pharmaceutically acceptable salts include, sodium, potassium and calcium salts. For example, a salt of compound (XIV) can be prepared as follows.

Sodium methoxide is added to compound (XIV) dissolved in an organic solvent (e.g., dry methanol) at an appropriate temperature, for example, at room temperature, and the resulting mixture is stirred for about 30 minutes to about 3 hours at the same temperature. After addition of an organic solvent such as dry diethyl ether, the reaction mixture is evaporated under reduced pressure to remove the solvent, thereby obtaining a salt of the compound.

The compound of the present invention exists as various enantiomers because it contains three asymmetric carbon atoms. To obtain a single stereoisomer, there are two techniques, one of which uses a chiral column to resolve a mixture of stereoisomers and the other involves asymmetric synthesis. The chiral column technique may be carried out using a column commercially available from DAICEL under the trade name of CHIRALPAK-OT(+), OP(+) or AD, or CHIRALCEL-OA, OB, OJ, OK, OC, OD, OF or OG, for example. Regarding asymmetric synthesis, the following will illustrate the asymmetric synthesis of the inventive compound with respect to an asymmetric carbon atom, to which a side chain carboxyl group is attached.

Reaction Scheme 8

(Process 8)

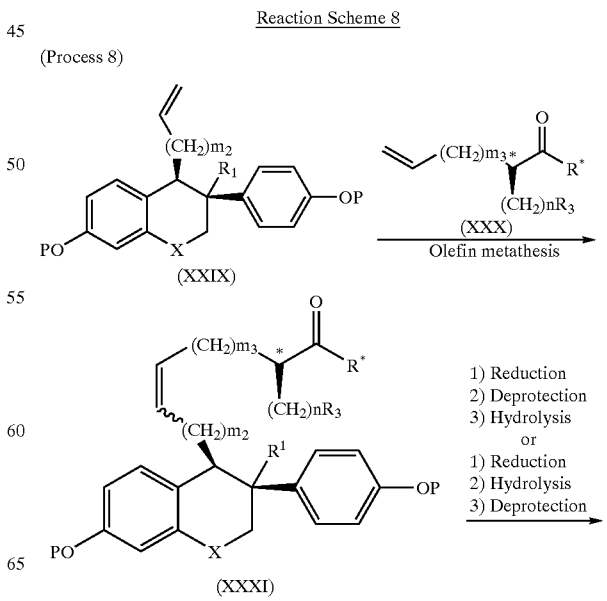

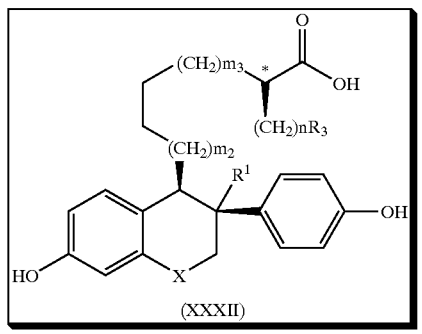

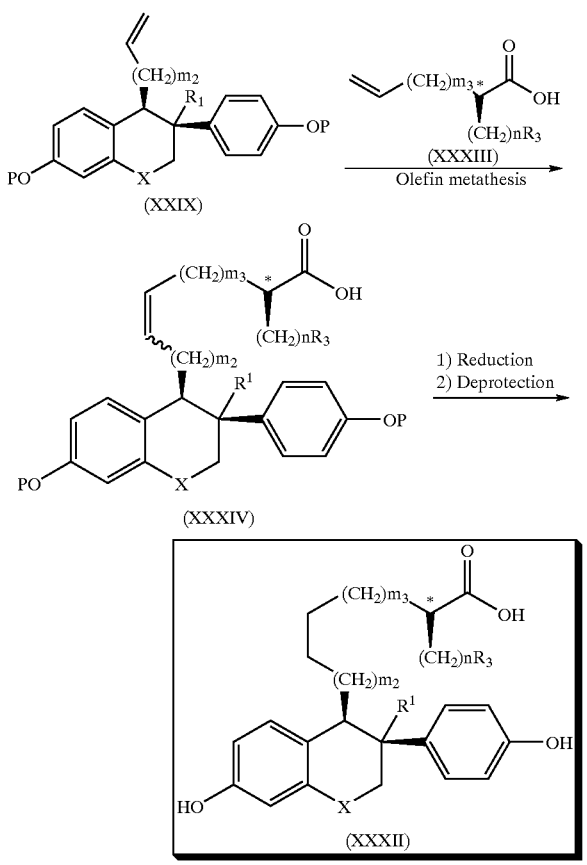

Process 8

In the presence of a catalyst such as benzylidene-bis(tricyclohexylphosphine)dichlororuthenium, compound (XXIX) is reacted with compound (XXX) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XXXI).

Compound (XXXI) is then subjected to the following reactions in the order stated, (a) reduction, deprotection and hydrolysis or (b) reduction, hydrolysis and deprotection, to give compound (XXXII).

(a) Reduction, Deprotection and Hydrolysis
1) Reduction
In the presence of a catalyst (e.g., palladium on activated carbon, palladium hydroxide, platinum oxide or Wilkinson's catalyst), compound (XXXI) is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.
2) Deprotection
Next, deprotection of the phenolic hydroxyl group is carried out to give a deprotected product.
3) Hydrolysis
By way of example, if R* is a group of formula (XXXVIII), the deprotected product is further treated with lithium hydroxide, sodium hydroxide, lithium hydroxide plus hydrogen peroxide, sodium hydroxide plus hydrogen peroxide, or tetrabutylammonium hydroxide plus hydrogen peroxide in a solvent (e.g., a tetrahydrofuran/water mixture, a diethyl ether/water mixture, a dioxane/water mixture, a methanol/water mixture, an ethanol/water mixture) at a temperature ranging from room temperature to the boiling point of the reaction mixture, preferably at room temperature, to give compound (XXXII).

(b) Reduction, Hydrolysis and Deprotection
1) Reduction
In the presence of a catalyst (e.g., palladium on activated carbon, palladium hydroxide, platinum oxide or Wilkinson's catalyst), compound (XXXI) is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.
2) Hydrolysis
By way of example, if R* is a group of formula (XXXVIII), the reduction product is further treated with lithium hydroxide, sodium hydroxide, lithium hydroxide plus hydrogen peroxide, sodium hydroxide plus hydrogen peroxide, or tetrabutylammonium hydroxide plus hydrogen peroxide in a solvent (e.g., a tetrahydrofuran/water mixture, a diethyl ether/water mixture, a dioxane/water mixture, a methanol/water mixture, an ethanol/water mixture) at a temperature ranging from room temperature to the boiling point of the reaction mixture, preferably at room temperature, to give a carboxylic acid.
3) Deprotection
Next, deprotection of the phenolic hydroxyl group is carried out to give compound (XXXII).

Process 9

In the presence of a catalyst such as benzylidene-bis(tricyclohexylphosphine)dichlororuthenium, compound (XXIX) is reacted with compound (XXXIII) in a solvent (e.g., methylene chloride, chloroform, benzene, toluene, xylene, dioxane, tetrahydrofuran, dimethyl sulfoxide or dimethylformamide) at a temperature ranging from −78° C. to the boiling point of the reaction mixture, preferably at the boiling point of the reaction mixture, to give compound (XXXIV).

In the presence of a catalyst (e.g., palladium on activated carbon, palladium hydroxide, platinum oxide or Wilkinson's catalyst), compound (XXXIV) is hydrogenated in an inert solvent (e.g., methanol, ethanol, ethyl acetate, tetrahydrofuran, dioxane or benzene) at a temperature ranging from 0° C. to the boiling point of the reaction mixture, preferably at room temperature, to give a reduction product.

Next, deprotection of the phenolic hydroxyl group is carried out to give compound (XXXII).

The chiral olefins of formulae (XXX) and (XXXIII) used in the above Processes 8 and 9, respectively, may be synthesized as follows.

Reaction Scheme 10

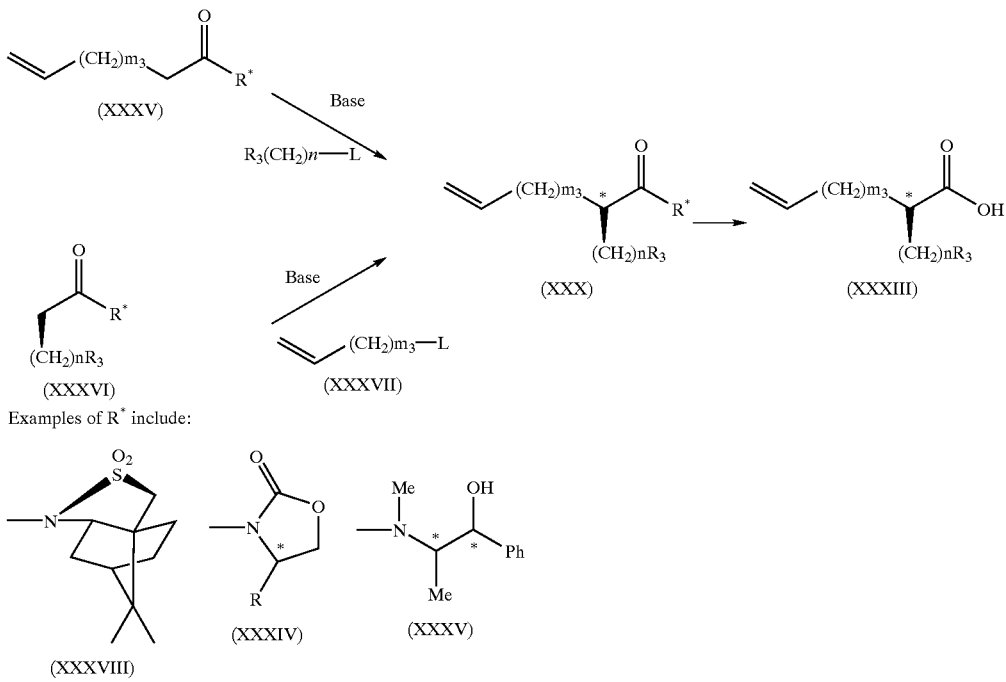

Examples of R* include: (XXXVIII), (XXXIV), (XXXV)

In the above Reaction Schemes 8, 9 and 10 (Processes 8, 9 and 10), $R_1$, $R_3$, X, m and n are as defined above in general formula (1); R* represents a chiral auxiliary group; P represents a leaving group; L represents a leaving group; and $m_2$ and $m_3$ are integers that satisfy the relation $m=m_2+m_3+2$. The symbol R in formula (XXXIV) represents an alkyl group.

Synthesis of Chiral Olefins

In the presence of a base (e.g., lithium diisopropylamide, lithium hexamethyl-disilazide, sodium hexamethyl-disilazide, butyllithium) and HMPA, compound (XXXV) is reacted with $R_3(CH_2)_n$—L in an inert solvent (e.g., tetrahydrofuran, toluene, diethyl ether, hexane, preferably tetrahydrofuran) at a temperature ranging from −78° C. to the boiling point of the reaction mixture, preferably from −30° C. to room temperature, to give compound (XXX).

Alternatively, in the presence of a base (e.g., lithium diisopropylamide, lithium hexamethyl-disilazide, sodium hexamethyl-disilazide, butyllithium) and HMPA, compound (XXXVI) is reacted with compound (XXXVII) in an inert solvent (e.g., tetrahydrofuran, toluene, diethyl ether, hexane, preferably tetrahydrofuran) at a temperature ranging from −78° C. to the boiling point of the reaction mixture, preferably from −30° C. to room temperature, to give compound (XXX).

In the presence of a nucleophilic reagent (e.g., lithium hydroxide plus hydrogen peroxide, lithium hydroxide, sodium methoxide, sodium thioethoxide) or an acid (e.g., hydrochloric acid, sulfuric acid), compound (XXX) is hydrolyzed in an inert solvent (e.g., methanol, ethanol, tetrahydrofuran, water, preferably a tetrahydrofuran/water mixture) at a temperature ranging from −78° C. to the boiling point of the reaction mixture, preferably from room temperature to 50° C., to convert the chiral auxiliary group R* into OH.

In the case where each of $R_4$ and $R_5$ is an acyl group or an alkyl group, the synthesis can be carried out according to Process 9.

EXAMPLES

The present invention is more specifically explained by the following examples. However, it should be understood that the present invention is not limited to these examples in any manner. In order to explain the effectiveness of the compounds according to the present invention, typical compounds were tested for their anti-estrogenic activity in the test example shown below. Tables 1 and 2 show chemical structures of the compounds prepared in the Examples.

TABLE 1

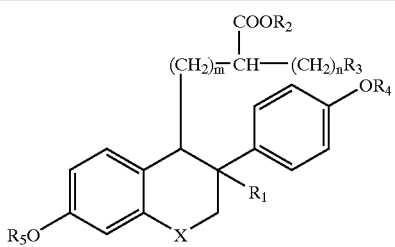

| Example No. | X | $R_1$ | $R_2$ | $R_3$ | $R_4$ | $R_5$ | m | n |
|---|---|---|---|---|---|---|---|---|
| 13 | S | Et | H | —$CF_2CF_3$ | H | H | 8 | 6 |
| 14 | S | Et | H | —$CF_2CF_3$ | H | H |   | 5 |
| 15 | S | Et | H | —$CF_2CF_3$ | H | H |   | 4 |
| 16 | S | Et | H | —$CF_2CF_3$ | H | H |   | 3 |

TABLE 1-continued

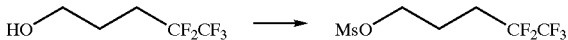

| Example No. | X | R₁ | R₂ | R₃ | R₄ | R₅ | m | n |
|---|---|---|---|---|---|---|---|---|
| 31 | S | Et | H | —(CF₂)₃CF₃ | H | H |   | 2 |
| 17 | S | Et | H | —CF₂CF₃ | H | H | 9 | 6 |
| 18 | S | Et | H | —CF₂CF₃ | H | H |   | 5 |
| 19 | S | Et | H | —CF₂CF₃ | H | H |   | 4 |
| 20 | S | Et | H | —CF₂CF₃ | H | H |   | 3 |
| 30 | S | Et | H | —(CF₂)₃CF₃ | H | H |   | 2 |
| 25 | O | Et | H | —CF₂CF₃ | H | H | 8 | 6 |
| 26 | O | Et | H | —CF₂CF₃ | H | H |   | 5 |
| 27 | O | Et | H | —CF₂CF₃ | H | H |   | 4 |
| 28 | O | Et | H | —CF₂CF₃ | H | H |   | 3 |
| 33 | O | Et | H | —(CF₂)₃CF₃ | H | H |   | 2 |
| 21 | O | Et | H | —CF₂CF₃ | H | H | 9 | 6 |
| 22 | O | Et | H | —CF₂CF₃ | H | H |   | 5 |
| 23 | O | Et | H | —CF₂CF₃ | H | H |   | 4 |
| 24 | O | Et | H | —CF₂CF₃ | H | H |   | 3 |
| 32 | O | Et | H | —(CF₂)₃CF₃ | H | H |   | 2 |
| 29 | S | n-Pr | H | —CF₂CF₃ | H | H | 8 | 3 |

TABLE 2

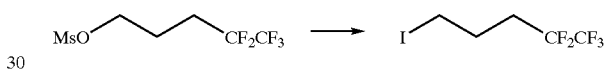

| Example No. | X | R₁ | R₂ | R₃ | R₄ | R₅ | m | n |
|---|---|---|---|---|---|---|---|---|
| 34 | O | Et | H | —(CF₂)₃CF₃ | H | H | 8 | 3 |
| 35 | O | Et | H | —(CF₂)₃CF₃ | H | H | 9 | 3 |
| 36 | S | n-Pr | H | —CF₂CF₃ | H | H | 8 | 4 |
| 37 | S | n-Pr | H | —(CF₂)₃CF₃ | H | H | 8 | 2 |
| 38 | S | n-Pr | H | —CF₂CF₃ | H | H | 9 | 3 |
| 39 | S | n-Pr | H | —(CF₂)₃CF₃ | H | H | 9 | 2 |
| 40 | O | n-Pr | H | —CF₂CF₃ | H | H | 8 | 4 |
| 41 | O | n-Pr | H | —(CF₂)₃CF₃ | H | H | 8 | 2 |
| 42 | O | n-Pr | H | —(CF₂)₃CF₃ | H | H | 8 | 3 |
| 43 | O | n-Pr | H | —CF₂CF₃ | H | H | 9 | 3 |
| 44 | O | n-Pr | H | —CF₂CF₃ | H | H | 9 | 4 |
| 45 | O | n-Pr | H | —(CF₂)₃CF₃ | H | H | 9 | 2 |
| 46 | O | n-Pr | H | —(CF₂)₃CF₃ | H | H | 9 | 3 |
| 47 | O | n-Bu | H | —(CF₂)₃CF₃ | H | H | 8 | 3 |
| 50, Peak 1 | O | n-Pr | H | —(CF₂)₃CF₃ | H | H | 8 | 3 |
| 50, Peak 2 | O | n-Pr | H | —(CF₂)₃CF₃ | H | H | 8 | 3 |
| 52, Peak 1 | O | n-Pr | H | —(CF₂)₃CF₃ | H | H | 8 | 3 |
| 52, Peak 2 | O | n-Pr | H | —(CF₂)₃CF₃ | H | H | 8 | 3 |

Example 1

Synthesis of 1-iodo-4,4,5,5,5-pentafluoropentane (Step 1)

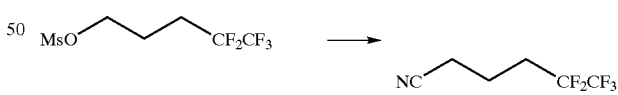

Trietylamine (46 ml, 0.330 mol) was added to a solution of 4,4,5,5,5-pentafluoropentan-1-ol (25 g, 0.132 mol) in dichloromethane (50 ml). To this solution, methanesulfonyl chloride (20.4 ml, 0.264 mol) was added at 0° C., followed by stirring for 3 hours at room temperature under argon atmosphere. After the reaction was completed, water was added to the reaction mixture, which was then extracted with dichloromethane. The organic layer was washed with 1N aqueous hydrochloric acid, water and saturated aqueous sodium chloride, and then dried over anhydrous magnesium sulfate. After distilling off the solvent, the residue was purified by silica gel flash column chromatography (eluent: hexane/ethyl acetate=1/1) to give 1-methanesulfonyloxy-4,4,5,5,5-pentafluoropentane (34 g, quantitative).

$^1$H-NMR (300 MHz, CDCl₃): d 4.30 (t, 2H), 3.05 (s, 3H), 2.30–2.05 (m, 4H).

(Step 2)

Sodium iodide (35.1 g, 2.15 mol) was added to a solution of 1-methanesulfonyloxy-4,4,5,5,5-pentafluoropentane (20 g, 0.781 mol) in acetone (200 ml), followed by heating under reflux for 12 hours. After the reaction mixture was filtered, the filtrate was concentrated. Ethyl acetate was added to the residue, which was then filtered again. The filtrate was washed with water and saturated aqueous sodium chloride, and then dried over anhydrous magnesium sulfate. The solvent was distilled off to give 1-iodo-4,4,5,5,5-pentafluoropentane (21.1 g, Yield 93.4%).

$^1$H-NMR (300 MHz, CDCl₃): d 3.22 (t, 2H, J=6.8 Hz), 2.28–2.10 (m, 4H).

Example 2

Synthesis of 1-Iodo-5,5,6,6,6-pentafluorohexane (Step 1)

1-Methanesulfonyloxy-4,4,5,5,5-pentafluoropentane (138 g, 538.62 mmol) was dissolved in dimethyl sulfoxide (1000 ml). Sodium cyanide (55.57 g, 1.077 mol) and 18-crown-6 (2.85 g, 10.77 mmol) were added to the solution followed by stirring for 2 hours at 100° C. After cooling to room temperature, water was added to the reaction mixture, which was then extracted twice with ether. The combined organic layers were washed with water and saturated aqueous sodium chloride, and then dried over anhydrous magnesium sulfate. The solvent was distilled off to give 5,5,6,6,6-pentafluorohexanecarbonitrile (108 g, Yield 100%).

$^1$H-NMR (300 MHz, CDCl₃): δ 2.47 (t, 2H), 2.26–2.11 (m, 2H), 2.02–1.93 (m, 2H).

(Step 2)

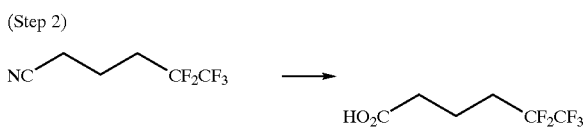

Concentrated sulfuric acid (350 ml) was slowly added dropwise to 5,5,6,6,6-pentafluorohexanecarbonitrile (108 g, 577.20 mmol) at 0° C., and the resulting mixture was stirred for 3 hours at room temperature. Water (350 ml) was slowly added dropwise to this mixture at 0° C., followed by heating under reflux for 12 hours. After cooling to room temperature, water was added to the reaction mixture, which was then extracted three times with dichloromethane. The combined organic layers were washed with water and saturated aqueous sodium chloride, and then dried over anhydrous magnesium sulfate. The solvent was distilled off to give 5,5,6,6,6-pentafluorohexanoic acid (95.8 g, Yield 85%).

$^1$H-NMR (300 MHz, CDCl$_3$): δ 2.45 (t, 2H, J=7.1 Hz), 2.23–2.09 (m, 2H), 2.01–1.92 (m, 2H).

(Step 3)

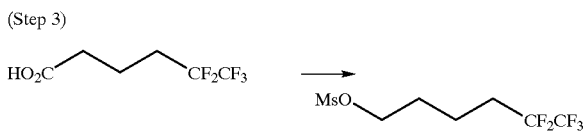

5,5,6,6,6-Pentafluorohexanoic acid (95 g, 460.92 mmol) was dissolved in anhydrous tetrahydrofuran (1L) and cooled to −30° C. To this solution, borane-methyl sulfide complex (10 M in THF, 92.2 ml, 921.84 mmol) was slowly added dropwise, followed by stirring for 3 hours at room temperature. After treatment with methanol at 0° C., water was added to the reaction mixture, which was then extracted twice with ether. The combined organic layers were washed with water and saturated aqueous sodium chloride, and then dried over anhydrous magnesium sulfate. After distilling off the solvent, the resulting residue was dissolved in dichloromethane (1500 ml), and triethylamine (160.6 ml, 1.15 mol) and methanesulfonyl chloride (46.4 ml, 599.19 mmol) were added dropwise thereto at 0° C., followed by stirring for 1 hour. After the reaction was completed, water was added to the reaction mixture, which was then extracted twice with dichloromethane. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/4) to give 1-methanesulfonyloxy-5,5,6,6,6-pentafluorohexane (101 g, Yield 81%).

$^1$H-NMR (300 MHz, CDCl$_3$): δ 4.24 (t, 2H, J=6.0 Hz), 2.98 (s, 3H), 2.19–2.00 (m, 2H), 1.93–1.67 (m, 4H).

(Step 4)

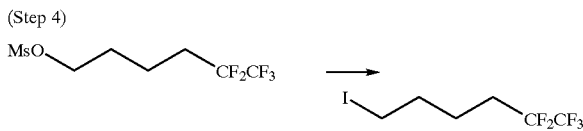

Sodium iodide (168 g, 1.12 mol) was added to a solution of 1-methanesulfonyloxy-5,5,6,6,6-pentafluorohexane (101 g, 373.77 mmol) in acetone (2000 ml), followed by heating under reflux for 12 hours. Water was added to the reaction mixture, which was then extracted twice with ether. The combined organic layers were washed with 1% aqueous sodium thiosulfate and saturated aqueous sodium chloride, and then dried over anhydrous magnesium sulfate. After distilling off the solvent, the residue was purified by silica gel column chromatography (eluent: pentane) to give 1-iodo-5,5,6,6,6-pentafluorohexane (93.6 g, Yield 83%).

$^1$H-NMR (300 MHz, CDCl$_3$): δ 3.20 (t, 2H, J=6.9 Hz), 2.27–1.87 (m, 4H), 1.78–1.69 (m, 2H).

Example 3

Synthesis of 1-Iodo-6,6,7,7,7-pentafluoroheptane (Step 1)

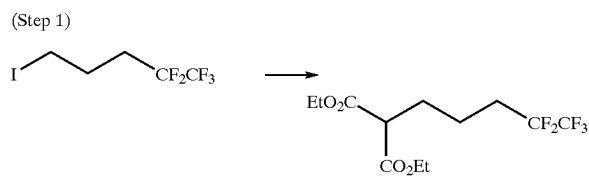

Sodium hydride (60%, 2.87 g, 71.87 mmol) was added to anhydrous tetrahydrofuran (250 ml) and cooled to 0° C. To this mixture, diethyl malonate (12.12 ml, 79.86 mmol) was slowly added dropwise, followed by stirring for 1 hour at room temperature. 1-Iodo-4,5,5,5-pentafluoropentane (11.5 g, 39.93 mmol) dissolved in anhydrous tetrahydrofuran (50 ml) was then slowly added dropwise to the reaction mixture, followed by stirring for 12 hours at room temperature. Water was added to the reaction mixture, which was then extracted twice with ethyl acetate. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/40) to give diethyl 2-(4,4,5,5,5-pentafluoropentyl)malonate (11.2 g, Yield 88%).

$^1$H-NMR (300 MHz, CDCl$_3$): δ 4.21 (m, 4H), 3.34 (t, 1H, J=7.27), 2.09–1.94 (m, 4H), 1.68–1.62 (m, 2H), 1.27 (t, 6H, J=7.15 Hz).

(Step 2)

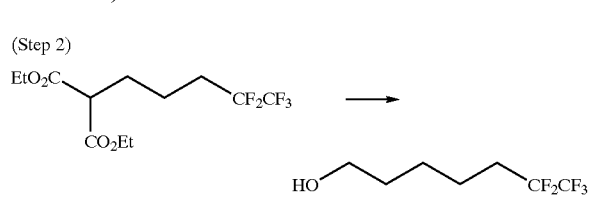

A solution of potassium hydroxide (370 g, 6.6 mol) in water (500 ml) was added to a solution of diethyl 2-(4,4,5,5,5-pentafluoropentyl)malonate (105.3 g, 0.33 mol) in ethanol (1000 ml), followed by stirring for 16 hours at 60° C. The reaction mixture was adjusted to pH 5 by slowly adding 1N hydrochloric acid dropwise, and then extracted twice with ethyl acetate. The combined organic layers were washed with saturated aqueous sodium chloride and dried over anhydrous magnesium sulfate. After distilling off the solvent, the residue was dissolved in dimethyl sulfoxide (500 ml) and stirred for 18 hours at 170° C. Water was added to the reaction mixture, which was then extracted three times with ethyl acetate. The combined organic layers were washed with water and saturated aqueous sodium chloride, and then dried over anhydrous magnesium sulfate. After distilling off the solvent, the residue was dissolved in anhydrous tetrahydrofuran (300 ml) and cooled to −30° C. Borane-methyl sulfide complex (10 M in THF, 55 ml, 0.55 mol) was slowly added dropwise to the solution, followed by stirring for 3 hours at room temperature. After treatment with methanol at 0° C., water was added to the reaction mixture, which was then extracted twice with ethyl acetate. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/20) to give 6,6,7,7,7-pentafluoroheptan-1-ol (39 g, Yield 57%).

$^1$H-NMR (300 MHz, CDCl$_3$): δ 3.66 (t, 2H), 2.17–1.94 (m, 2H), 1.68–1.53 (m, 4H), 1.53–1.41 (m, 2H).

(Step 3)

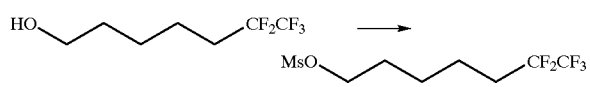

Triethylamine (25.83 ml, 185.3 mmol) and methanesulfonyl chloride (6.9 ml, 88.9 mmol) were added dropwise to a solution of 6,6,7,7,7-pentafluoroheptan-1-ol (14.1 g, 74.1 mmol) in dichloromethane (350 ml) at 0° C., followed by stirring for 1 hour. After the reaction was completed, water was added to the reaction mixture, which was then extracted twice with dichloromethane. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/10) to give 1-methanesulfonyloxy-6,6,7,7,7-pentafluoroheptane (17.3 g, Yield 82%).

$^1$H-NMR (300 MHz, CDCl$_3$): δ 4.24 (t, 2H), 3.01 (s, 3H), 2.13–1.96 (m, 2H), 1.85–1.76 (m, 2H), 1.70–1.47 (m, 4H).

(Step 4)

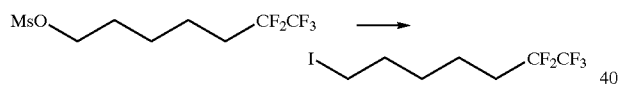

Sodium iodide (27.37 g, 182.58 mmol) was added to a solution of 1-methanesulfonyloxy-6,6,7,7,7-pentafluoroheptane (17.3 g, 60.86 mmol) in acetone (500 ml), followed by heating under reflux for 12 hours. Water was added to the reaction mixture, which was then extracted twice with ether. The combined organic layers were washed with 1% aqueous sodium thiosulfate and saturated aqueous sodium chloride, and then dried over anhydrous magnesium sulfate. The solvent was distilled off to give 1-iodo-6,6,7,7,7-pentafluoroheptane (16.5 g, Yield 86%).

$^1$H-NMR (300 MHz, CDCl$_3$): δ 3.20 (t, 2H), 2.11–1.98 (m, 2H), 1.92–1.83 (m, 2H), 1.63–1.50 (m, 4H).

Example 4

Synthesis of 1-Iodo-7,7,8,8,8-Pentafluorooctane (Step 1)

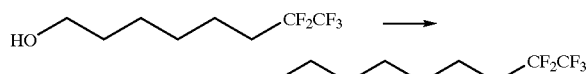

7,7,8,8,8-Pentafluorooctan-1-ol (25 g, 113 mmol) was dissolved in dichloromethane (250 ml) and cooled to 0° C.

To this solution, triethylamine (47.4 ml, 339 mmol) and methanesulfonyl chloride (17.6 ml, 227 mmol) were added dropwise, followed by stirring for 1 hour. After the reaction was completed, water was added to the reaction mixture, which was then extracted twice with dichloromethane. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/10) to give 1-methanesulfonyloxy-7,7,8,8,8-pentafluorooctane (30 g, Yield 89%).

$^1$H-NMR (300 MHz, CDCl$_3$): δ 4.24 (t, 2H), 3.01 (s, 3H), 2.13–1.96 (m, 2H), 1.85–1.76 (m, 2H), 1.70–1.47 (m, 6H).

(Step 2)

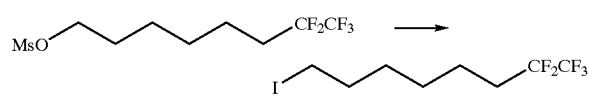

Sodium iodide (19.62 g, 130 mmol) was added to a solution of 1-methanesulfonyloxy-7,7,8,8,8-pentafluorooctane (14 g, 47.01 mmol) in acetone (200 ml), followed by heating under reflux for 12 hours. After the reaction was completed, water was added to the reaction mixture, which was then extracted twice with ether. The combined organic layers were washed with 1% aqueous sodium thiosulfate and saturated aqueous sodium chloride, and then dried over anhydrous magnesium sulfate. The solvent was distilled off to give 1-iodo-7,7,8,8,8-pentafluorooctane (14 g, Yield 89%).

$^1$H-NMR (300 MHz, CDCl$_3$): δ 3.15 (t, 2H), 2.14–1.97 (m, 2H), 1.85–1.75 (m, 2H), 1.70–1.51 (m, 2H), 1.45–1.31 (m, 4H).

Example 5

Synthesis of Ethyl 2-(5,5,6,6,6-Pentafluorohexyl)-9-decenoate (Step 1)

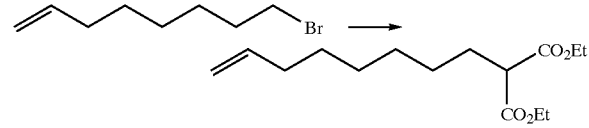

Sodium hydride (60%, 6.3 g, 156.96 mmol) was added to anhydrous tetrahydrofuran (200 ml) under argon atmosphere and cooled to 0° C. To this mixture, diethyl malonate (23.8 ml, 156.95 mmol) was slowly added dropwise, followed by stirring for 1 hour at room temperature. After cooling to 0° C., 8-bromo-1-octene (20 g, 104.64 mmol) was slowly added to the reaction mixture, followed by stirring for 12 hours at room temperature. Water was added to the reaction mixture, which was then extracted with ethyl acetate. The organic layer was washed with saturated aqueous sodium chloride and dried over magnesium sulfate. After distilling off the solvent, the residue was purified by silica gel column chromatography (eluent: ethyl acetate/hexane=1/30) to give diethyl 2-(7-octenyl)malonate (16 g, Yield 56.56%) as a colorless oil.

$^1$H-NMR (300 MHz, CDCl$_3$): δ 5.77 (m, 1H), 5.03–4.83 (m, 2H), 4.17 (q, 4H, J=6.8 Hz), 3.30 (t, 1H, J=7.6 Hz), 2.04–2.00 (m, 2H), 1.98–1.83 (m, 2H), 1.38–1.23 (m, 14H).

(Step 2)

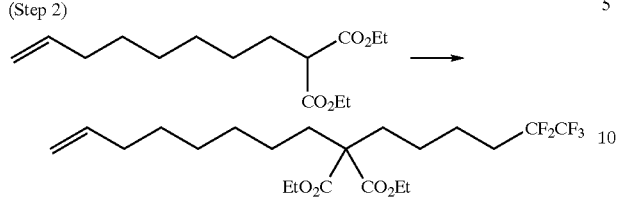

Sodium hydride (60%, 326 mg, 8.14 mmol) was added to dimethyl sulfoxide (5 ml) under argon atmosphere and cooled to 0° C. To this mixture, diethyl 2-(7-octeny) malonate (2 g, 7.40 mmol) dissolved in dimethyl sulfoxide (5 ml) was slowly added, followed by stirring for 1 hour. After cooling to 0° C., 1-iodo-5,5,6,6,6-pentafluorohexane (2.68 g, 8.88 mmol) dissolved in dimethyl sulfoxide (5 ml) was slowly added to the reaction mixture, followed by stirring for 2 hours at room temperature. Water was added to the reaction mixture, which was then extracted with ethyl acetate. The organic layer was washed with water and dried over magnesium sulfate. After distilling off the solvent, the residue was purified by silica gel column chromatography (eluent: ethyl acetate/hexane=1/20) to give diethyl 2-(7-octenyl)-2-(5,5,6,6,6-pentafluorohexyl)malonate (2.3 g, Yield 70%) as a colorless oil.

$^1$H-NMR (300 MHz, CDCl$_3$): δ 5.78 (m, 1H), 5.05–4.85 (m, 2H), 4.19 (q, 4H, J=7.1 Hz), 2.04–1.95 (m, 4H), 1.90–1.80 (m, 4H), 1.65–1.59 (m, 2H), 1.38–1.12 (m, 16H).

(Step 3)

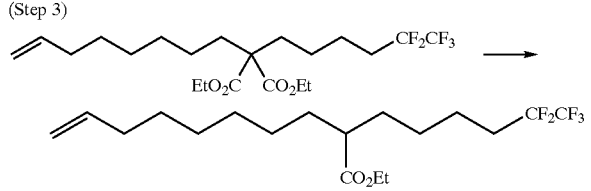

Lithium chloride (401 mg, 9.540 mmol) and water (86 mg, 4.770 mmol) were added to a solution of diethyl 2-(7-octenyl)-2-(5,5,6,6,6-pentafluorohexyl)malonate (2.12 g, 4.770 mmol) in dimethyl sulfoxide (8 ml) followed by stirring for 16 hours at 180° C. After cooling, water was added to the reaction mixture, which was then extracted with ethyl acetate. The organic layer was washed with water and saturated aqueous sodium chloride, and then dried over anhydrous magnesium sulfate. After distilling off the solvent, the residue was purified by silica gel column chromatography (eluent: ethyl acetate/hexane=1/50) to give ethyl 2-(5,5,6,6,6-pentafluorohexyl)-9-decenoate (1.40 g, Yield 79%) as a colorless oil.

$^1$H-NMR (300 MHz, CDCl$_3$): δ 5.79 (m, 1H), 5.04–4.84 (m, 2H), 4.15 (q, 2H, J=7.2 Hz), 2.30 (m, 1H), 2.06–1.97 (m, 4H), 1.66–1.52 (m, 4H), 1.49–1.23 (m, 15H).

Example 6

Synthesis of Ethyl 2-(4,4,5,5,5-Pentafluoropentyl)-9-decenoate

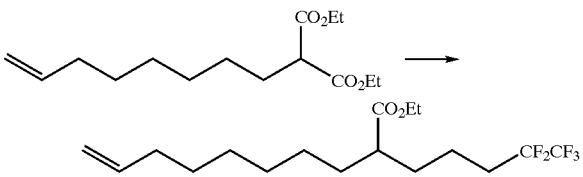

Starting with the diethyl 2-(7-octenyl)malonate prepared in Example 5 and the 1-iodo-4,4,5,5,5-pentafluoropentane prepared in Example 1, the same procedure as shown in Example 5 was repeated to give ethyl 2-(4,4,5,5,5-pentafluoropentyl)-9-decenoate.

$^1$H-NMR (300 MHz, CDCl$_3$): δ 5.80 (m, 1H), 4.97 (m, 2H), 4.15 (q, 2H, J=7.1 Hz), 2.34 (m, 1H), 2.02 (m, 4H), 1.75–1.26 (m, 17H).

Example 7

Synthesis of Ethyl 2-(6,6,7,7,7-Pentafluoroheptyl)-9-decenoate

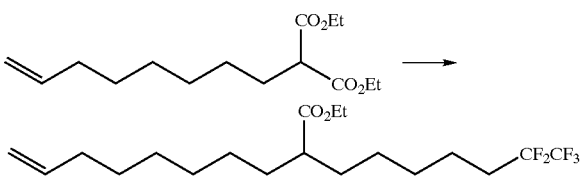

Starting with the diethyl 2-(7-octenyl)malonate prepared in Example 5 and the 1-iodo-6,6,7,7,7-pentafluoroheptane prepared in Example 3, the same procedure as shown in Example 5 was repeated to give ethyl 2-(6,6,7,7,7-pentafluoroheptyl)-9-decenoate.

$^1$H-NMR (300 MHz, CDCl$_3$): δ 5. 78 (m, 1H), 5. 00 (m, 2H), 4.12 (q, 2H), 2.30 (m, 1H), 2.07–1.93 (m, 4H), 1.64–1.49 (m, 4H), 1.47–1.20 (m, 17H).

Example 8

Synthesis of Ethyl 2-(7,7,8,8,8-Pentafluorooctyl)-9-decenoate

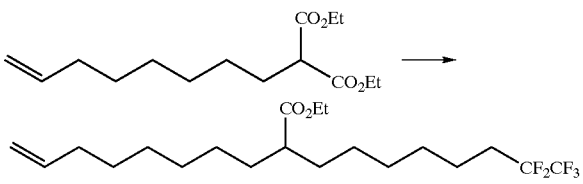

Starting with the diethyl 2-(7-octenyl)malonate prepared in Example 5 and the 1-iodo-7,7,8,8,8-pentafluorooctane prepared in Example 4, the same procedure as shown in Example 5 was repeated to give ethyl 2-(7,7,8,8,8-pentafluorooctyl)-9-decenoate.

$^1$H-NMR (300 MHz, CDCl$_3$): δ 5.78 (m, 1H), 5.02–4.88 (m, 2H), 4.10 (q, 2H), 2.27 (m, 1H), 2.06–1.91 (m, 4H), 1.63–1.18 (m, 23H).

Example 9

Synthesis of Ethyl 2-(5,5,6,6,6-Pentafluorohexyl)-8-nonenoate (Step 1)

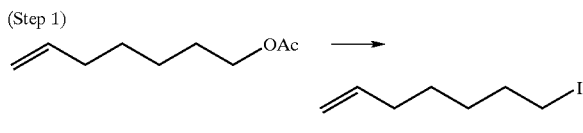

A solution of sodium hydroxide (13.67 g, 341.83 mmol) in water (100 ml) was added to a solution of 6-heptenyl acetate (17.8 g, 113.94 mmol) in methanol (300 ml), followed by stirring for 2 hours at room temperature. The reaction mixture was neutralized with 10% hydrochloric acid and concentrated under reduced pressure. Water was added to the residue, which was then extracted twice with ethyl acetate. The combined organic layers were washed with water and saturated aqueous sodium chloride, and then dried over anhydrous magnesium sulfate. After distilling off the solvent, the residue was dissolved in dichloromethane (200 ml), and triethylamine (33.57 ml, 240.83 mmol) and methanesulfonyl chloride (8.95 ml, 115.60 mmol) were added dropwise thereto at 0° C., followed by stirring for 1 hour. Water was added to the reaction mixture, which was then extracted twice with dichloromethane. The combined organic layers were washed with water and saturated aqueous sodium chloride, and then dried over anhydrous magnesium sulfate. After distilling off the solvent, the residue was dissolved in acetone (370 ml) and mixed with sodium iodide (43.26 g, 288.64 mmol), followed by heating under reflux for 12 hours. Water was added to this mixture, which was then extracted twice with ether. The combined organic layers were washed with 1% aqueous sodium thiosulfate and saturated aqueous sodium chloride, and then dried over anhydrous magnesium sulfate. After distilling off the solvent, the residue was purified by silica gel column chromatography (eluent: pentane) to give 7-iodo-1-heptene (18 g, Yield 74%).

$^1$H-NMR (300 MHz, CDCl$_3$): δ 5.80 (m, 1H), 5.04–4.94 (m, 2H), 3.19 (t, 2H, J=6.9 Hz), 2.07–2.05 (m, 2H), 1.89–1.78 (m, 2H), 1.50–1.32 (m, 4H).

(Step 2)

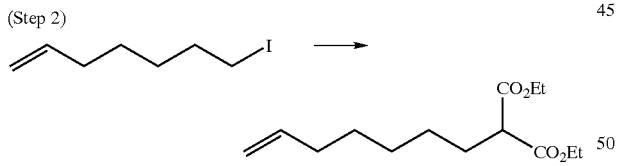

Sodium hydride (60%, 5.78 g, 144.59 mmol) was added to anhydrous tetrahydrofuran (250 ml) and cooled to 0° C. To this mixture, diethyl malonate (25.09 g, 156.64 mmol) was slowly added dropwise, followed by stirring for 1 hour at room temperature. 7-Iodo-1-heptene (27 g, 120.49 mmol) dissolved in anhydrous tetrahydrofuran (50 ml) was then slowly added dropwise to the mixture, followed by stirring for 12 hours at room temperature. Water was added to the reaction mixture, which was then extracted twice with ethyl acetate. The combined organic layers were washed with water and saturated aqueous sodium chloride, and then dried over anhydrous magnesium sulfate. After distilling off the solvent, the residue was purified by silica gel column chromatography (eluent: ethyl acetate/hexane=1/40) to give diethyl 2-(6-heptenyl)malonate (25.8 g, Yield 84%).

$^1$H-NMR (300 MHz, CDCl$_3$): δ 5.80 (m, 1H), 5.02–4.92 (m, 2H), 4.24–4.09 (m, 4H), 3.31 (t, 1H, J=7.5 Hz), 2.07–2.00 (m, 2H), 1.93–1.85 (m, 2H), 1.41–1.18 (m, 12H).

(Step 3)

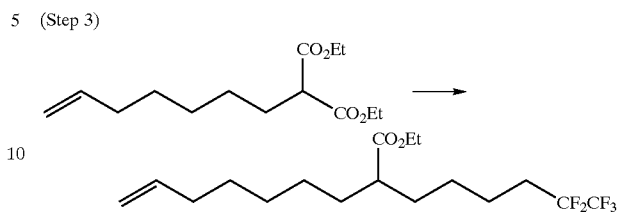

Starting with diethyl 2-(6-heptenyl)malonate and the 1-iodo-5,5,6,6,6-pentafluorohexane prepared in Example 2, the same procedure as shown in Example 5 was repeated to give ethyl 2-(5,5,6,6,6-pentafluorohexyl)-8-nonenoate.

$^1$H-NMR (300 MHz, CDCl$_3$): δ 5.80 (m, 1H), 5.22–4.91 (m, 2H), 4.14 (q, 2H, J=7.2 Hz), 2.39 (m, 1H), 2.10–1.93 (m, 4H), 1.67–0.83 (m, 17H).

Example 10

Synthesis of Ethyl 2-(4,4,5,5,5-Pentafluoropentyl)-8-nonenoate

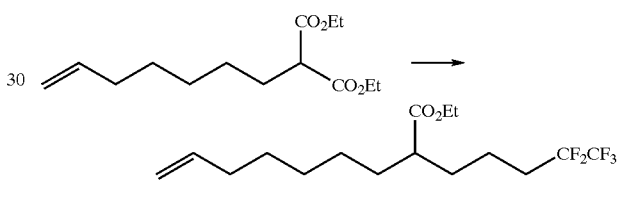

Starting with the diethyl 2-(6-heptenyl)malonate prepared in Example 9 and the 1-iodo-4,4,5,5,5-pentafluoro-pentane prepared in Example 1, the same procedure as shown in Example 5 was repeated to give ethyl 2-(4,4,5,5,5-pentafluoropentyl)-8-nonenoate.

$^1$H-NMR (300 MHz, CDCl$_3$): δ 5.78 (m, 1H), 5.10–4.90 (m, 2H), 4.14 (q, 2H, J=7.3 Hz), 2.31 (m, 1H), 2.15–1.90 (m, 4H), 1.70–1.08 (m, 15H); Mass (ESI): 345 (M+1).

Example 11

Synthesis of Ethyl 2-(6,6,7,7,7-Pentafluoroheptyl)-8-nonenoate

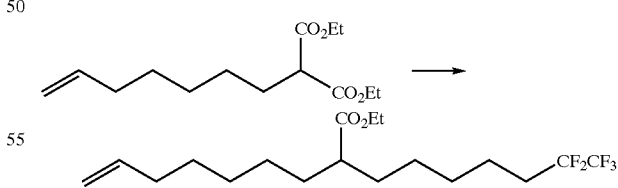

Starting with the diethyl 2-(6-heptenyl)malonate prepared in Example 9 and the 1-iodo-6,6,7,7,7-pentafluoro-heptane prepared in Example 3, the same procedure as shown in Example 5 was repeated to give ethyl 2-(6,6,7,7,7-pentafluoroheptyl)-8-nonenoate.

$^1$H-NMR (300 MHz, CDCl$_3$): δ 5.78 (m, 1H), 5.05–4.85 (m, 2H), 4.13 (q, 2H), 2.31 (m, 1H), 2.08–1.90 (m, 4H), 1.63–1.50 (m, 4H), 1.48–1.15 (m, 15H).

Example 12

Synthesis of Ethyl 2-(7,7,8,8,8-Pentafluorooctyl)-8-nonenoate

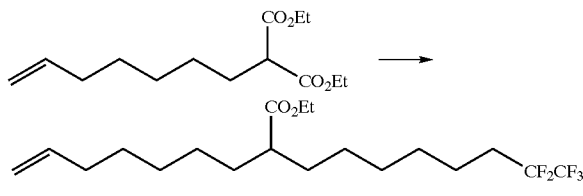

Starting with the diethyl 2-(6-heptenyl)malonate prepared in Example 9 and the 1-iodo-7,7,8,8,8-pentafluoro-octane prepared in Example 4, the same procedure as shown in Example 5 was repeated to give ethyl 2-(7,7,8,8,8-pentafluorooctyl)-8-nonenoate.

$^1$H-NMR (270 MHz, CDCl$_3$): d 5.88–5.71 (m, 1H, olefin-H), 5.03–4.90 (m, 2H, olefin-H), 4.13 (q, J=9 Hz, 2H, COOCH$_2$), 2.30 (m, 1H, CHCOO), 2.10–1.90 (m, 4H, CH$_2$CF$_2$ and allyl-CH$_2$), 1.55–1.22 (m, 21H, alkyl-H and COOCH$_2$CH$_3$).

Example 13

Synthesis of 10-[(3RS,4RS)-3-Ethyl-7-hydroxy-3-(4-hydroxyphenyl)thiochroman-4-yl]-2-(7,7,8,8,8-pentafluorooctyl)-decanoic Acid (Step 1)

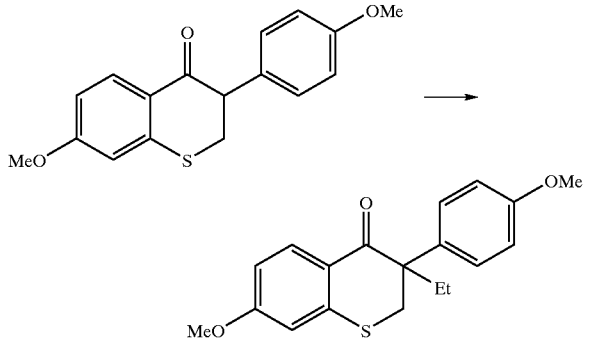

7-Methoxy-3-(4-methoxyphenyl)thiochroman-4-one was synthesized by the method described in WO98/25916 and a portion of this compound (26.73 g, 89.1 mmol) was dissolved in toluene (900 ml), followed by addition of ethyl triflate (34.6 ml, 276 mmol). Potassium tert-butoxide (19.95 g, 178 mmol) was added to this solution at 0° C. and the resulting mixture was stirred for 2 days at room temperature under argon atmosphere. Potassium tert-butoxide (20.0 g, 178 mmol) was further added to the reaction mixture at 0° C., followed by stirring for 1 day. Water was added to the reaction mixture, which was then extracted with ether. The ether layer was washed with saturated aqueous sodium bicarbonate, water and saturated aqueous sodium chloride, and then dried over anhydrous magnesium sulfate. After distilling off the solvent, the residue was purified by silica gel flash column chromatography (eluent: hexane/ethyl acetate=5/1) to give 3-ethyl-7-methoxy-3-(4-methoxyphenyl)thiochroman-4-one (26.12 g, Yield 89%).

$^1$H-NMR (270 MHz, CDCl$_3$): δ 8.15 (d, J=9 Hz, 1H, Ar—H), 7.15 (d, J=9 Hz, 2H, Ar—H), 6.82 (d, J=9 Hz, 2H, Ar—H), 6.67 (dd, J=9, 2 Hz, 1H, Ar—H), 6.54 (d, J=2 Hz, 1H, Ar—H), 3.77 (s, 3H, OCH$_3$), 3.76 (s, 3H, OCH$_3$), 3.58 (d, J=14 Hz, 1H, C2-H), 3.41 (d, J=14 Hz, 1H, C2-H), 2.04 (q, J=7 Hz, 2H, CH$_2$CH$_3$), 0.82 (t, 3H, J=7 Hz, 2H, CH$_2$CH$_3$).

(Step 2)

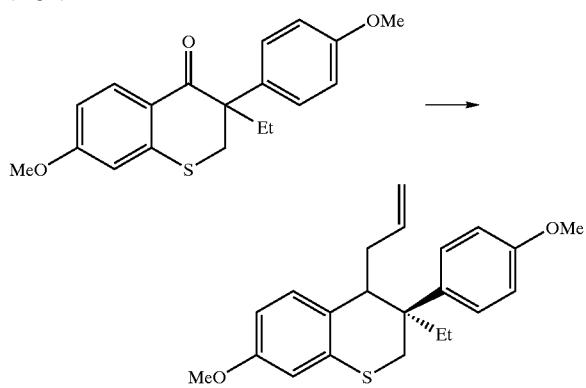

A solution of 3-ethyl-7-methoxy-3-(4-methoxyphenyl)-thiochroman-4-one (13.7 g, 41.8 mmol) in anhydrous tetrahydrofuran (100 ml) was added dropwise to a solution of lithium aluminum hydride (950 mg, 25 mmol) in anhydrous tetrahydrofuran (100 ml) at −78° C. under argon atmosphere, and the resulting mixture was warmed to −20° C. over 1 hour. Ethyl acetate, methanol and 2N aqueous hydrochloric acid were added sequentially to the reaction mixture, which was then filtered through cellite. After extraction with ethyl acetate, the organic layer was washed with saturated aqueous sodium bicarbonate, water and saturated aqueous sodium chloride, and then dried over anhydrous magnesium sulfate. After distilling off the solvent, the resulting residue (13.10 g) was dissolved in 1,2-dichloroethane (360 ml) and then mixed with allyltrimethylsilane (12.47 ml, 78.75 mmol). Zinc iodide (15.08 g, 47.27 mmol) was added to this solution at 0° C. under argon atmosphere, and the resulting mixture was stirred for 4 hours at 40° C. Water and dilute hydrochloric acid were added sequentially to this mixture, which was then extracted with ethyl acetate. The organic layer was washed with saturated aqueous sodium bicarbonate, water and saturated aqueous sodium chloride, and then dried over anhydrous magnesium sulfate. After distilling off the solvent, the residue was purified by silica gel flash column chromatography (eluent: hexane/ethyl acetate=20/1) to give (3RS,4RS)-3-ethyl-7-methoxy-3-(4-methoxyphenyl)-4-(2-propenyl)thiochroman (8.73 g, Yield 62% for 2 steps).

$^1$H-NMR (270 MHz, CDCl$_3$): d 7.25 (d, J=9 Hz, 2H, Ar—H), 6.92 (d, J=9 Hz, 2H, Ar—H), 6.90 (d, J=9 Hz, 1H, Ar—H), 6.71 (d, J=2 Hz, 1H, Ar—H), 6.55 (dd, J=9, 2 Hz,

1H, Ar—H), 5.55 (m, 1H, olefin-H), 4.83 (d, J=10 Hz, 1H, olefin-H), 4.65 (d, J=17 Hz, 1H, olefin-H), 3.83 (s, 3H, OCH$_3$), 3.77 (s, 3H, OCH$_3$), 3.48 (d, J=12 Hz, 1H, C2-H), 3.23 (d, J=12 Hz, 1H, C2-H), 2.80 (m, 1H, C4-H), 1.90 (m, 2H, allylic-CH$_2$), 1.69 and 1.46 (each m, each 1H, CH$_2$CH$_3$), 0.51 (t, 3H, J=7 Hz, 2H, C3-CH$_2$CH$_3$).

(Step 3)

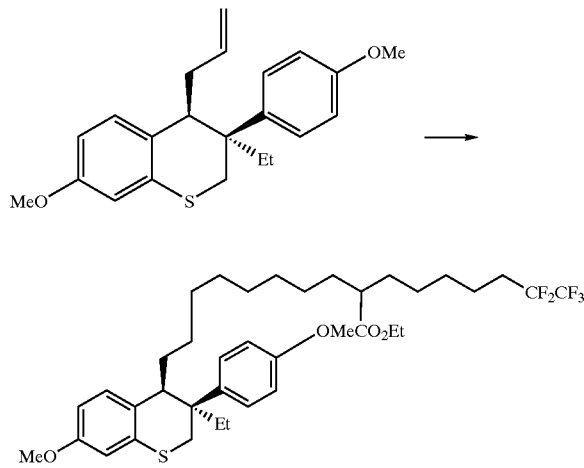

resulting mixture followed by stirring for 12 hours at room temperature under hydrogen atmosphere. The catalyst was removed by filtration and the solvent was distilled off under reduced pressure. The residue was dissolved again in ethyl acetate (15 ml), and palladium carbon (340 mg) was added to the resulting mixture followed by stirring for 20 hours at room temperature under hydrogen atmosphere. The catalyst was removed by filtration and the solvent was distilled off under reduced pressure. The residue was purified by silica gel flash column chromatography (eluent: hexane/ethyl acetate=5/1) to give ethyl 10-[(3RS,4RS)-3-ethyl-7-methoxy-3-(4-methoxyphenyl)thiochroman-4-yl]-2-(7,7,8,8,8-pentafluorooctyl)decanoate (1.05 g, Yield 91%).

$^1$H-NMR (270 MHz, CDCl$_3$): d 7.25 (d, J=9 Hz, 2H, Ar—H), 6.92 (d, J=9 Hz, 1H, Ar—H), 6.90 (d, J=9 Hz, 2H, Ar—H), 6.71 (d, J=2 Hz, 1H, Ar—H), 6.56 (dd, J=9, 2 Hz, 1H, Ar—H), 4.12 (q, J=6 Hz, 2H, CO$_2$CH$_2$CH$_3$), 3.82 (s, 3H, OCH$_3$), 3.77 (s, 3H, OCH$_3$), 3.48 (d, J=12 Hz, 1H, C2-H), 3.23 (d, J=12 Hz, 1H, C2-H), 2.79 (m, 1H, C4-H), 2.28 (m, 1H, CHCO$_2$Et), 2.10–1.95 (m, 2H, CH$_2$CF$_2$), 1.70–0.90 (m, 31H, C3-CH$_2$CH$_3$, CO$_2$CH$_2$CH$_3$ and alkyl-H), 0.48 (t, 3H, J=7 Hz, 2H, C3-CH$_2$CH$_3$).

(Step 4)

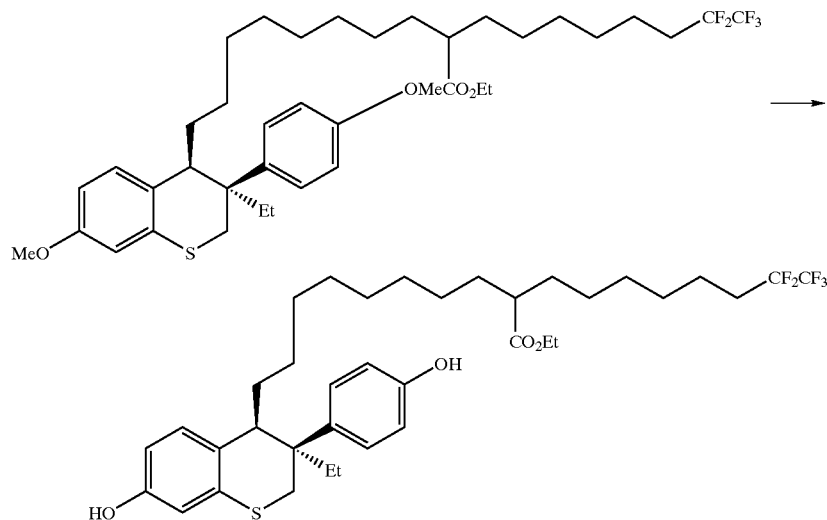

The ethyl 2-(7,7,8,8,8-pentafluorooctyl)-8-nonenoate prepared in Example 12 (1.67 g, 4.32 mmol) and benzylidene-bis(tricyclohexylphosphine)dichlororuthenium (90 mg, 0.11 mmol) were added to a solution of (3RS,4RS)-3-ethyl-7-methoxy-3-(4-methoxyphenyl)-4-(2-propenyl)thiochroman (740 mg, 2.18 mmol) in dichloromethane (20 ml), followed by heating under reflux for 7.5 hours under argon atmosphere. After distilling off the solvent under reduced pressure, the residue was purified by silica gel flash column chromatography (eluent: hexane/ethyl acetate=10/1) to give the desired olefin (1.15 g) as a mixture of cis- and trans-forms. This mixture was dissolved in ethyl acetate (15 ml), and 10% palladium carbon (346 mg) was added to the A solution of boron tribromide in dichloromethane (1.0 M, 8.82 ml, 8.82 mmol) was added dropwise to a solution of ethyl 10-[(3RS,4RS)-3-ethyl-7-methoxy-3-(4-methoxyphenyl)thiochroman-4-yl]-2-(7,7,8,8,8-pentafluorooctyl)decanoate (1.05 g, 1.47 mmol) in dichloromethane (15 ml) at −78° C. under argon atmosphere. The reaction mixture was warmed with stirring up to 10° C. over 3 hours. Water was added to the reaction mixture, which was then extracted with ethyl acetate. The organic layer was washed with water and saturated aqueous sodium chloride, and then dried over anhydrous magnesium sulfate. After distilling off the solvent, the resulting residue was dissolved in ethanol (5 ml) and mixed with concentrated sulfuric acid (1 drop), followed by heating under reflux for 12 hours.

Water was added to the reaction mixture, which was then extracted with ethyl acetate. The organic layer was washed with saturated aqueous sodium chloride, and then dried over anhydrous magnesium sulfate. After distilling off the solvent, the residue was purified by silica gel flash column chromatography (eluent: hexane/ethyl acetate=2/1) to give ethyl 10-[(3RS,4RS)-3-ethyl-7-hydroxy-3-(4-hydroxyphenyl)thiochroman-4-yl]-2-(7,7,8,8,8-pentafluorooctyl)decanoate (550 mg, Yield 55%).

$^1$H-NMR (270 MHz, CDCl$_3$): d 7.22 (d, J=8 Hz, 2H, Ar—H), 6.85 (d, J=8 Hz, 1H, Ar—H), 6.84 (d, J=8 Hz, 2H, Ar—H), 6.66 (d, J=2 Hz, 1H, Ar—H), 6.47 (dd, J=8, 2 Hz, 1H, Ar—H), 6.21 (br s, 1H, OH), 5.30 (br s, 1H, OH), 4.17 (q, J=7 Hz, 2H, CO$_2$CH$_2$CH$_3$), 3.46 (d, J=12 Hz, 1H, C2-H), 3.08 (d, J=12 Hz, 1H, C2-H), 2.71 (m, 1H, C4-H), 2.34 (m, 1H, CHCO$_2$Et), 2.10–1.90 (m, 2H, CH$_2$CF$_2$), 1.85–0.80 (m, 31H, C3-CH$_2$CH$_3$, CO$_2$CH$_2$CH$_3$ and alkyl-H), 0.50 (t, 3H, J=7 Hz, 2H, C3-CH$_2$CH$_3$).

(Step 5)

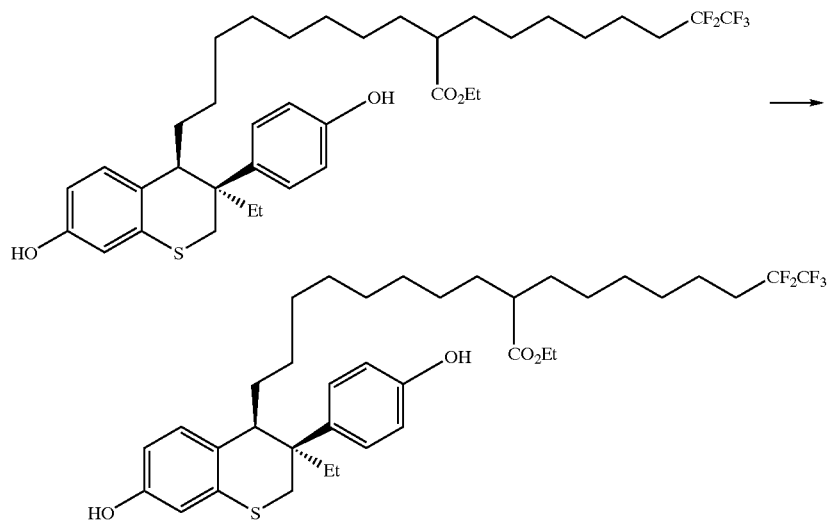

A solution of sodium hydroxide (325 mg) in water (4 ml) was added to a solution of ethyl 10-[(3RS,4RS)-3-ethyl-7-hydroxy-3-(4-hydroxyphenyl)thiochroman-4-yl]-2-(7,7,8,8,8-pentafluorooctyl)decanoate (558 mg, 0.81 mmol) in ethanol (8 ml). The reaction mixture was heated under reflux for 12 hours. Dilute hydrochloric acid was added to the reaction mixture, which was then extracted with ethyl acetate. The organic layer was washed with water and saturated aqueous sodium chloride, and then dried over anhydrous magnesium sulfate. After distilling off the solvent, the residue was purified by silica gel flash column chromatography (eluent: hexane/ethyl acetate=2/1) to give 10-[(3RS,4RS)-3-ethyl-7-hydroxy-3-(4-hydroxyphenyl)thiochroman-4-yl]-2-(7,7,8,8,8-pentafluoro-octyl)decanoic acid (480 mg, Yield 89%).

$^1$H-NMR (270 MHz, CDCl$_3$): d 7.17 (d, J=9 Hz, 2H, Ar—H), 6.86 (d, J=8 Hz, 1H, Ar—H), 6.83 (d, J=9 Hz, 2H, Ar—H), 6.66 (d, J=2 Hz, 1H, Ar—H), 6.48 (dd, J=8, 2 Hz, 1H, Ar—H), 3.46 (d, J=12 Hz, 1H, C2-H), 3.08 (d, J=12 Hz, 1H, C2-H), 2.72 (br s, 1H, C4-H), 2.34 (m, 1H, CHCO$_2$Et), 2.10–1.85 (m, 2H, CH$_2$CF$_2$), 1.70–0.90 (m, 28H, C3-CH$_2$CH$_3$ and alkyl-H), 0.49 (t, 3H, J=7 Hz, 2H, C3-CH$_2$CH$_3$).

Example 14

Synthesis of 10-[(3RS,4RS)-3-Ethyl-7-hydroxy-3-(4-hydroxyphenyl)thiochroman-4-yl]-2-(6,6,7,7,7-pentafluoroheptyl)-decanoic Acid

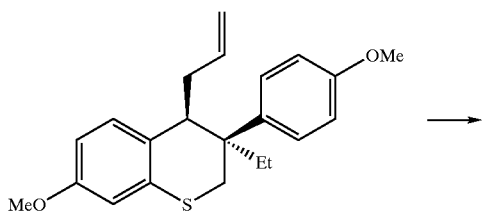

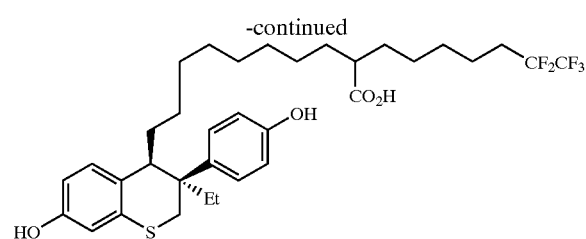

Starting with the allyl compound prepared in Example 13 and the ethyl 2-(6,6,7,7,7-pentafluoroheptyl)-8-nonenoate prepared in Example 11, the same procedure as shown in Example 13 was repeated to give 10-[(3RS,4RS)-3-ethyl-7-hydroxy-3-(4-hydroxyphenyl)thiochroman-4-yl]-2-(6,6,7,7,7-pentafluoroheptyl)decanoic acid.

$^1$H-NMR (300 MHz, CDCl$_3$): δ 7.16 (d, 2H, J=8.7 Hz), 6.89–6.81 (m, 3H), 6.66 (s, 1H), 6.47 (m, 1H), 3.47 (d, 1H, J=11.9 Hz), 3.08 (d, 1H, J=11.9 Hz), 2.82 (m, 1H), 2.36 (m, 1H), 2.10–1.90 (m, 2H), 1.70–0.95 (m, 26H), 0.50 (t, 3H, J=7.3 Hz).

Example 15

Synthesis of 10-[(3RS,4RS)-3-Ethyl-7-hydroxy-3-(4-hydroxyphenyl)thiochroman-4-yl]-2-(5,5,6,6,6-pentafluorohexyl)-decanoic Acid

Example 16

Synthesis of 10-[(3RS,4RS)-3-Ethyl-7-hydroxy-3-(4-hydroxyphenyl)thiochroman-4-yl]-2-(4,4,5,5,5-pentafluoropentyl)-decanoic Acid

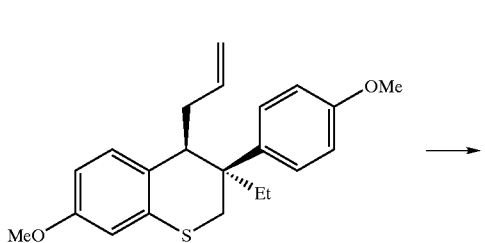

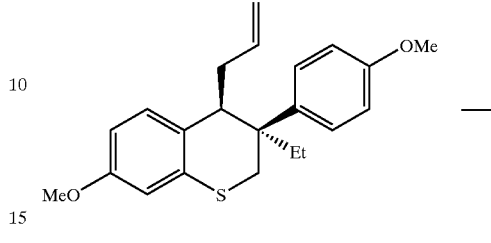

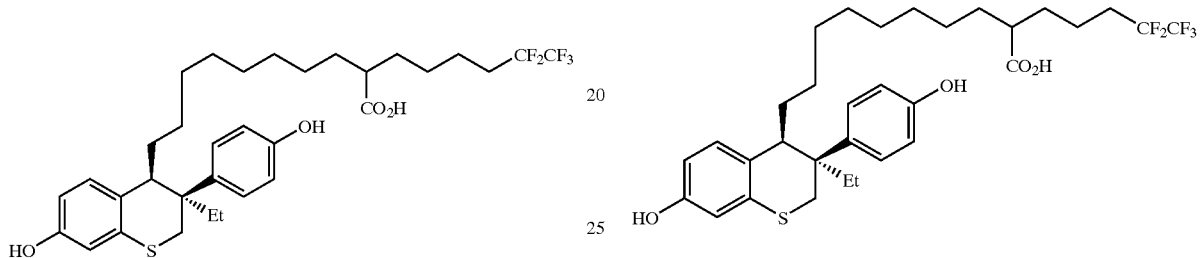

Starting with the allyl compound prepared in Example 13 and the ethyl 2-(5,5,6,6,6-pentafluorohexyl)-8-nonenoate prepared in Example 9, the same procedure as shown in Example 13 was repeated to give 10-[(3RS,4RS)-3-ethyl-7-hydroxy-3-(4-hydroxyphenyl)thiochroman-4-yl]-2-(5,5,6,6,6-pentafluorohexyl)decanoic acid.

$^1$H-NMR (300 MHz, CDCl$_3$): δ 7.18 (d, 2H, J=8.7 Hz), 6.88–6.81 (m, 3H), 6.65 (d, 1H, J=2.3 Hz), 6.47 (dd, 1H, J=8.3 Hz, J=2.6 Hz), 3.46 (d, 1H, J=11.7 Hz), 3.09 (d, 1H, J=11.7 Hz), 2.74 (m, 1H), 2.40 (m, 1H), 2.10–1.93 (m, 4H), 1.47–0.98 (m, 22H), 0.50 (t, 3H, J=7.4 Hz).

Starting with the allyl compound prepared in Example 13 and the ethyl 2-(4,4,5,5,5-pentafluoropentyl)-8-nonenoate prepared in Example 10, the same procedure as shown in Example 13 was repeated to give 10-[(3RS,4RS)-3-ethyl-7-hydroxy-3-(4-hydroxyphenyl)thiochroman-4-yl]-2-(4,4,5,5,5-pentafluoropentyl)decanoic acid.

$^1$H-NMR (300 MHz, CDCl$_3$): δ 7.15 (d, 2H, J=9.0 Hz), 6.92–6.80 (m, 3H), 6.64 (d, 1H, J=2.6 Hz), 6.47 (dd, 1H, J$_1$=8.3 Hz, J$_2$=2.6 Hz), 3.44 (d, 1H, J=11.7 Hz), 3.07 (d, 1H, J=11.7 Hz), 2.71 (bs, 1H), 2.37 (m, 1H), 2.01–1.98 (m, 2H), 1.75–1.49 (m, 6H), 1.40–1.38 (m, 2H), 1.26–0.93 (m, 14H), 0.47 (t, 3H, J=7.2 Hz). Mass (ESI): 617 (M+1).

Example 17

Synthesis of 11-[(3RS,4RS)-3-Ethyl-7-hydroxy-3-(4-hydroxyphenyl)thiochroman-4-yl]-2-(7,7,8,8,8-pentafluorooctyl)-undecanoic Acid

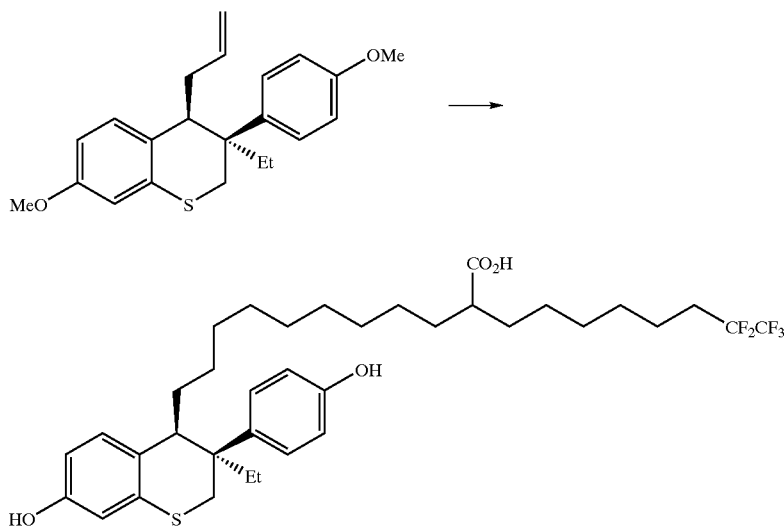

Starting with the allyl compound prepared in Example 13 and the ethyl 2-(7,7,8,8,8-pentafluorooctyl)-9-decenoate prepared in Example 8, the same procedure as shown in Example 13 was repeated to give 11-[(3RS,4RS)-3-ethyl-7-hydroxy-3-(4-hydroxyphenyl)thiochroman-4-yl]-2-(7,7,8,8,8-pentafluorooctyl)undecanoic acid.

$^1$H-NMR (270 MHz, CDCl$_3$) d: 7.16 (d, J=8.6 Hz, 2H), 6.83 (t, J=9.6 Hz, 3H), 6.64 (d, J=2.3 Hz, 2H), 6.46 (dd, J=2.3, 8.0 Hz, 1H), 3.43 (d, J=11.9 Hz, 1H), 3.07 (d, J=11.9 Hz, 1H), 2.72 (s, 1H), 2.52–2.35 (m, 1H), 2.10–0.90 (m, 24H), 0.47 (t, J=7.6 Hz, 3H).

Example 18

Synthesis of 11-[(3RS,4RS)-3-Ethyl-7-hydroxy-3-(4-hydroxyphenyl)thiochroman-4-yl]-2-(6,6,7,7,7-pentafluoroheptyl)-undecanoic Acid

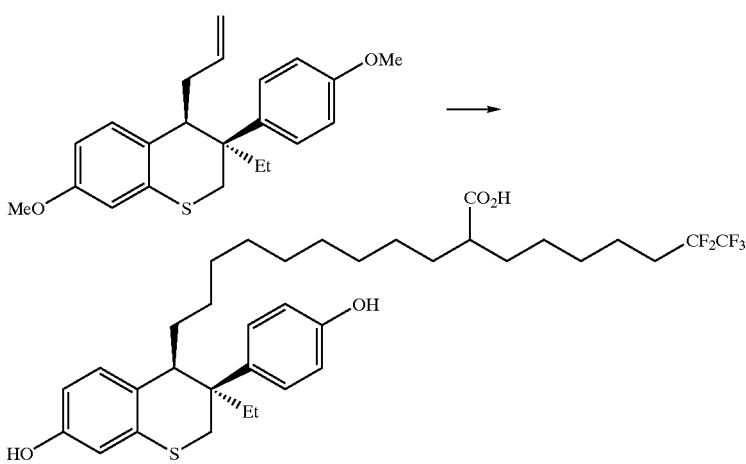

Starting with the allyl compound prepared in Example 13 and the ethyl 2-(6,6,7,7,7-pentafluoroheptyl)-9-decenoate prepared in Example 7, the same procedure as shown in Example 13 was repeated to give 11-[(3RS,4RS)-3-ethyl-7-hydroxy-3-(4-hydroxyphenyl)thiochroman-4-yl]-2-(6,6,7,7,7-pentafluoroheptyl)undecanoic acid.

$^1$H-NMR (270 MHz, CD$_3$OD): d 7.18 (d, J=8 Hz, 2H, Ar—H), 6.85 (d, J=8 Hz, 1H, Ar—H), 6.79 (d, J=8 Hz, 2H, Ar—H), 6.56 (d, J=2 Hz, 1H, Ar—H), 6.43 (dd, J=8, 2 Hz, 1H, Ar—H), 3.43 (d, J=12 Hz, 1H, C2-H), 3.10 (d, J=12 Hz, 1H, C2-H), 2.76 (br s, 1H, C4-H), 2.38–2.21 (m, 1H, C HCO$_2$H), 2.29–1.98 (m, 2H, CH$_2$CF$_2$), 1.69–0.90 (m, 28H, C3-CH$_2$CH$_3$ and alkyl-H), 0.48 (t, 3H, J=7 Hz, C3-CH$_2$C H$_3$).

Example 19

Synthesis of 11-[(3RS,4RS)-3-Ethyl-7-hydroxy-3-(4-hydroxyphenyl)thiochroman-4-yl]-2-(5,5,6,6,6-pentafluorohexyl)-undecanoic Acid

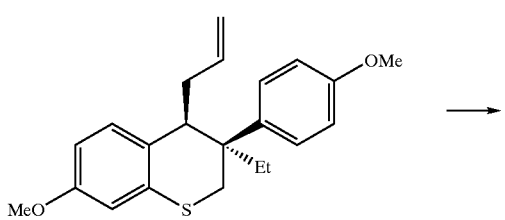

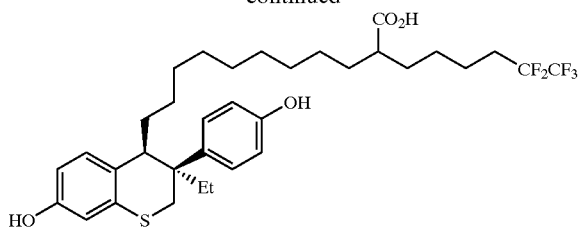

Starting with the allyl compound prepared in Example 13 and the ethyl 2-(5,5,6,6,6-pentafluorohexyl)-9-decenoate prepared in Example 5, the same procedure as shown in Example 13 was repeated to give 11-[(3RS,4RS)-3-ethyl-7-hydroxy-3-(4-hydroxyphenyl)thiochroman-4-yl]-2-(5,5,6,6,6-pentafluorohexyl)undecanoic acid.

$^1$H-NMR (300 MHz, CDCl$_3$): δ 7.15 (d, 2H, J=9.9 Hz), 6.89–6.80 (m, 3H), 6.55 (d, 1H, J=2.7 Hz), 6.40 (dd, 1H, J$_1$=8.3 Hz, J$_2$=2.7 Hz), 3.45 (d, 1H, J=11.9 Hz), 3.09 (d, 1H, J=11.9 Hz), 2.72 (m, 1H), 2.32 (m, 1H), 2.03–2.01 (m, 2H), 1.70–0.90 (m, 26H), 0.50 (t, 3H, J=7.4 Hz). Mass (ESI): 645 (M+1).

Example 20

Synthesis of 11-[(3RS,4RS)-3-Ethyl-7-hydroxy-3-(4-hydroxyphenyl)thiochroman-4-yl]-2-(4,4,5,5,5-pentafluoropentyl)-undecanoic Acid

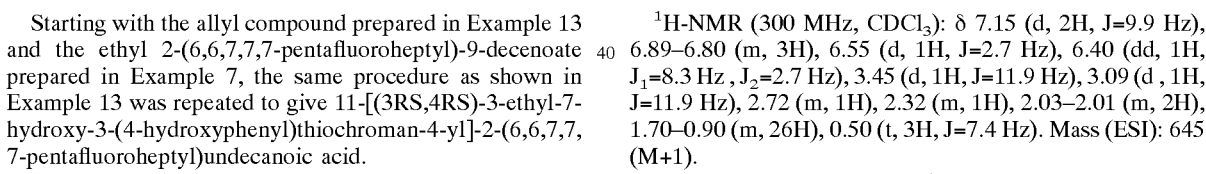

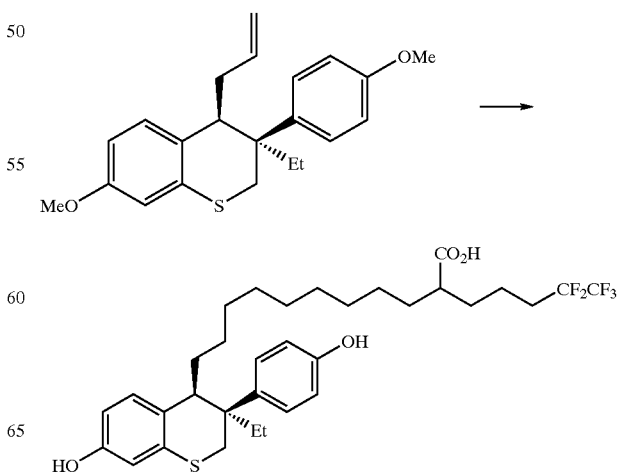

Starting with the allyl compound prepared in Example 13 and the ethyl 2-(4,4,5,5,5-pentafluoropentyl)-9-decenoate prepared in Example 6, the same procedure as shown in Example 13 was repeated to give 11-[(3RS,4RS)-3-ethyl-7-hydroxy-3-(4-hydroxyphenyl)thiochroman-4-yl]-2-(4,4,5,5,5-pentafluoropentyl)undecanoic acid.

¹H-NMR (300 MHz, CDCl₃): d 7.18 (d, J=9 Hz, 2H, Ar—H), 6.87 (d, J=8 Hz, 1H, Ar—H), 6.84 (d, J=9 Hz, 2H, Ar—H), 6.66 (d, J=2 Hz, 1H, Ar—H), 6.49 (dd, J=8, 2 Hz, 1H, Ar—H), 3.46 (d, J=12 Hz, 1H, C2-H), 3.09 (d, J=12 Hz, 1H, C2-H), 2.74 (m, 1H, C4-H), 2.42 (m, 1H, CHCO₂H), 2.12–1.94 (m, 2H, CH₂CF₂), 1.78–1.00 (m, 24H, C3-CH₂CH₃ and alkyl-H), 0.49 (t, 3H, J=7 Hz, C3-CH₂CH₃).

Example 21

Synthesis of 11-[(3RS,4RS)-3-Ethyl-7-hydroxy-3-(4-hydroxyphenyl)chroman-4-yl]-2-(7,7,8,8,8-pentafluorooctyl)-undecanoic Acid (Step 1)

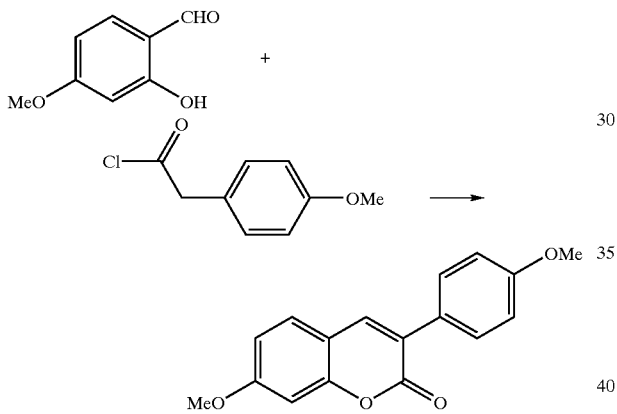

A suspension of 2-hydroxy-4-methoxybenzaldehyde (6.10 g), 4-methoxyphenylacetylchloride (11.1 g) and potassium carbonate (20 g) in acetone (400 ml) was heated under reflux for 2 hours. The reaction mixture was evaporated to remove the solvent, followed by addition of water. The resulting precipitates were collected by filtration and dried under reduced pressure to give 7-methoxy-3-(4-methoxyphenyl)-chromen-2-one (10.1 g, Yield 89%).

¹H-NMR (270 MHz, CDCl₃): d 7.71 (s, 1H, Ar—H), 7.65 (d, 2H, J=8.9 Hz, Ar—H), 7.42 (d, 1H, J=8.9 Hz, Ar—H), 6.97 (d, 2H, J=8.9 Hz, Ar—H), 6.8–6.9 (m, 2H, Ar—H), 3.88 (s, 3H, MeO), 3.85 (s, 3H, MeO).

(Step 2)

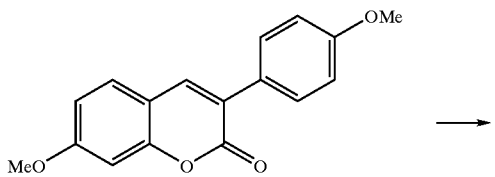

-continued

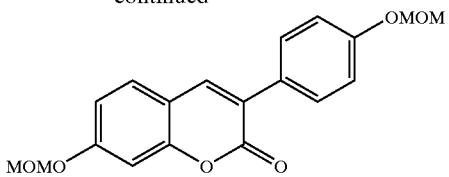

7-Methoxy-3-(4-methoxyphenyl)-chromen-2-one (21.8 g) was mixed with pyridine hydrochloride (80 g) and stirred for 1 hour at a temperature of 190° C. to 200° C. Water was added to the reaction mixture and the resulting precipitates were collected by filtration and dried under reduced pressure to give 7-hydroxy-3-(4-hydroxyphenyl)-chromen-2-one (19.6 g, Yield 100%). Diisopropylethylamine (35 ml) in dimethylformamide (70 ml) and methoxymethyl chloride (10.4 ml) were added to a solution of 7-hydroxy-3-(4-hydroxyphenyl)-chromen-2-one thus prepared (8.74 g) followed by stirring for 2 hours at 80° C. After cooling, water was added to the reaction mixture and the resulting precipitates were collected by filtration and dried under reduced pressure to give 7-methoxymethoxy-3-(4-methoxymethoxyphenyl)chromen-2-one (8.67 g, Yield 74%).

¹H-NMR (270 MHz, CDCl₃): d 7.71 (s, 1H, Ar—H), 7.64 (d, 2H, J=8.9 Hz, Ar—H), 7.43 (d, 1H, J=8.3 Hz, Ar—H), 7.10 (d, 2H, J=8.9 Hz, Ar—H), 6.9–7.1 (m, 2H, Ar—H), 5.24 (s, 2H, OCH₂OMe), 5.22 (s, 2H, OCH₂OMe), 3.50 (s, 3H, MeO), 3.49 (s, 3H, MeO).

(Step 3)

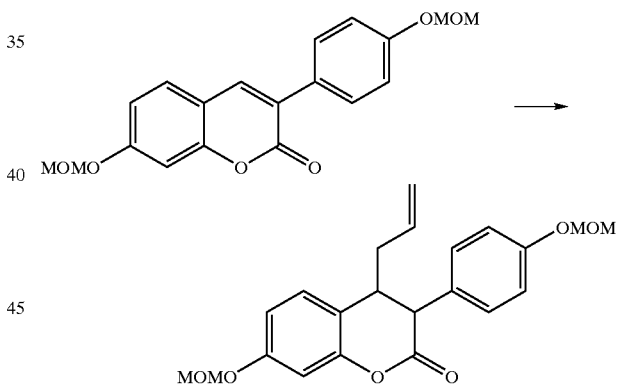

TBAF·n-H₂O (6 g) was azeotroped with toluene and ethanol (20 ml each) under reduced pressure to remove water and then concentrated twice with toluene (20 ml) under reduced pressure. The resulting light-yellow oil was dried using a vacuum pump to prepare anhydrous TBAF. A solution of this anhydrous TBAF in dry dimethylformamide (80 ml) was added to a suspension of 7-methoxymethoxy-3-(4-methoxymethoxyphenyl)chromen-2-one (14.8 g) in dry dimethylformamide (80 ml). To this suspension, a solution of HMPA (vacuum distilled while drying over calcium hydride, 27.1 ml) and allyltrimethylsilane (24.7 ml) in dry dimethylformamide (80 ml) was added dropwise at room temperature over 15 minutes. The resulting red reaction mixture was stirred for 2 hours at room temperature and quenched with 1N hydrochloric acid (100 ml) in methanol (200 ml) on ice. The reaction mixture was extracted three times with ethyl acetate. The combined organic layers were washed three times with water and dried over magnesium sulfate. After concentration under reduced pressure, the resulting crude product was purified by silica gel column chromatography (Wakogel C-200, eluent: hexane/ethyl acetate=10/1→9/1) to give 7-methoxymethoxy-3-(4-methoxymethoxyphenyl)-4-(2-propenyl)chroman-2-one (14.1 g, Yield 85.0%) as a yellow oil.

¹H-NMR (270 MHz, CDCl₃): d 7.23 (d, 1H, J=8.6 Hz, Ar—H), 7.0–7.1 (m, 3H, Ar—H), 6.90 (d, 1H, 8.6 Hz, Ar—H), 6.7–6.9 (m, 2H, Ar—H), 5.5–5.9 (m, 1H, vinyl-H), 5.10, 5.15, 5.18 (each s, 4H, OCH₂OMe), 4.8–5.2 (m, 2H, vinyl-H), 4.14 (d, 0.4H, J=5.6 Hz, C3-H), 4.03 (d, 0.6H, J=3.3 Hz, C3-H), 3.50, 3.48, 3.43 (each s, 6H, OCH₃), 3.19 (td, 0.6H, J=6.9, 3.3 Hz, C4-H), 3.05–3.15 (m, 0.4H, C4-H), 2.1–2.5 (m, 2H, allylic-H).

(Step 4)

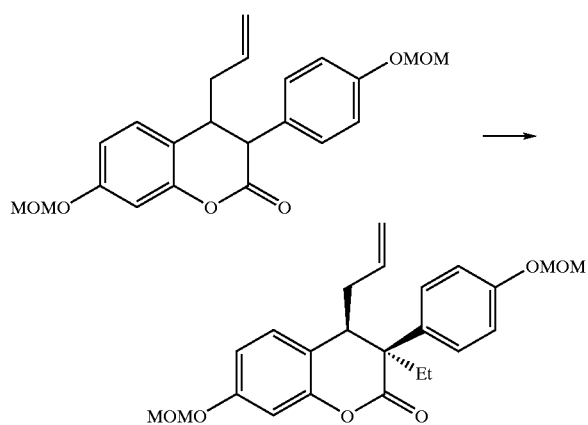

A 1M solution of lithium hexamethyl-disilazide in tetrahydrofuran (86.2 ml) was added dropwise to a solution of 7-methoxymethoxy-3-(4-methoxymethoxyphenyl)-4-(2-propenyl)chroman-2-one (16.57 g) in dry tetrahydrofuran (86.2 ml) at −78° C. over 30 minutes under nitrogen atmosphere, followed by stirring for 20 minutes at 0° C. After the reaction mixture was cooled to −78° C., ethyl triflate (21.6 ml) was added dropwise thereto over 20 minutes and the resulting mixture was warmed to −30° C. over 3 hours, followed by addition of pyridine (13.9 ml). This mixture was stirred for 15 minutes at −30° C., cooled to −78° C., and further mixed with saturated aqueous ammonium chloride (100 ml) and water (50 ml). After extraction with ethyl acetate, the organic layer was washed with 0.05 N aqueous hydrochloric acid and saturated aqueous sodium chloride, and then dried over anhydrous sodium sulfate. After concentration under reduced pressure, the resulting oil was purified by flash column chromatography (silica gel: Merck Kieselgel 60, eluent: hexane/ethyl acetate=5/1→4/1) to give (3RS,4RS)-3-ethyl-7-methoxymethoxy-3-(4-methoxymethoxyphenyl)-4-(2-propenyl)chroman-2-one (14.98 g, Yield 84.3%) as a white solid.

¹H-NMR (270 MHz, CDCl₃): d 7.54 (d, 2H, J=8.9 Hz, Ar—H), 7.05 (d, 2H, J=8.9 Hz, Ar—H), 7.00 (d, 1H, J=8.9 Hz, Ar—H), 6.7–6.8 (m, 2H, Ar—H), 5.4–5.6 (m, 1H, vinyl-H), 5.17, 5.20 (each s, 4H, OCH₂OMe), 4.89 (d, 1H, J=10.2 Hz, vinyl-H), 4.73 (dd, 1H, J=17.2, 1.7 Hz, vinyl-H), 3.502, 3.498 (each s, 6H, OCH₃), 2.91 (dd, 1H, J=9.9, 3.6 Hz, C4-H), 1.8–2.2 (m, 4H, allylic-H and C<u>H</u>₂Me), 0.70 (t, 3H, J=7.3 Hz, CH₂C<u>H</u>₃).

(Step 5)

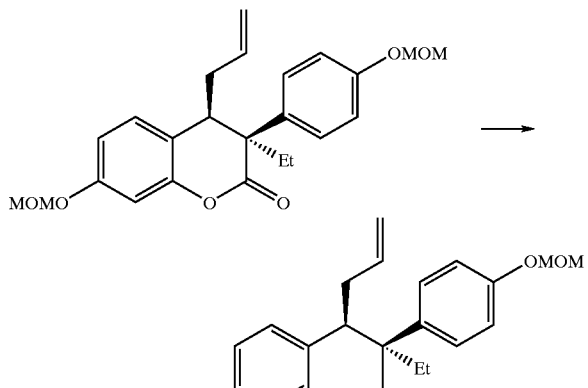

A solution of (3RS,4RS)-3-ethyl-7-methoxymethoxy-3-(4-methoxymethoxyphenyl)-4-(2-propenyl)chroman-2-one (9.4 g) in dry tetrahydrofuran (50 ml) was added dropwise to an ice-cold suspension of lithium aluminum hydride (2.2 g) in dry tetrahydrofuran (50 ml) over 25 minutes under nitrogen atmosphere, and the reaction mixture was then stirred on ice for 1 hour and 15 minutes. Ethyl acetate (30 ml) and saturated aqueous ammonium chloride (30 ml) were added to stop the reaction, followed by stirring for 1 hour at room temperature. The reaction mixture was filtered through cellite and the resulting filtrate was extracted twice with ethyl acetate. The combined organic layers were washed with saturated aqueous ammonium chloride, dried over magnesium sulfate, and then concentrated under reduced pressure to give (2RS,3RS)-2-ethyl-3-(2-hydroxy-4-methoxymethoxyphenyl)-2-(4-methoxymethoxyphenyl)-5-hexenol (9.5 g, quantitative) as a crude product, which was then used for the subsequent reaction without further purification.

¹H-NMR (270 MHz, CDCl₃): d 7.4–7.5 (bs, 1H, Ar—OH), 6.94 (d, 2H, J=9.2 Hz, Ar—H), 6.86 (d, 2H, J=9.2 Hz, Ar—H), 6.57 (d, 1H, J=2.6 Hz, Ar—H), 6.31 (dd, 1H, J=8.9, 2.6 Hz, Ar—H), 5.91 (d, 1H, J=8.9 Hz, Ar—H), 5.3–5.5 (m, 1H, vinyl-H), 5.17, 5.20 (each d, 2H, J=6.9 Hz, OCH₂OMe), 5.10, 5.13 (each d, 2H, J=6.9 Hz, OCH₂OMe), 4.84 (dd, 1H, J=17.2, 2.0 Hz, vinyl-H), 4.75 (dd, 1H, J=9.9, 2.0 Hz, vinyl-H), 3.7–3.9 (m, 1H, C1-H), 3.6–3.7 (m, 1H, C1-H), 3.51, 3.48 (each s, 6H, OCH₃), 3.31 (dd, 1H, J=11.5, 3.3 Hz, C3-H), 2.7–2.9 (bs, 1H, C1-OH), 2.6–2.7 (m, 1H, C4-H), 2.3–2.5 (m, 1H, C<u>H</u>₂Me), 1.9–2.1 (m, 2H, C4-H and C<u>H</u>₂Me), 0.79 (t, 3H, J=7.3 Hz, CH₂C<u>H</u>₃).

(Step 6)

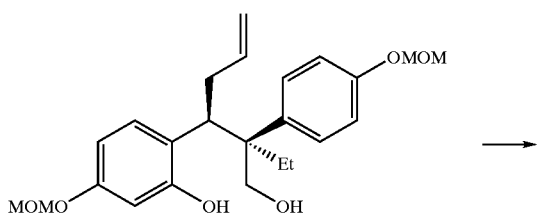

-continued

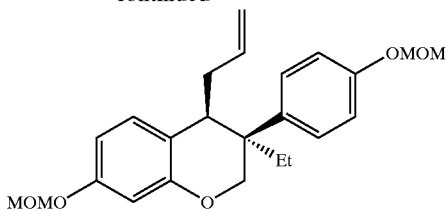

A 40% solution of diethyl azodicarboxylate in toluene (21.9 ml) was added dropwise to an ice-cold solution of (2RS,3RS)-2-ethyl-3-(2-hydroxy-4-methoxymethoxyphenyl)-2-(4-methoxymethoxy-phenyl)-5-hexenol (9.5 g) and triphenylphosphine (15.0 g) in dry 1,4-dioxane (150 ml) over 25 minutes under nitrogen atmosphere. The reaction mixture was stirred for 10 minutes on ice and for 30 minutes at room temperature. Under ice-cooling, water was added to the reaction mixture, which was then extracted twice with ethyl acetate. The combined organic layers were dried over magnesium sulfate and then concentrated to give a crude product, which was then purified by flash column chromatography (silica gel: Merck Kieselgel 60, eluent: hexane/ethyl acetate=50/1→20/1→10/1) to give (3RS,4RS)-3-ethyl-7-methoxymethoxy-3-(4-methoxymethoxyphenyl)-4-(2-propenyl)chroman (8.4 g, Yield 92.6%) as a white solid.

$^1$H-NMR (270 MHz, CDCl$_3$): d 7.08, 7.03 (each d, 4H, J=8.9 Hz, Ar—H), 6.94 (d, 1H, J=7.9 Hz, Ar—H), 6.5–6.6 (m, 2H, Ar—H), 5.5–5.7 (m, 1H, vinyl-H), 5.19, 5.14 (each s, 4H, OCH$_2$OMe), 4.85 (d, 1H, J=10.2 Hz, vinyl-H), 4.69 (dd, 1H, J=16.8, 1.7 Hz, vinyl-H), 4.49 (dd, 1H, J=10.6, 2.0 Hz, C2-H), 4.36 (d, 1H, J=10.6 Hz, C2-H), 3.51, 3.49 (each s, 6H, OCH$_3$), 2.7–2.9 (m, 1H, C4-H), 2.0–2.1 (m, 1H, allylic-H), 1.7–1.9 (m, 2H, allylic-H and C$\underline{H}_2$Me), 1.4–1.6 (m, 1H, C$\underline{H}_2$Me), 0.60 (t, 3H, J=7.3 Hz, CH$_2$C$\underline{H}_3$).

(3RS,4RS)-3-Ethyl-7-methoxymethoxy-3-(4-methoxymethoxyphenyl)-4-(2-propenyl)chroman (995 mg), the ethyl 2-(7,7,8,8,8-pentafluorooctyl)-9-decenoate prepared in Example 8 (2.0 g) and benzylidene bis (tricyclohexylphosphine)-dichlororuthenium (102 mg) were dissolved in dichloromethane (25 ml) and heated under reflux for 7 hours. The reaction mixture was concentrated and purified by flash column chromatography (silica gel: Merck Kieselgel 60, eluent:hexane/ethyl acetate=20/1→10/1) to give the desired olefin (1.05 g, Yield 55%) as a mixture of cis- and trans-forms. A solution of this mixture in ethyl acetate (50 ml) was stirred-with 10% Pd-C (210 mg) for 4 days under hydrogen atmosphere. The reaction mixture was filtered and evaporated under reduced pressure to remove the solvent, followed by purification via flash column chromatography (silica gel: Merck Kieselgel 60, eluent:hexane/ethyl acetate=10/1) to give ethyl 11-[(3RS,4RS)-3-ethyl-7-methoxymethoxy-3-(4-methoxymethoxyphenyl)chroman-4-yl]-2-(7,7,8,8,8-pentafluorooctyl)undecanoate (1.02 g).

$^1$H-NMR (270 MHz, CDCl$_3$): d 6.9–7.2 (m, 5H, Ar—H), 6.5–6.6 (m, 2H, Ar—H), 5.18 (s, 2H, OC$\underline{H}_2$OMe), 5.14 (s, 2H, OC$\underline{H}_2$OMe), 4.47 (dd, 1H, J=1.7, 11.0 Hz, C2-H), 4.35 (d, 1H, J=11.0 Hz, C2-H), 4.12 (q, 2H, J=7.2 Hz, OC$\underline{H}_2$CH$_3$) 3.50 (s, 3H, OMe), 3.49 (s, 3H, OMe), 2.6–2.7 (m, 1H, C4-H), 2.2–2.4 (m, 1H), 1.9–2.1 (m, 2H), 1.24 (t, 3H, J=7.1 Hz,OCH$_2$C$\underline{H}_3$) 0.9–1.8 (m, 30H), 0.58 (t, 3H, J=7.2 Hz, CH$_2$C$\underline{H}_3$).

(Step 7)

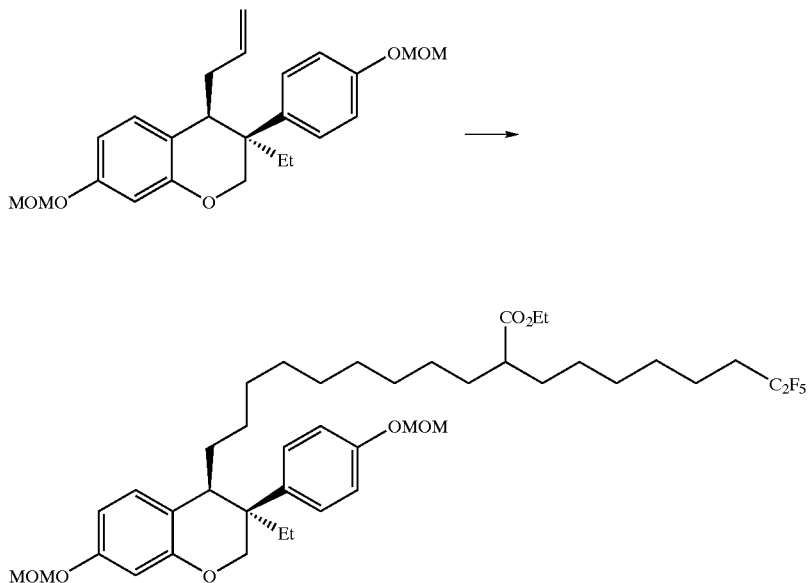

(Step 8)

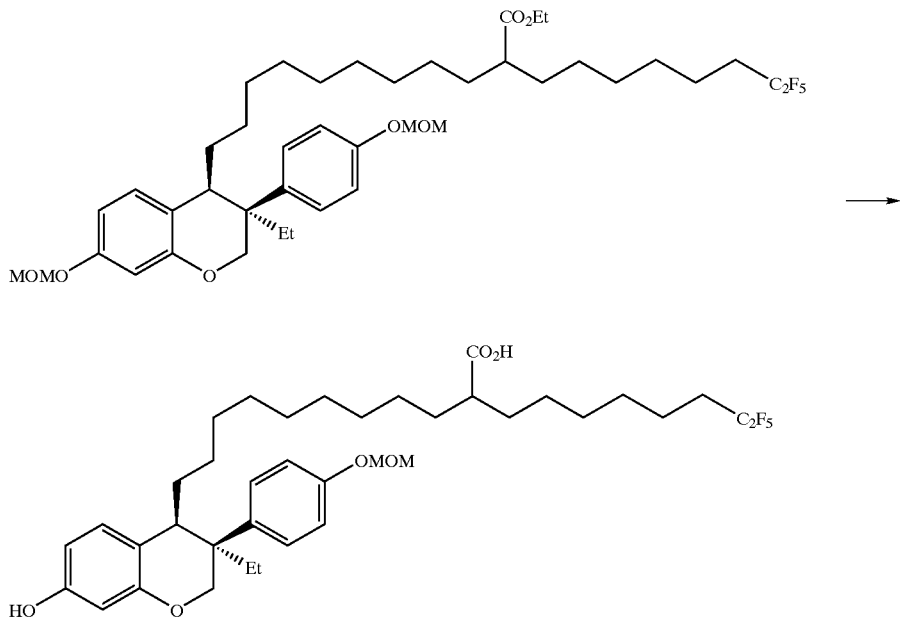

7N hydrochloric acid (12 ml) was added to a solution of ethyl 11-[(3RS,4RS)-3-ethyl-7-methoxymethoxy-3-(4-methoxymethoxyphenyl)chroman-4-yl]-2-(7,7,8,8,8-pentafluorooctyl)undecanoate (1.02 g) in ethanol (30 ml) followed by stirring for 1 day at room temperature and concentrated hydrochloric acid (1 ml) was further added to it followed by stirring for 1 hour at 25° C. The reaction mixture was neutralized by addition of saturated aqueous sodium bicarbonate, evaporated under reduced pressure to remove the solvent, and then extracted with ethyl acetate. The organic layer was dried over anhydrous sodium sulfate and evaporated under reduced pressure to remove the solvent, followed by purification via flash column chromatography (silica gel: Merck Kieselgel 60, eluent: hexane/ethyl acetate=10/1) to give a MOM-deprotected product (780 mg). The MOM-deprotected product thus prepared (780 mg) was dissolved in ethanol (25 ml). Aqueous sodium hydroxide (sodium hydroxide 364 mg/water 6.5 ml) was added to this solution followed by stirring for 3 hours at 80° C. The reaction mixture was cooled on ice, acidified by addition of concentrated hydrochloric acid, and then extracted with ethyl acetate. The organic layer was washed with water and saturated aqueous sodium chloride, dried over anhydrous sodium sulfate, and evaporated under reduced pressure to remove the solvent, followed by purification via flash column chromatography (silica gel: Wako C-200, eluent:hexane/ethyl acetate/dichloromethane=5/1/1→3/1/1) to give 11-[(3RS,4RS)-3-ethyl-7-hydroxy-3-(4-hydroxyphenyl)chroman-4-yl]-2-(7,7,8,8,8-pentafluorooctyl)-undecanoic acid (612 mg).

$^1$H-NMR (270 MHz, CD$_3$OD): d 7.02 (d, 2H, J=8.5 Hz, Ar—H), 6.84 (d, 1H, J=8.2 Hz, Ar—H), 6.79 (d, 2H, J=8.5 Hz, Ar—H), 6.30 (dd, 1H, J=2.5, 8.2 Hz, Ar—H), 6.24 (d, 1H, J=2.5 Hz, Ar—H), 4.44 (dd, 1H, J=1.6, 11.0 Hz, C2-H), 4.31 (d, 1H, J=11.0 Hz, C2-H), 2.5–2.7 (m, 1H, C4-H), 2.2–2.4 (m, 1H), 2.0–2.2 (m, 2H), 0.9–1.8 (m, 30H), 0.57 (t, 3H, J=7.4 Hz, CH$_2$CH$_3$).

Example 22

Synthesis of 11-[(3RS,4RS)-3-Ethyl-7-hydroxy-3-(4-hydroxyphenyl)chroman-4-yl]-2-(6,6,7,7,7-pentafluoroheptyl)-undecanoic Acid

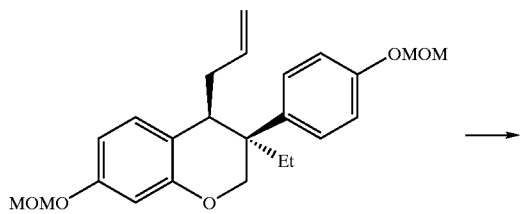

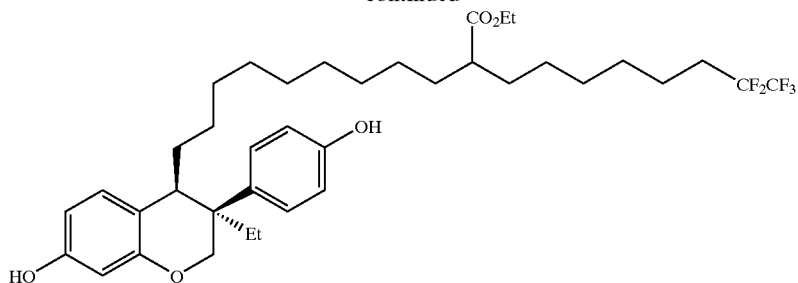

Starting with the allyl compound prepared in Example 21 and the ethyl 2-(6,6,7,7,7-pentafluoroheptyl)-9-decenoate prepared in Example 7, the same procedure as shown in Example 21 was repeated to give 11-[(3RS,4RS)-3-ethyl-7-hydroxy-3-(4-hydroxyphenyl)chroman-4-yl]-2-(6,6,7,7,7-pentafluoroheptyl)undecanoic acid.

$^1$H-NMR (300 MHz, CDCl$_3$): δ 6.98 (d, 2H, J=8.5 Hz), 6.88–6.80 (m, 3H), 6.36–6.34 (m, 2H), 4.37 (m, 2H), 2.60 (m, 1H), 2.40 (m, 1H), 2.10–1.85 (m, 2H), 1.80–0.90 (m, 28H), 0.56 (t, 3H, J=7.3 Hz).

Example 23

Synthesis of 11-[(3RS,4RS)-3-Ethyl-7-hydroxy-3-(4-hydroxyphenyl)chroman-4-yl]-2-(5,5,6,6,6-pentafluorohexyl)-undecanoic Acid

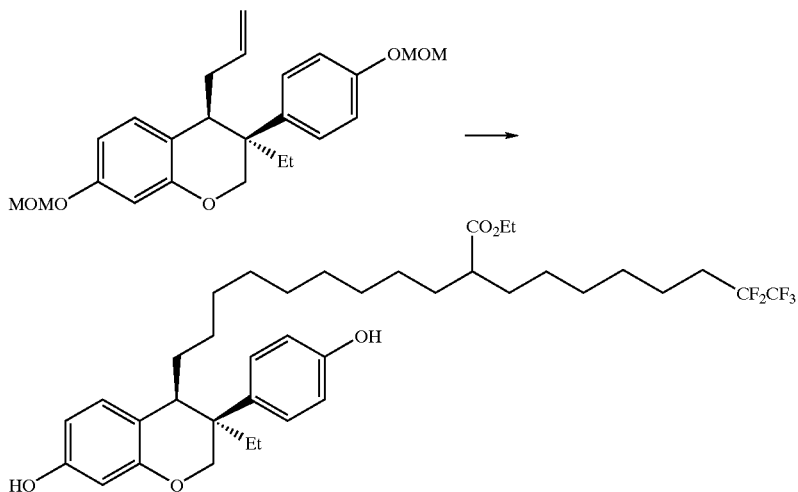

Starting with the allyl compound prepared in Example 21 and the ethyl 2-(5,5,6,6,6-pentafluorohexyl)-9-decenoate prepared in Example 5, the same procedure as shown in Example 21 was repeated to give 11-[(3RS,4RS)-3-ethyl-7-hydroxy-3-(4-hydroxyphenyl)chroman-4-yl]-2-(5,5,6,6,6-pentafluorohexyl)undecanoic acid.

$^1$H-NMR (270 MHz, CD$_3$OD): d 7.02 (d, J=9 Hz, 2H, Ar—H), 6.84 (d, J=8, 2 Hz, 1H, Ar—H), 6.78 (d, J=9 Hz, 2H, Ar—H), 6.29 (dd, J=8, 2 Hz, 1H, Ar—H), 6.22 (d, J=2 Hz, 1H, Ar—H), 4.43 (dd, J=11, 2 Hz, 1H, C2-H), 4.30 (d, J=11 Hz, 1H, C2-H), 2.55–2.65 (m, 1H, C4-H), 2.20–2.40 (m, 1H, C$\underline{H}$CO$_2$Et), 1.95–2.20 (m, 2H, C$\underline{H}_2$CF$_2$), 0.95–1.80 (m, 26H, C3-C$\underline{H}_2$CH$_3$ and alkyl-H), 0.56 (t, 3H, J=7 Hz, C3-CH$_2$C$\underline{H}_3$).

Example 24

Synthesis of 11-[(3RS,4RS)-3-Ethyl-7-hydroxy-3-(4-hydroxyphenyl)chroman-4-yl]-2-(4,4,5,5,5-pentafluoropentyl)-undecanoic Acid

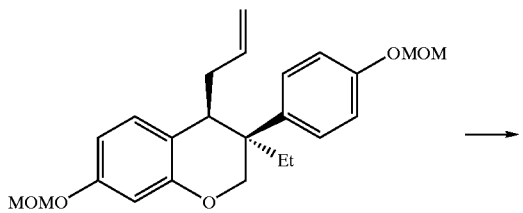

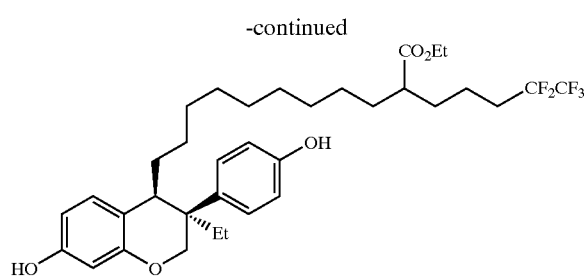

Starting with the allyl compound prepared in Example 21 and the ethyl 2-(4,4,5,5,5-pentafluoropentyl)-9-decenoate prepared in Example 6, the same procedure as shown in Example 21 was repeated to give 11-[(3RS,4RS)-3-ethyl-7-hydroxy-3-(4-hydroxyphenyl)chroman-4-yl]-2-(4,4,5,5,5-pentafluoropentyl)undecanoic acid.

$^1$H-NMR (300 MHz, CDCl$_3$): δ 7.00 (d, 2H, J=8.6 Hz), 6.88 (d, 1H, J=9.0 Hz), 6.85 (d, 2H, J=8.7 Hz), 6.37–6.32 (m, 2H), 4.45 (dd, 1H, J$_1$=10.7 Hz, J$_2$=1.5 Hz), 4.35 (d, 1H, J=10.7 Hz), 2.60 (m, 1H), 2.41 (m, 1H), 2.01–1.92 (m, 2H), 1.78–1.39 (m, 8H), 1.35–0.98 (m, 16H), 0.58 (t, 3H). Mass (ESI): 615 (M+1).

Example 25

Synthesis of 10-[(3RS,4RS)-3-Ethyl-7-hydroxy-3-(4-hydroxyphenyl)chroman-4-yl]-2-(7,7,8,8,8-pentafluorooctyl)decanoic Acid

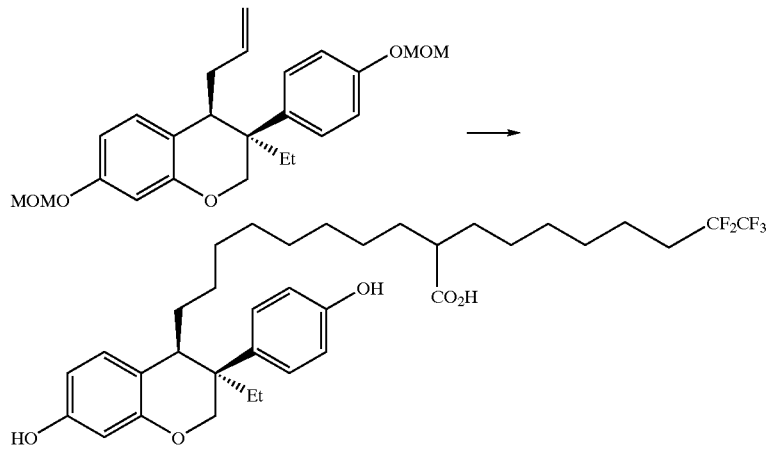

Starting with the allyl compound prepared in Example 21 and the ethyl 2-(7,7,8,8,8-pentafluorooctyl)-8-nonenoate prepared in Example 12, the same procedure as shown in Example 21 was repeated to give 10-[(3RS,4RS)-3-ethyl-7-hydroxy-3-(4-hydroxyphenyl)chroman-4-yl]-2-(7,7,8,8,8-pentafluorooctyl)decanoic acid.

$^1$H-NMR (300 MHz, CDCl$_3$): δ 7.02–6.96 (m, 2H), 6.88–6.80 (m, 3H), 6.38–6.34 (m, 2H), 4.46–4.32 (m, 2H), 2.60 (m, 1H), 2.37 (m, 1H), 2.10–1.90 (m, 2H), 1.76–1.68 (m, 2H), 1.55–1.00 (m, 26H), 0.55 (t, 3H, J=7.5 Hz). Mass (ESI): 643 (M+1).

Example 26

Synthesis of 10-[(3RS,4RS)-3-Ethyl-7-hydroxy-3-(4-hydroxyphenyl)chroman-4-yl]-2-(6,6,7,7,7-pentafluoroheptyl)-decanoic Acid

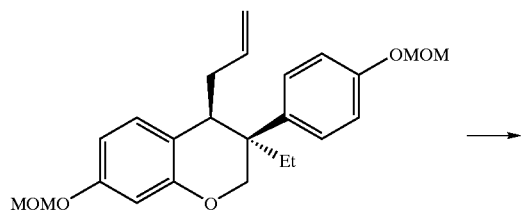

-continued

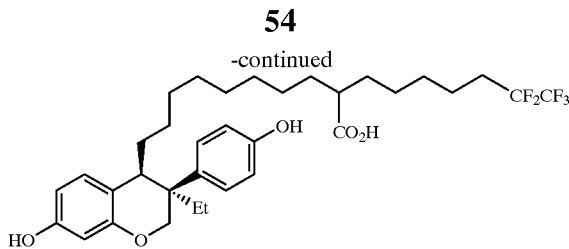

Starting with the allyl compound prepared in Example 21 and the ethyl 2-(6,6,7,7,7-pentafluoroheptyl)-8-nonenoate prepared in Example 11, the same procedure as shown in Example 21 was repeated to give 10-[(3RS,4RS)-3-ethyl-7-hydroxy-3-(4-hydroxyphenyl)chroman-4-yl]-2-(6,6,7,7,7-pentafluoroheptyl)decanoic acid.

$^1$H-NMR (300 MHz, CDCl$_3$): δ 6.98 (d, 2H), 6.92–6.78 (m, 3H), 6.39–6.29 (m, 2H), 4.45 (d, 1H), 4.35 (d, 1H), 2.61 (bs, 1H), 2.38 (m, 1H), 2.10–1.88 (m, 2H), 1.80–1.31 (m, 9H), 1.31–0.96 (m, 17H), 0.56 (t, 3H).

Example 27

Synthesis of 10-[(3RS,4RS)-3-Ethyl-7-hydroxy-3-(4-hydroxyphenyl)chroman-4-yl]-2-(5,5,6,6,6-pentafluorohexyl)decanoic Acid

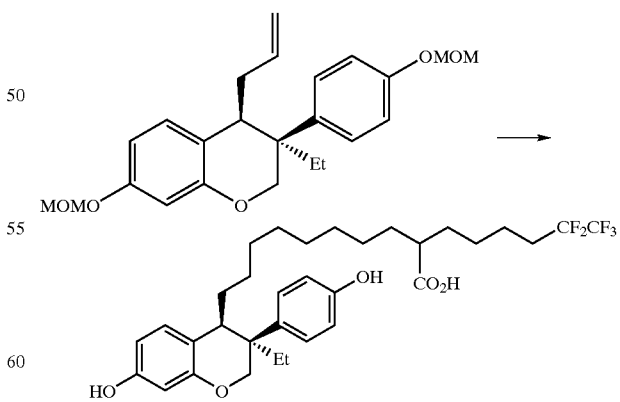

Starting with the allyl compound prepared in Example 21 and the ethyl 2-(5,5,6,6,6-pentafluorohexyl)-8-nonenoate prepared in Example 9, the same procedure as shown in Example 21 was repeated to give 10-[(3RS,4RS)-3-ethyl-7- hydroxy-3-(4-hydroxyphenyl)chroman-4-yl]-2-(5,5,6,6,6-pentafluorohexyl)decanoic acid.

¹H-NMR (300 MHz, CDCl₃): δ 6.98 (d, 2H), 6.90–6.77 (m, 3H), 6.39–6.29 (m, 2H), 4.47 (d, 1H), 4.36 (d, 1H), 2.59 (bs, 1H), 2.38 (m, 1H), 2.12–1.89 (m, 2H), 1.80–1.35 (m, 9H), 1.35–0.95 (m, 15H), 0.55 (t, 3H).

Example 28

Synthesis of 10-[(3RS,4RS)-3-Ethyl-7-hydroxy-3-(4-hydroxyphenyl)chroman-4-yl]-2-(4,4,5,5,5-pentafluoropentyl)-decanoic Acid

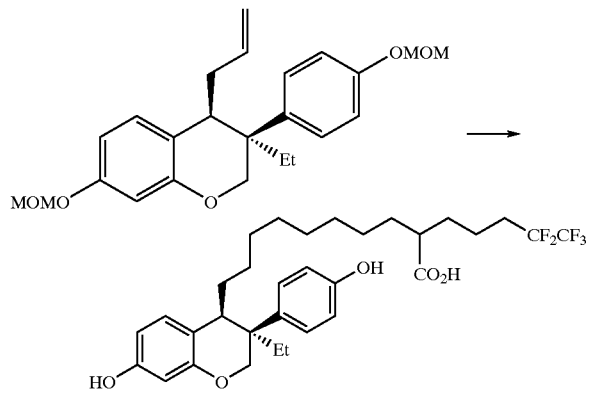

Starting with the allyl compound prepared in Example 21 and the ethyl 2-(4,4,5,5,5-pentafluoropentyl)-8-nonenoate prepared in Example 10, the same procedure as shown in Example 21 was repeated to give 10-[(3RS,4RS)-3-ethyl-7-hydroxy-3-(4-hydroxyphenyl)chroman-4-yl]-2-(4,4,5,5,5-pentafluoropentyl)decanoic acid.

¹H-NMR (300 MHz, CDCl₃): δ 7.00 (d, 2H), 6.89–6.84 (m, 3H), 6.37–6.34 (m, 2H), 4.45 (d, 1H), 4.35 (d, 1H), 2.61 (bs, 1H), 2.40 (m, 1H), 2.15–1.95 (m, 2H), 1.80–1.35 (m, 9H), 1.35–0.95 (m, 13H), 0.60 (t, 3H). Mass (ESI): 601 (M+1).

Example 29

Synthesis of 10-[(3RS,4RS)-7-Hydroxy-3-(4-hydroxyphenyl)-3-propylthiochroman-4-yl]-2-(4,4,5,5,5-pentafluoropentyl)-decanoic Acid

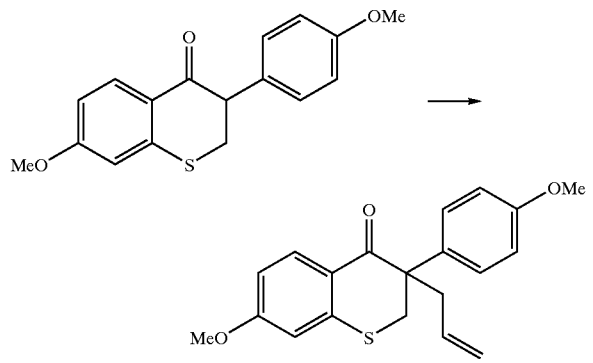

Allyl bromide (5.7 ml, 66.56 mmol) was added dropwise to a solution of 7-methoxy-3-(4-methoxyphenyl)thiochroman-4-one (2 g, 6.64 mmol) in dimethyl sulfoxide (34 ml). To this mixture, a solution of potassium tert-butoxide (5.22 g, 46.55 mmol) in dimethyl sulfoxide (70 ml) was slowly added dropwise at 10° C., followed by stirring for 2 hours at 10° C. and for 15 hours at room temperature. Water was added to the reaction mixture, which was then extracted three times with ethyl acetate. The combined organic layers were washed with water and saturated aqueous sodium chloride, and then dried over anhydrous magnesium sulfate. After distilling off the solvent, the residue was purified by silica gel column chromatography (eluent:ethyl acetate/hexane=1/9) to give 7-methoxy-3-(4-methoxyphenyl)-3-(2-propenyl)thiochroman-4-one (1.78 g, Yield 79%) as a colorless oil.

¹H-NMR (300 MHz, CDCl₃): δ 8.16 (d, 1H, J=8.9 Hz), 7.15 (d, 2H, J=8.9 Hz), 6.82 (d, 2H, J=8.9 Hz), 6.67 (dd, 1H), 6.53 (d, 1H), 5.62 (m, 1H), 5.06 (d, 2H, J=12.5 Hz), 3.82 (s, 6H), 3.59 (d, 1H, J=14.2 Hz,), 3.36 (d, 1H, J=14.2 Hz), 2.80–2.70 (m, 2H).

(Step 2)

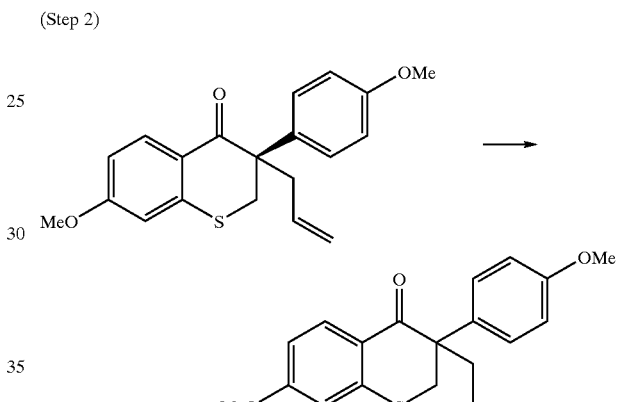

10% Pd/C (580 mg) was added to a solution of 7-methoxy-3-(4-methoxyphenyl)-3-(2-propenyl)thiochroman-4-one (1.75 g, 5.14 mmol) in ethyl acetate (20 ml) followed by stirring for 15 hours at room temperature under a hydrogen stream. Pd/C was removed by filtration through cellite and the resulting filtrate was concentrated under reduced pressure to give 7-methoxy-3-(4-methoxyphenyl)-3-propylthiochroman-4-one (1.7 g, Yield 96%).

¹H-NMR (270 MHz, CDCl₃): δ 8.17 (d, 1H, J=8.9 Hz), 7.17 (d, 2H, J=8.6 Hz), 6.84 (d, 2H, J=8.9 Hz), 6.69 (dd, 1H), 6.56 (d, 1H, J=2.6 Hz), 3.8 (s, 6H), 3.62 (d, 1H, J=14.0 Hz), 3.45 (d, 1H, J=14.0 Hz), 1.97 (t, 2H), 1.30–1.21 (m, 2H), 0.89 (t, 3H).

(Step 3)

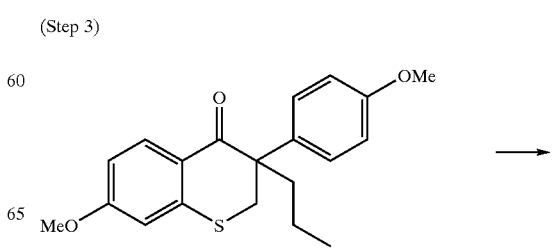

-continued

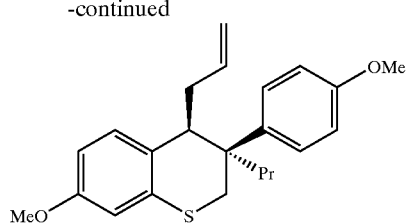

A solution of 7-methoxy-3-(4-methoxyphenyl)-3-propylthiochroman-4-one (1.7 g, 4.96 mmol) in anhydrous tetrahydrofuran (30 ml) was cooled to −78° C. Lithium aluminum hydride (94.2 mg, 2.48 mmol) was added to this solution, followed by stirring for 12 hours at room temperature. Saturated aqueous ammonium chloride (100 ml) was added to the reaction mixture, which was then extracted twice with ethyl acetate (100 ml). The combined organic layers were washed with water and saturated aqueous sodium chloride, and then dried over anhydrous magnesium sulfate. After distilling off the solvent, zinc iodide (1.9 g, 5.95 mmol) and allyltrimethylsilane (1.57 ml, 5.95 mmol) were added dropwise to a solution of the residue in 1,2-dichloroethane (50 ml) at 0° C., followed by stirring for 12 hours at room temperature. Water was added to the reaction mixture, which was then extracted twice with dichloromethane. The combined organic layers were washed with water and saturated aqueous sodium chloride, and then dried over anhydrous magnesium sulfate. After distilling off the solvent, the residue was purified by silica gel column chromatography (eluent:ethyl acetate/hexane=1/90) to give (3RS,4RS)-7-methoxy-3-(4-methoxyphenyl)-4-(2-propenyl)-3-propylthiochroman (1.32 g, Yield 72%).

$^1$H-NMR (300 MHz, CDCl$_3$): δ 7.25 (d, 2H, J=6.9 Hz), 7.05–6.86 (m, 3H), 6.71 (d, 1H, J=2.3 Hz), 6.56 (dd, 1H), 5.54 (m, 1H), 4.84 (d, 1H), 4.65 (d, 1H), 3.78 (s, 3H), 3.80 (s, 3H), 3.49 (d, 1H), 3.12 (d, 1H), 2.88 (m, 1H), 1.88 (m, 2H), 1.68 (m, 1H), 1.36 (m, 1H), 1.09 (m, 1H), 0.95–0.57 (m, 4H).

(Step 4)

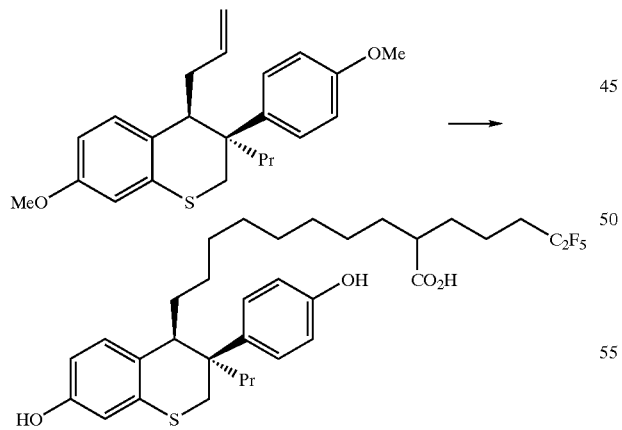

Starting with the allyl compound prepared in Step 3 and the ethyl 2-(4,4,5,5,5-pentafluoropentyl)-8-nonenoate prepared in Example 10, the same procedure as shown in Example 13 was repeated to give 10-[(3RS,4RS)-7-hydroxy-3-(4-hydroxyphenyl)-3-propylthiochroman-4-yl]-2-(4,4,5,5,5-pentafluoropentyl)decanoic acid.

$^1$H-NMR (300 MHz, CDCl$_3$): δ 7.18 (d, 2H, J=8.7 Hz), 6.90–6.75 (m, 3H), 6.66 (d, 1H, J=2.8 Hz), 6.49 (dd, 1H, J$_1$=8.2 Hz J$_2$=2.6 Hz), 3.48 (d, 1H, J=12.01 Hz), 3.08 (d, 1H, J=12.0 Hz), 2.70 (m, 1H), 2.40 (m, 1H), 2.10–1.90 (m, 2H), 1.80–1.40 (m, 6H), 1.40–0.90 (m, 17H), 0.80–0.55 (m, 4H). Mass (ESI): 631 (M+1).

Example 30

Synthesis of 11-[(3RS,4RS)-3-Ethyl-7-hydroxy-3-(4-hydroxyphenyl)thiochroman-4-yl]-2-(3,3,4,4,5,5,6,6,6-nonafluorohexyl)undecanoic Acid

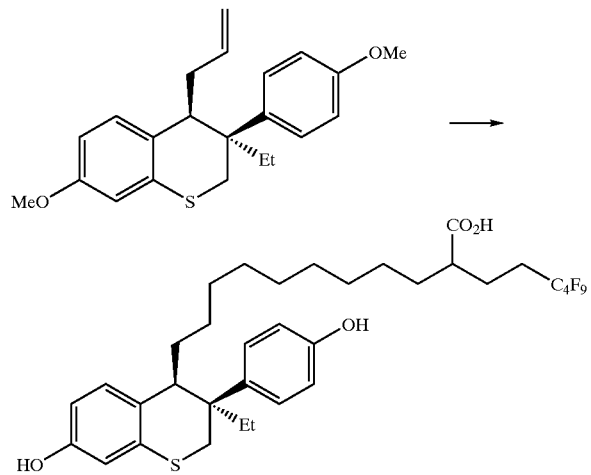

Starting with the ethyl 2-(3,3,4,4,5,5,6,6,6-nonafluorohexyl)-9-decenoate prepared from diethyl malonate, 8-bromo-1-octene and 1-iodo-3,3,4,4,5,5,6,6,6-nonafluorohexane as in Example 5 and the allyl compound prepared in Example 13, the same procedure as shown in Example 13 was repeated to give 11-[(3RS,4RS)-3-ethyl-7-hydroxy-3-(4-hydroxyphenyl)thiochroman-4-yl]-2-(3,3,4,4,5,5,6,6,6-nonafluorohexyl)undecanoic acid.

$^1$H-NMR (270 MHz, CDCl$_3$): d 7.16 (d, J=8.6 Hz, 2H), 6.83 (t, J=9.6 Hz, 3H), 6.64 (d, J=2.3 Hz, 1H), 6.46 (dd, J=2.3, 8.0 Hz, 1H), 3.43 (d, J=11.9 Hz, 1H), 3.07 (d, J=11.9 Hz, 1H), 2.72 (s, 1H), 2.52–2.35 (m, 1H), 2.10–0.90 (m, 24H), 0.47 (t, J=7.6 Hz, 3H).

Example 31

Synthesis of 10-[(3RS,4RS)-3-Ethyl-7-hydroxy-3-(4-hydroxyphenyl)thiochroman-4-yl]-2-(3,3,4,4,5,5,6,6,6-nonafluorohexyl)decanoic Acid

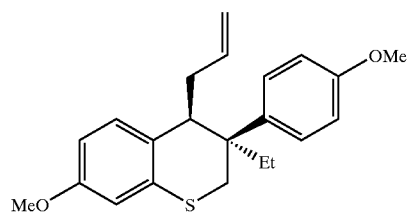

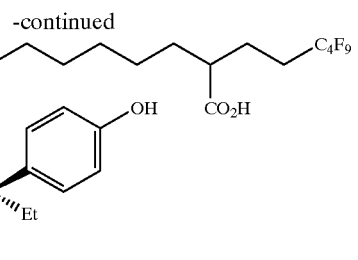

Starting with the ethyl 2-(3,3,4,4,5,5,6,6,6-nonafluorohexyl)-8-nonenoate prepared from diethyl malonate, 7-iodo-1-heptene and 1-iodo-3,3,4,4,5,5,6,6,6-nonafluorohexane as in Example 9 and the allyl compound prepared in Example 13, the same procedure as shown in Example 13 was repeated to give 10-[(3RS,4RS)-3-ethyl-7-hydroxy-3-(4-hydroxyphenyl)thiochroman-4-yl]-2-(3,3,4,4,5,5,6,6,6-nonafluorohexyl)decanoic acid.

$^1$H-NMR (300 MHz, CDCl$_3$): d 7.17 (d, J=9 Hz, 2H, Ar—H), 6.86 (d, J=8 Hz, 1H, Ar—H), 6.83 (d, J=9 Hz, 2H, Ar—H), 6.66 (d, J=2 Hz, 1H, Ar—H), 6.48 (dd, J=8 Hz, 2 Hz, 1H, Ar—H), 3.46 (d, J=12 Hz, 1H, C2-H), 3.08 (d, J=12 Hz, 1H, C2-H), 2.72 (br s, 1H, C4-H), 2.45 (m, 1H, C$\underline{H}$CO$_2$H), 2.2–2.0 (m, 2H, C$\underline{H}_2$CF$_2$), 2.0–0.9 (m, 20H, C3-C$\underline{H}_2$CH$_3$ and alkyl-H), 0.49 (t, 3H, J=7 Hz, 2H, C3-CH$_2$C$\underline{H}_3$).

Example 32

Synthesis of 11-[(3RS,4RS)-3-Ethyl-7-hydroxy-3-(4-hydroxyphenyl)chroman-4-yl]-2-(3,3,4,4,5,5,6,6,6-nonafluorohexyl)-undecanoic Acid

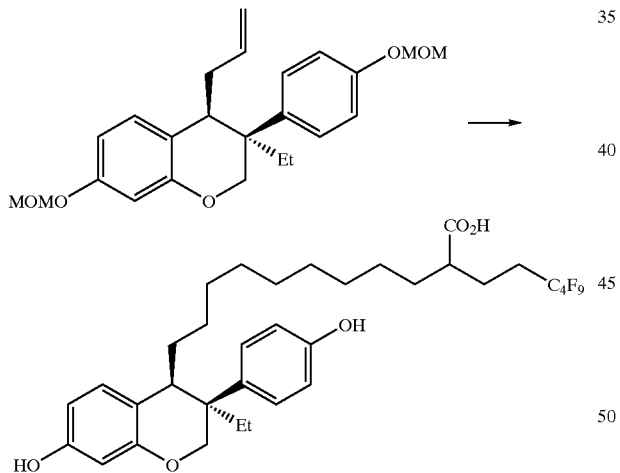

Starting with the ethyl 2-(3,3,4,4,5,5,6,6,6-nonafluorohexyl)-9-decenoate prepared from diethyl malonate, 8-bromo-1-octene and 1-iodo-3,3,4,4,5,5,6,6,6-nonafluorohexane as in Example 5 and the allyl compound prepared in Example 21, the same procedure as shown in Example 21 was repeated to give 11-[(3RS,4RS)-3-ethyl-7-hydroxy-3-(4-hydroxyphenyl)chroman-4-yl]-2-(3,3,4,4,5,5,6,6,6-nonafluorohexyl)undecanoic acid.

$^1$H-NMR (300 MHz, CDCl$_3$): δ 7.00 (d, 2H, J=9.6 Hz), 6.8 (d, 1H), 6.70 (d, 1H, J=8.6 Hz), 6.38–6.34 (m, 2H), 4.45 (d, 1H, J=10.7 Hz), 4.30 (d, 1H, J=10.7 Hz), 2.62 (m, 1H), 2.45 (m, 1H), 2.20–0.95 (m, 24H), 0.54 (t, 3H). Mass (ESI): 700 (M+1).

Example 33

Synthesis of 10-[(3RS,4RS)-3-Ethyl-7-hydroxy-3-(4-hydroxyphenyl)chroman-4-yl]-2-(3,3,4,4,5,5,6,6,6-nonafluorohexyl)-decanoic Acid

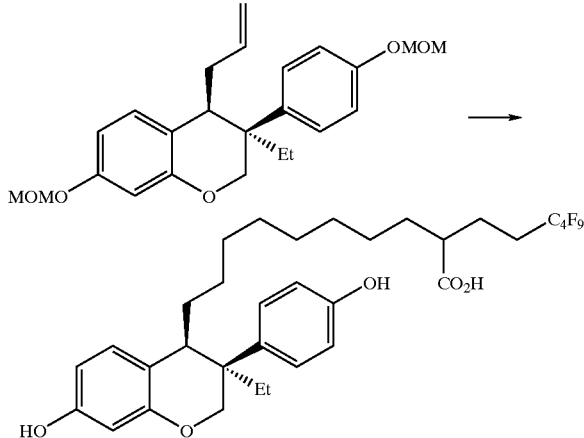

Starting with the ethyl 2-(3,3,4,4,5,5,6,6,6-nonafluorohexyl)-8-nonenoate prepared from diethyl malonate, 7-iodo-1-heptene and 1-iodo-3,3,4,4,5,5,6,6,6-nonafluorohexane as in Example 9 and the allyl compound prepared in Example 21, the same procedure as shown in Example 21 was repeated to give 10-[(3RS,4RS)-3-ethyl-7-hydroxy-3-(4-hydroxyphenyl)chroman-4-yl]-2-(3,3,4,4,5,5,6,6,6-nonafluorohexyl)decanoic acid.

$^1$H-NMR (300 MHz, CDCl$_3$): δ 7.02 (d, 2H, J=8.7 Hz), 6.87 (d, 1H, J=7.5 Hz), 6.84 (d, 2H, J=8.7 Hz), 6.40–6.30 (m, 2H), 4.45 (d, 1H, J=10.6 Hz), 4.35 (d, 1H, J=10.6 Hz), 2.61 (bs, 1H), 2.36 (m, 1H), 2.19–0.97 (m, 22H), 0.59 (t, 3H). Mass (ESI): 687 (M+1).

Example 34

Synthesis of 10-[(3RS,4RS)-3-Ethyl-7-hydroxy-3-(4-hydroxyphenyl)chroman-4-yl]-2-(4,4,5,5,6,6,7,7,7-nonafluoroheptyl)decanoic Acid

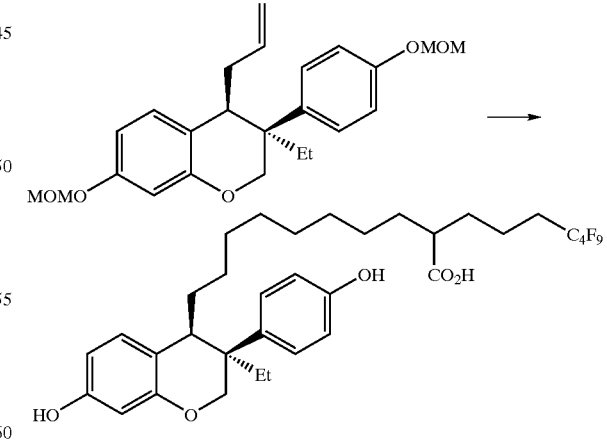

Starting with the allyl compound prepared in Example 21 and ethyl 2-(4,4,5,5,6,6,7,7,7-nonafluoroheptyl)-8-nonenoate prepared separately, the same procedure as shown in Example 21 was repeated to give 10-[(3RS,4RS)-3-ethyl-7-hydroxy-3-(4-hydroxyphenyl)chroman-4-yl]-2-(4,4,5,5,6,6,7,7,7-nonafluoroheptyl)decanoic acid.

¹H-NMR (270 MHz, CDCl₃): δ 7.01 (d, J=9 Hz, 2H, Ar—H), 6.90–6.82 (m, 3H, Ar—H), 6.38–6.35 (m, 2H, Ar—H), 4.45 (d, J=11 Hz, 1H), 4.34 (d, J=11 Hz, 1H), 2.60 (m, 1H), 2.41–2.36 (m, 1H), 2.10–1.05 (m, 24H), 0.58 (t, J=7 Hz, 3H).

Example 35

Synthesis of 11-[(3RS,4RS)-3-Ethyl-7-hydroxy-3-(4-hydroxyphenyl)chroman-4-yl]-2-(4,4,5,5,6,6,7,7,7-nonafluoroheptyl)undecanoic Acid

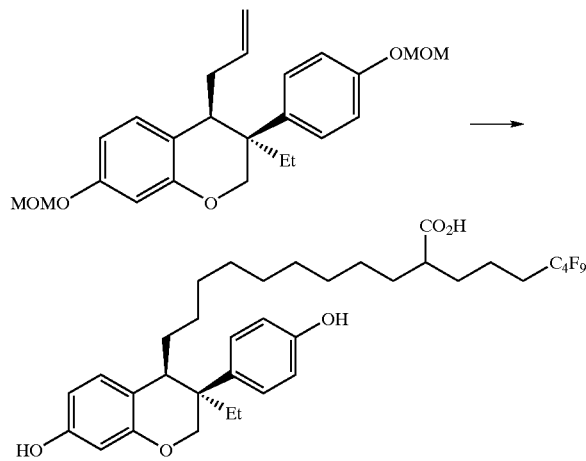

Starting with the allyl compound prepared in Example 21 and ethyl 2-(4,4,5,5,6,6,7,7,7-nonafluoroheptyl)-9-decenoate prepared separately, the same procedure as shown in Example 21 was repeated to give 11-[(3RS,4RS)-3-ethyl-7-hydroxy-3-(4-hydroxyphenyl)chroman-4-yl]-2-(4,4,5,5,6,6,7,7,7-nonafluoroheptyl)undecanoic acid.

¹H-NMR (270 MHz, CDCl₃): δ 6.99 (d, J=9 Hz, 2H, Ar—H), 6.89–6.80 (m, 3H, Ar—H), 6.36–6.33 (m, 2H, Ar—H), 4.44 (d, J=11 Hz, 1H), 4.33 (d, J=11 Hz, 1H), 2.59 (m, 1H), 2.39–2.34 (m, 1H), 2.16–1.05 (m, 26H), 0.56 (t, J=7 Hz, 3H).

Example 36

Synthesis of 10-[(3RS,4RS)-7-Hydroxy-3-(4-hydroxyphenyl)-3-propylthiochroman-4-yl]-2-(5,5,6,6,6-pentafluorohexyl)-decanoic Acid

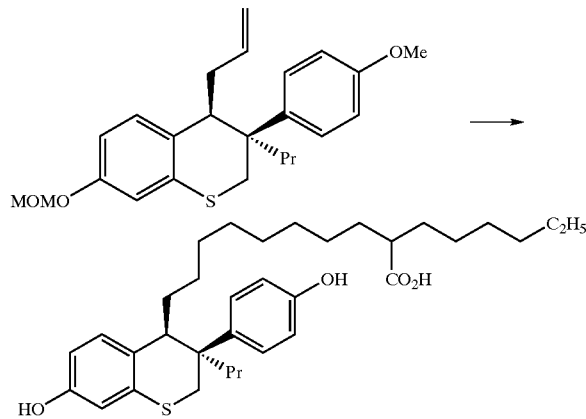

Starting with the allyl compound prepared in Example 29 and ethyl 2-(5,5,6,6,6-pentafluorohexyl)-8-nonenoate prepared separately, the same procedure as shown in Example 13 was repeated to give 10-[(3RS,4RS)-7-hydroxy-3-(4-hydroxyphenyl)-3-propylthiochroman-4-yl]-2-(5,5,6,6,6-pentafluorohexyl)decanoic acid.

¹H-NMR (300 MHz, CDCl₃): δ 7.18 (d, J=8.7 Hz, 2H, Ar—H), 6.80–6.87 (m, 3H, Ar—H), 6.66 (d, J=2.5 Hz, 1H, Ar—H), 6.49 (dd, J=8.2, 2.5 Hz, 1H, Ar—H), 3.46 (d, J=12.0 Hz, 1H, SCH₂), 3.08 (d, J=12.0 Hz, 1H, SCH₂), 2.70–2.72 (m, 1H, Ar—CH), 2.37–2.39 (m, 1H, CHCO₂H), 1.96–2.13 (m, 2H, CH₂CF₂), 0.62–1.64 (m, 29H, alkyl-H) Mass (ESI): 645 (M+1).

Example 37

Synthesis of 10-[(3RS,4RS)-7-Hydroxy-3-(4-hydroxyphenyl)-3-propylthiochroman-4-yl]-2-(3,3,4,4,5,5,6,6,6-nonafluorohexyl)decanoic Acid

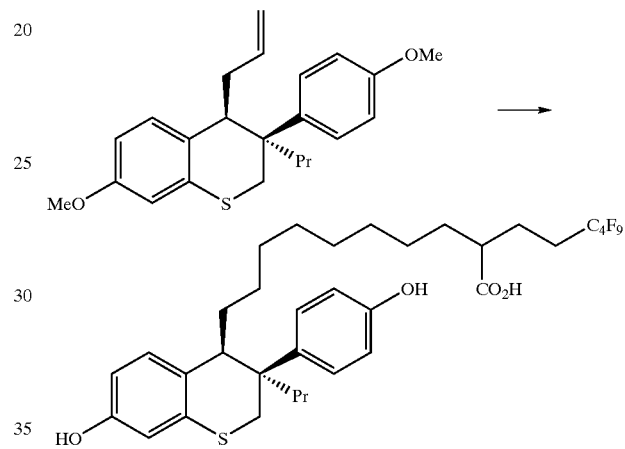

Starting with the allyl compound prepared in Example 29 and ethyl 2-(3,3,4,4,5,5,6,6,6-nonafluorohexyl)-8-nonenoate prepared separately, the same procedure as shown in Example 13 was repeated to give 10-[(3RS,4RS)-7-hydroxy-3-(4-hydroxyphenyl)-3-propylthiochroman-4-yl]-2-(3,3,4,4,5,5,6,6,6-nonafluorohexyl)decanoic acid.

¹H-NMR (300 MHz, CDCl₃): δ 7.18 (d, J=8.7 Hz, 2H, Ar—H), 6.87 (d, J=8.1 Hz, 1H, Ar—H), 6.83 (d, J=8.7 Hz, 2H, Ar—H), 6.67 (d, J=2.5 Hz, 1H, Ar—H), 6.49 (dd, J=8.1, 2.5 Hz, 1H, Ar—H), 3.46 (d, J=11.8 Hz, 1H, SCH₂), 3.09 (d, J=11.8 Hz, 1H, SCH₂), 2.66–2.75 (m, 1H, Ar—CH), 2.33–2.47 (m, 1H, CHCO₂H), 1.96–2.21 (m, 2H, CH₂CF₂), 0.59–1.93 (m, 25H, alkyl-H) Mass (ESI): 717 (M+1).

Example 38

Synthesis of 11-[(3RS,4RS)-7-Hydroxy-3-(4-hydroxyphenyl)-3-propylthiochroman-4-yl]-2-(4,4,5,5,5,-pentafluoropentyl)-undecanoic Acid

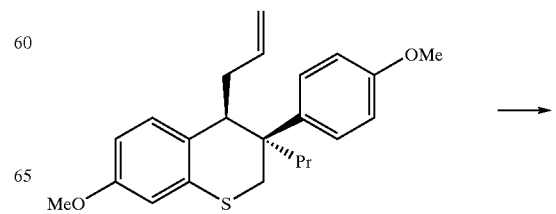

-continued

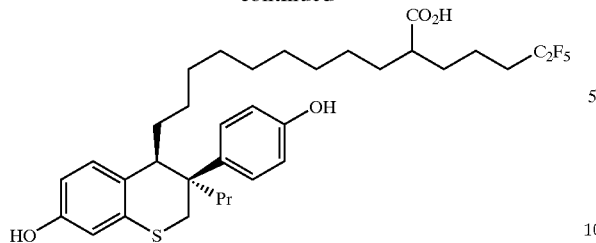

Starting with the allyl compound prepared in Example 29 and ethyl 2-(4,4,5,5,5,-pentafluoropentyl)-9-decenoate prepared separately, the same procedure as shown in Example 13 was repeated to give 11-[(3RS,4RS)-7-hydroxy-3-(4-hydroxyphenyl)-3-propylthiochroman-4-yl]-2-(4,4,5,5,5,-pentafluoropentyl)undecanoic acid.

$^1$H-NMR (300 MHz, CDCl$_3$): δ 7.18 (d, J=8.7 Hz, 2H, Ar—H), 6.87 (d, J=8.1 Hz, 1H, Ar—H), 6.83 (d, J=8.7 Hz, 2H, Ar—H), 6.67 (d, J=2.5 Hz, 1H, Ar—H), 6.49 (dd, J=8.1, 2.5 Hz, 1H, Ar—H), 3.47 (d, J=11.8 Hz, 1H, SCH$_2$), 3.09 (d, J=11.8 Hz, 1H, SCH$_2$), 2.68–2.76 (m, 1H, Ar—CH), 2.34–2.47 (m, 1H, CHCO$_2$H), 1.93–2.16 (m, 2H, CH$_2$CF$_2$), 0.59–1.85 (m, 29H, alkyl-H) Mass (ESI): 645 (M+1).

Example 39

Synthesis of 11-[(3RS,4RS)-7-Hydroxy-3-(4-hydroxyphenyl)-3-propylthiochroman-4-yl]-2-(3,3,4,4,5,5,6,6,6-nonafluorohexyl)undecanoic Acid

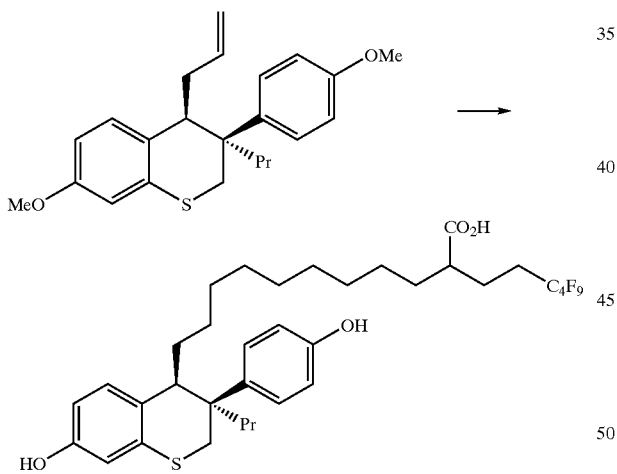

Starting with the allyl compound prepared in Example 29 and ethyl 2-(3,3,4,4,5,5,6,6,6-nonafluorohexyl)-9-decenoate prepared separately, the same procedure as shown in Example 13 was repeated to give 11-[(3RS,4RS)-7-hydroxy-3-(4-hydroxyphenyl)-3-propylthiochroman-4-yl]-2-(3,3,4,4,5,5,6,6,6-nonafluorohexyl)undecanoic acid.

$^1$H-NMR (300 MHz, CDCl$_3$): δ 7.18 (d, J=8.7 Hz, 2H, Ar—H), 6.87 (d, J=8.3 Hz, 1H, Ar—H), 6.83 (d, J=8.7 Hz, 2H, Ar—H), 6.67 (d, J=2.3 Hz, 1H, Ar—H), 6.49 (dd, J=8.3, 2.2 Hz, 1H, Ar—H), 3.46 (d, J=12.1 Hz, 1H, SCH$_2$), 3.09 (d, J=11.8 Hz, 1H, SCH$_2$), 2.68–2.75 (m, 1H, Ar—CH), 2.40–2.50 (m, 1H, CHCO$_2$H), 2.00–2.20 (m, 2H, CH$_2$CF$_2$), 0.60–1.95 (m, 27H, alkyl-H). Mass (ESI): 731 (M+1).

Example 40

Synthesis of 10-[(3RS,4RS)-7-Hydroxy-3-(4-hydroxyphenyl)-3-propylchroman-4-yl]-2-(5,5,6,6,6-pentafluorohexyl)decanoic Acid

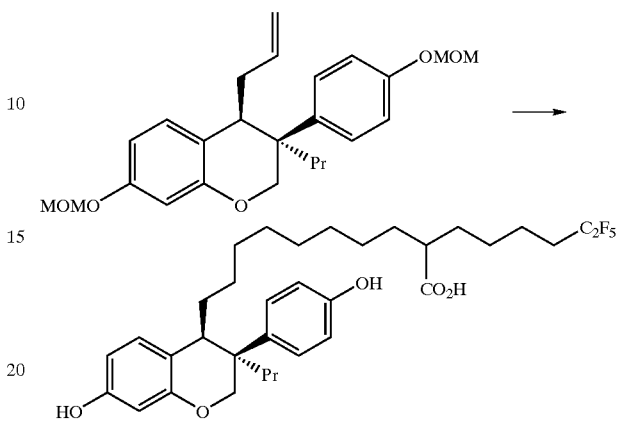

Starting with (3RS,4RS)-7-methoxymethoxy-3-(4-methoxymethoxyphenyl)-4-(2-propenyl)-3-propylchroman prepared as in Example 21 and ethyl 2-(5,5,6,6,6-pentafluorohexyl)-8-nonenoate prepared separately, the same procedure as shown in Example 21 was repeated to give 10-[(3RS,4RS)-7-hydroxy-3-(4-hydroxyphenyl)-3-propylchroman-4-yl]-2-(5,5,6,6,6-pentafluorohexyl)decanoic acid.

$^1$H-NMR (300 MHz, CDCl$_3$): δ 7.01 (d, J=8.7 Hz, 2H, Ar—H), 6.81–6.90 (m, 3H, Ar—H), 6.36–6.38 (m, 2H, Ar—H), 4.45 (d, J=10.5 Hz, 1H, OCH$_2$), 4.34 (d, J=10.7 Hz, 1H, OCH$_2$), 2.58–2.60 (m, 1H, Ar—CH), 2.37–2.39 (m, 1H, CHCO$_2$H), 1.87–2.11 (m, 2H, CH$_2$CF$_2$), 0.66–1.69 (m, 29H, alkyl-H) Mass (ESI): 629 (M+1).

Example 41

Synthesis of 10-[(3RS,4RS)-7-Hydroxy-3-(4-hydroxyphenyl)-3-propylchroman-4-yl]-2-(3,3,4,4,5,5,6,6,6-nonafluorohexyl)-decanoic Acid

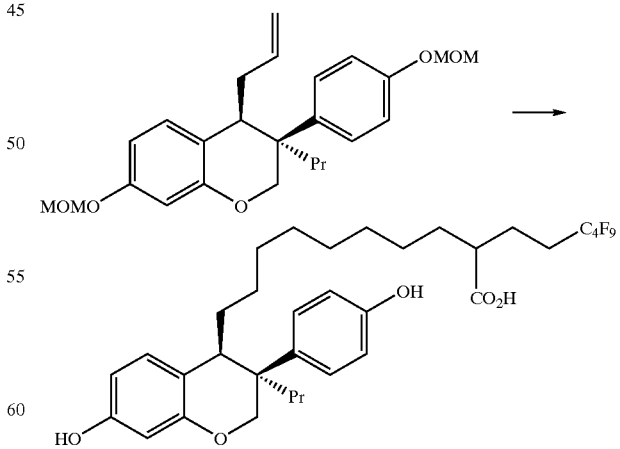

Starting with (3RS,4RS)-7-methoxymethoxy-3-(4-methoxymethoxyphenyl)-4-(2-propenyl)-3-propylchroman prepared as in Example 21 and ethyl 2-(3,3,4,4,5,5,6,6,6-nonafluorohexyl)-8-nonenoate prepared separately, the same procedure as shown in Example 21 was repeated to give 10-[(3RS,4RS)-7-hydroxy-3-(4-hydroxyphenyl)-3-propylchroman-4-yl]-2-(3,3,4,4,5,5,6,6,6-nonafluorohexyl) decanoic acid.

$^1$H-NMR (300 MHz, CDCl$_3$): δ 7.01 (d, J=8.6 Hz, 2H, Ar—H), 6.89 (d, J=8.1 Hz, 1H, Ar—H), 6.83 (d, J=8.5 Hz, 2H, Ar—H), 6.36–6.38 (m, 2H, Ar—H), 4.45 (d, J=10.6 Hz, 1H, OCH$_2$), 4.34 (d, J=10.8 Hz, 1H, OCH$_2$), 2.56–2.58 (m, 1H, Ar—CH), 2.46–2.48 (m, 1H, CHCO$_2$H), 2.08–2.23 (m, 2H, CH$_2$CF$_2$), 0.62–2.03 (m, 25H, alkyl-H). Mass (ESI): 701 (M+1).

Example 42

Synthesis of 10-[(3RS,4RS)-7-Hydroxy-3-(4-hydroxyphenyl)-3-propylchroman-4-yl]-2-(4,4,5,5,6,6,7,7,7-nonafluoroheptyl)-decanoic Acid

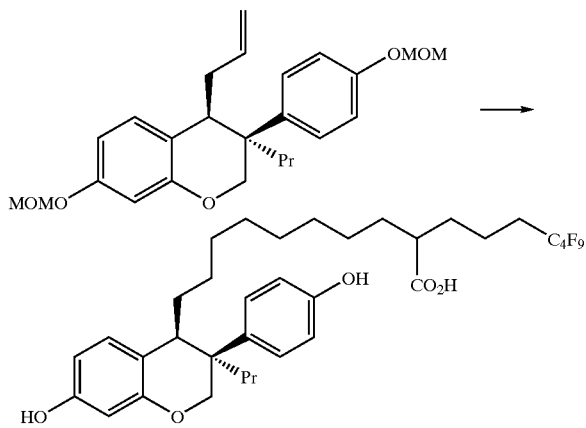

Starting with (3RS,4RS)-7-methoxymethoxy-3-(4-methoxymethoxyphenyl)-4-(2-propenyl)-3-propylchroman prepared as in Example 21 and ethyl 2-(4,4,5,5,6,6,7,7,7-nonafluoroheptyl)-8-nonenoate prepared separately, the same procedure as shown in Example 21 was repeated to give 10-[(3RS,4RS)-7-hydroxy-3-(4-hydroxyphenyl)-3-propylchroman-4-yl]-2-(4,4,5,5,6,6,7,7,7-nonafluoroheptyl) decanoic acid.

$^1$H-NMR (270 MHz, CD$_3$OD): δ 7.02 (d, J=8.6 Hz, 2H), 6.84 (d, J=8.3 Hz, 1H, C5-CH), 6.77 (d, J=8.6 Hz, 2H), 6.30 (dd, J=8.3, 2.3 Hz, 1H, C6-CH), 6.23 (d, J=2.3 Hz, 1H, C8-CH), 4.42 (d, J=11.0 Hz, 1H, C2-CH$_2$), 4.31 (d, J=11.0 Hz, 1H, C2-CH$_2$), 2.65–2.58 (m, 1H, C4-CH), 2.4–2.0 (m, 3H), 1.7–0.9 (m, 22H), 0.9–0.7 (m, 2H), 0.68 (t, J=7.0 Hz, 3H).

Example 43

Synthesis of 11-[(3RS,4RS)-7-Hydroxy-3-(4-hydroxyphenyl)-3-propylchroman-4-yl]-2-(4,4,5,5,5-pentafluoropentyl)-undecanoic Acid

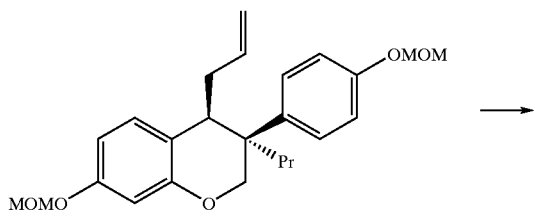

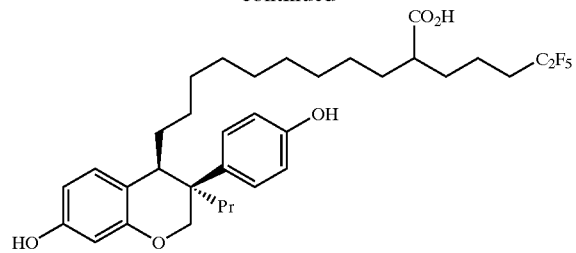

Starting with (3RS,4RS)-7-methoxymethoxy-3-(4-methoxymethoxyphenyl)-4-(2-propenyl)-3-propylchroman prepared as in Example 21 and ethyl 2-(4,4,5,5,5-pentafluoropentyl)-9-decenoate prepared separately, the same procedure as shown in Example 21 was repeated to give 11-[(3RS,4RS)-7-hydroxy-3-(4-hydroxyphenyl)-3-propylchroman-4-yl]-2-(4,4,5,5,5-pentafluoropentyl) undecanoic acid.

$^1$H-NMR (300 MHz, CDCl$_3$): δ 7.01 (d, J=8.3 Hz, 2H, Ar—H), 6.89 (d, J=8.2 Hz, 1H, Ar—H), 6.82 (d, J=8.3 Hz, 2H, Ar—H), 6.36–6.38 (m, 2H, Ar—H), 4.45 (d, J=10.6 Hz, 1H, OCH$_2$), 4.35 (d, J=10.6 Hz, 1H, OCH$_2$), 2.60–2.62 (m, 1H, Ar—CH), 2.40–2.42 (m, 1H, CHCO$_2$H), 1.95–2.20 (m, 2H, CH$_2$CF$_2$), 0.67–1.80 (m, 29H, alkyl-H). Mass (ESI): 629 (M+1).

Example 44

Synthesis of 11-[(3RS,4RS)-7-Hydroxy-3-(4-hydroxyphenyl)-3-propylchroman-4-yl]-2-(5,5,6,6,6-pentafluorohexyl)-undecanoic Acid

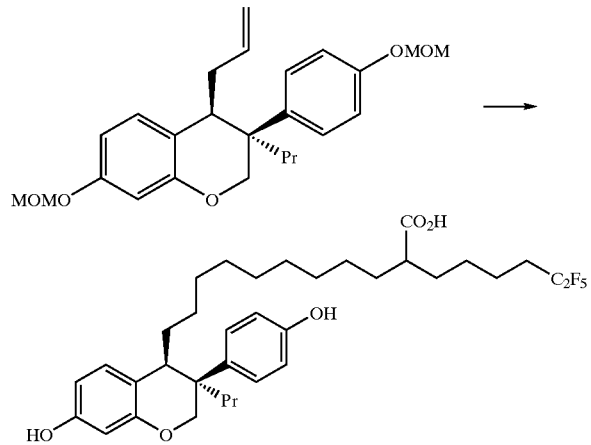

Starting with (3RS,4RS)-7-methoxymethoxy-3-(4-methoxymethoxyphenyl)-4-(2-propenyl)-3-propylchroman prepared as in Example 21 and ethyl 2-(5,5,6,6,6-pentafluorohexyl)-9-decenoate prepared separately, the same procedure as shown in Example 21 was repeated to give 11-[(3RS,4RS)-7-hydroxy-3-(4-hydroxyphenyl)-3-propylchroman-4-yl]-2-(5,5,6,6,6-pentafluorohexyl) undecanoic acid.

$^1$H-NMR (300 MHz, CDCl$_3$): δ 7.04 (d, J=8.5 Hz, 2H, Ar—H), 6.92 (d, J=8.7 Hz, 1H, Ar—H), 6.86 (d, J=8.7 Hz, 2H, Ar—H), 6.39–6.42 (m, 2H, Ar—H), 4.48 (d, J=10.7 Hz, 1H, OCH$_2$), 4.37 (d, J=10.7 Hz, 1H, OCH$_2$), 2.62–2.64 (m, 1H, Ar—CH), 2.35–2.45 (m, 1H, CHCO$_2$H), 1.92–2.11 (m, 2H, CH$_2$CF$_2$), 0.69–1.69 (m, 31H, alkyl-H). Mass (ESI): 643 (M+1).

Example 45

Synthesis of 11-[(3RS,4RS)-7-Hydroxy-3-(4-hydroxyphenyl)-3-propylchroman-4-yl]-2-(3,3,4,4,5,5,6,6,6-nonafluorohexyl)-undecanoic Acid

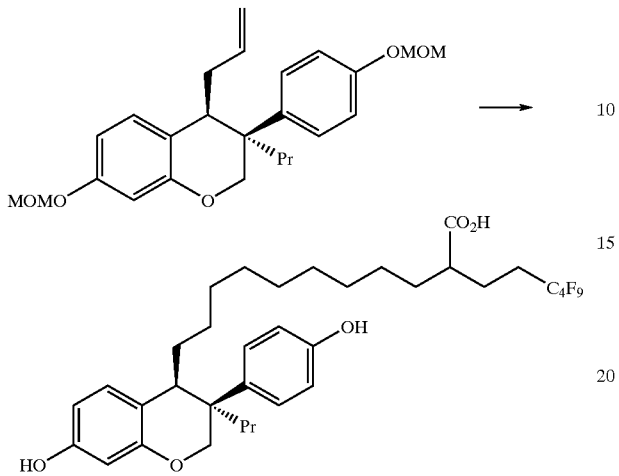

Starting with (3RS,4RS)-7-methoxymethoxy-3-(4-methoxymethoxyphenyl)-4-(2-propenyl)-3-propylchroman prepared as in Example 21 and ethyl 2-(3,3,4,4,5,5,6,6,6-nonafluorohexyl)-9-decenoate prepared separately, the same procedure as shown in Example 21 was repeated to give 11-[(3RS,4RS)-7-hydroxy-3-(4-hydroxyphenyl)-3-propylchroman-4-yl]-2-(3,3,4,4,5,5,6,6,6-nonafluorohexyl) undecanoic acid.

$^{1}$H-NMR (300 MHz, CDCl$_3$): δ 7.03 (d, J=8.7 Hz, 2H, Ar—H), 6.90 (d, J=8.2 Hz, 1H, Ar—H), 6.85 (d, J=8.6 Hz, 2H, Ar—H), 6.37–6.41 (m, 2H, Ar—H), 4.47 (d, J=10.5 Hz, 1H, OCH$_2$), 4.36 (d, J=10.9 Hz, 1H, OCH$_2$), 2.60–2.63 (m, 1H, Ar—CH), 2.43–2.50 (m, 1H, CHCO$_2$H), 2.14–2.25 (m, 2H, CH$_2$CF$_2$), 0.65–2.02 (m, 27H, alkyl-H). Mass (ESI): 715 (M+1).

Example 46

Synthesis of 11-[(3RS,4RS)-7-Hydroxy-3-(4-hydroxyphenyl)-3-propylchroman-4-yl]-2-(4,4,5,5,6,6,7,7,7-nonafluoroheptyl)-undecanoic Acid

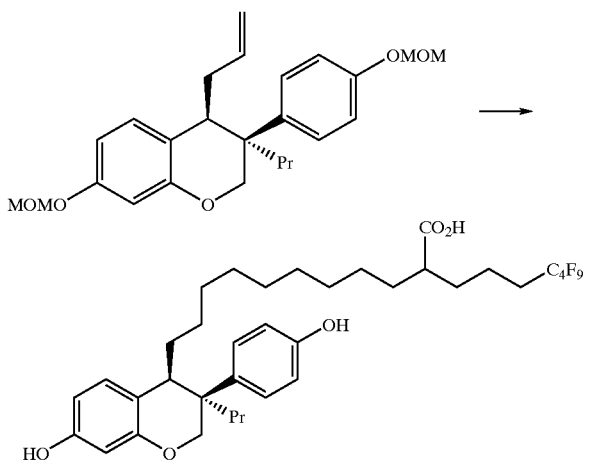

Starting with (3RS,4RS)-7-methoxymethoxy-3-(4-methoxymethoxyphenyl)-4-(2-propenyl)-3-propylchroman prepared as in Example 21 and ethyl 2-(4,4,5,5,6,6,7,7,7-nonafluoroheptyl)-9-decenoate prepared separately, the same procedure as shown in Example 21 was repeated to give 11-[(3RS,4RS)-7-hydroxy-3-(4-hydroxyphenyl)-3-propylchroman-4-yl]-2-(4,4,5,5,6,6,7,7,7-nonafluoroheptyl) undecanoic acid.

$^{1}$H-NMR (300 MHz, CDCl$_3$): δ 7.00 (d, J=8.7 Hz, 2H, Ar—H), 6.90 (d, J=9.0 Hz, 1H, Ar—H), 6.83 (d, J=8.6 Hz, 2H, Ar—H), 6.36–6.39 (m, 2H, Ar—H), 4.45 (d, J=10.4 Hz, 1H, OCH$_2$), 4.35 (d, J=10.4 Hz, 1H, OCH$_2$), 2.59–2.62 (m, 1H, Ar—CH), 2.40–2.43 (m, 1H, CHCO$_2$H), 2.02–2.14 (m, 2H, CH$_2$CF$_2$), 0.65–1.75 (m, 29H, alkyl-H). Mass (ESI): 729 (M+1).

Example 47

Synthesis of 10-[(3RS,4RS)-3-Butyl-7-hydroxy-3-(4-hydroxyphenyl)chroman-4-yl]-2-(4,4,5,5,6,6,7,7,7-nonafluoroheptyl)decanoic Acid

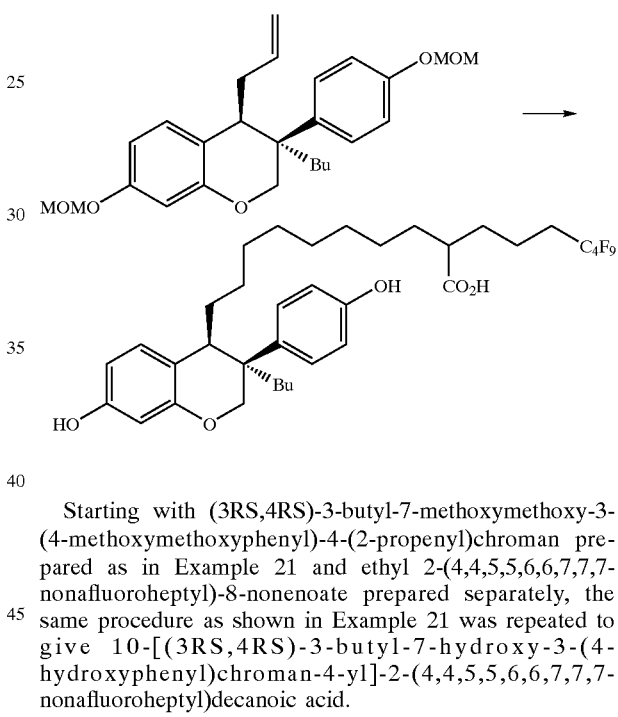

Starting with (3RS,4RS)-3-butyl-7-methoxymethoxy-3-(4-methoxymethoxyphenyl)-4-(2-propenyl)chroman prepared as in Example 21 and ethyl 2-(4,4,5,5,6,6,7,7,7-nonafluoroheptyl)-8-nonenoate prepared separately, the same procedure as shown in Example 21 was repeated to give 10-[(3RS,4RS)-3-butyl-7-hydroxy-3-(4-hydroxyphenyl)chroman-4-yl]-2-(4,4,5,5,6,6,7,7,7-nonafluoroheptyl)decanoic acid.

$^{1}$H-NMR (300 MHz, CDCl$_3$): δ 7.01 (d, J=8.7 Hz, 2H, Ar—H), 6.81–6.90 (m, 3H, Ar—H), 6.35–6.37 (m, 2H, Ar—H), 4.45 (d, J=11.8 Hz, 1H, OCH$_2$), 4.34 (d, J=10.7 Hz, 1H, OCH$_2$), 2.56–2.58 (m, 1H, Ar—CH), 2.41 (m, 1H, CHCO$_2$H), 1.95–2.17 (m, 2H, CH$_2$CF$_2$), 0.68–1.76 (m, 29H, alkyl-H) Mass (ESI): 729 (M+1).

Example 48

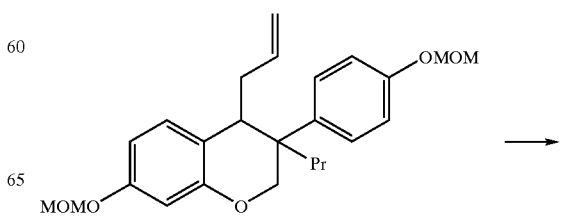

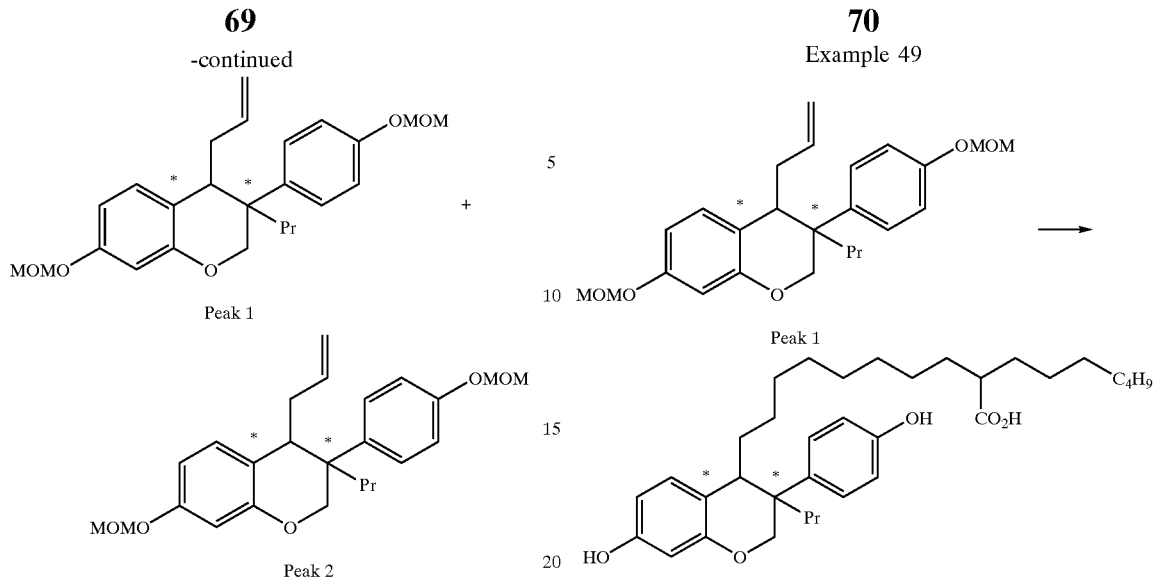

Peak 1

Peak 2

Optical resolution of (3RS,4RS)-7-methoxymethoxy-3-(4-methoxymethoxyphenyl)-4-(2-propenyl)-3-propylchroman prepared as in Example 21 was carried out using a chiral column (CHIRALPAK AD) to give optically active isomers.

Peaks 1 and 2 were detected at retention times of 7.3 and 8.0 minutes, respectively, under the following conditions:

Column used: CHIRALPAK AD (0.46 cm ID×25 cm L)
Mobile phase:hexane/isopropanol=100/1 (v/v)
Flow rate: 1.0 ml/min
Column temperature: 40° C.
Detection wavelength: 254 nm Example 49

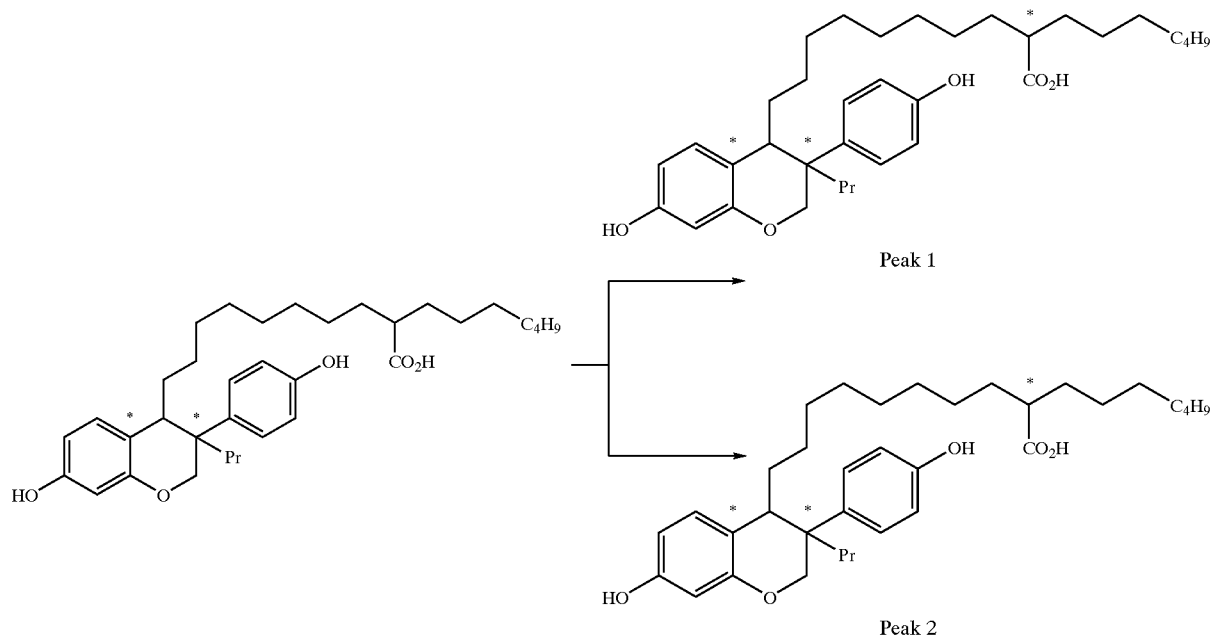

Peak 1

Starting with the optically active isomer prepared in Example 48 (Peak 1) and ethyl 2-(4,4,5,5,6,6,7,7,7-nonafluoroheptyl)-8-nonenoate prepared separately, the same procedure as shown in Example 21 was repeated to give 10-[7-hydroxy-3-(4-hydroxyphenyl)-3-propylchroman-4-yl]-2-(4,4,5,5,6,6,7,7,7-nonafluoroheptyl) decanoic acid having chiral carbons at positions 3 and 4.

This compound provided the same NMR data as shown in Example 42.

Example 50

Peak 1

Peak 2

Optical resolution of the 10-[7-hydroxy-3-(4-hydroxyphenyl)-3-propylchroman-4-yl]-2-(4,4,5,5,6,6,7,7,7-nonafluoroheptyl)decanoic acid having chiral carbons at positions 3 and 4 which was prepared in Example 49 was carried out using a chiral column (CHIRALPAK AD) to give optically active isomers, each having chiral carbons at positions 3 and 4 and at α-position to the carboxyl group.

Each isomer provided the same NMR data as shown in Example 42.

Peaks 1 and 2 were detected at retention times of 6.9 and 8.3 minutes, respectively, under the following conditions:

Column used: CHIRALPAK AD (0.46 cm ID×25 cm L)

Mobile phase:hexane/isopropanol/acetic acid=80/20/0.1 (v/v/v)

Flow rate: 1.0 ml/min

Column temperature: 40° C.

Detection wavelength: 280 nm

Starting with the optically active isomer prepared in Example 48 (Peak 2) and ethyl 2-(4,4,5,5,6,6,7,7,7-nonafluoroheptyl)-8-nonenoate prepared separately, the same procedure as shown in Example 21 was repeated to give 10-[7-hydroxy-3-(4-hydroxyphenyl)-3-propylchroman-4-yl]-2-(4,4,5,5,6,6,7,7,7-nonafluoroheptyl) decanoic acid having chiral carbons at positions 3 and 4.

This compound provided the same NMR data as shown in Example 42.

Example 52

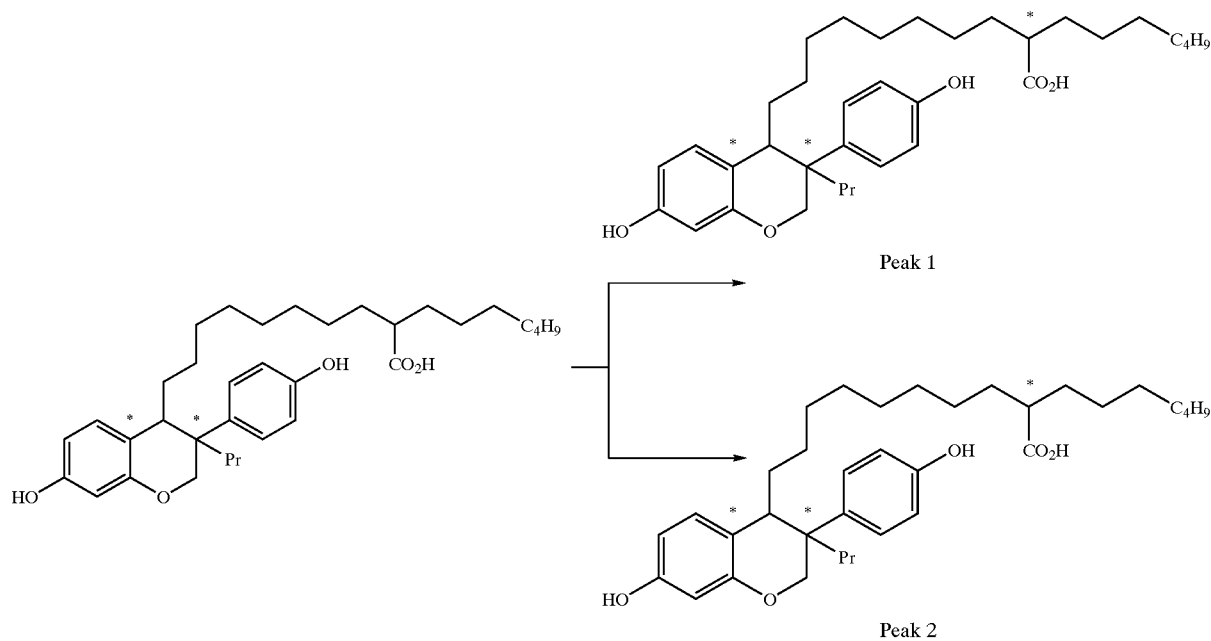

Example 51

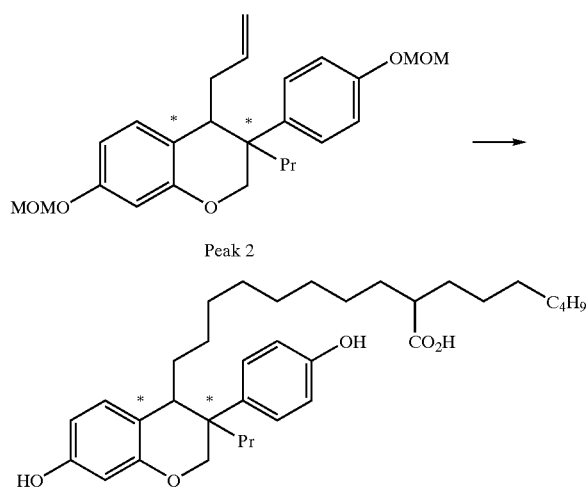

Optical resolution of the 10-[7-hydroxy-3-(4-hydroxyphenyl)-3-propylchroman-4-yl]-2-(4,4,5,5,6,6,7,7,7-nonafluoroheptyl)decanoic acid having chiral carbons at positions 3 and 4 which was prepared in Example 51 was carried out using a chiral column (CHIRALCEL OJ) to give optically active isomers, each having chiral carbons at positions 3 and 4 and at α-position to the carboxyl group.

Each isomer provided the same NMR data as shown in Example 42.

Peaks 1 and 2 were detected at retention times of 7.1 and 11.9 minutes, respectively, under the following conditions:

Column used: CHIRALCEL OJ (0.46 cm ID×25 cm L)

Mobile phase:hexane/ethanol/acetic acid=90/10/0.1 (v/v/v)

Flow rate: 1.0 ml/min

Column temperature: 40° C.

Detection wavelength: 280 nm

Test Example 1

Anti-estrogenic Activity (Oral Administration)

Test compounds were assayed for their oral anti-estrogenic activity in the following manner. In this experiment, the compounds prepared in Examples mentioned above were used as test compounds. As control compounds, the following two were used: a compound described in Example 7 of WO98/25916 and a compound corresponding to general formula (1) of the present invention, provided that $R_1$ was a methyl group, i.e., 10-[(3RS,4RS)-7-hydroxy-3-(4-hydroxyphenyl)-3-methylthiochroman-4-yl]-2-(4,4,5,5,5-pentafluoropentyl)decanoic acid, which had been synthesized according to Reaction Schemes 1 to 7 mentioned above.

To determine anti-estrogenic activity, mice (ICR, weight 30±2 g) which had been ovariectomized 2 weeks before were subcutaneously administered with 17β-estradiolbenzoate (Sigma) in an amount of 0.1 μg/mouse for 3 days and the degree by which the test compound inhibited the increase in uterine weight was measured. In this experiment, each of the test and control compounds was suspended in 5% arabic gum solution and orally administered for 3 days on a once-a-day basis. After 24 hours from the last administration, the test animals were sacrificed and the uteri were removed and weighed. The results obtained are shown in Table 3 below.

TABLE 2

Anti-estrogenic activity in ovariectomized mice administered with 17β-estradiol (oral administration, 3 days)

| Compound | Test compound/dose (p.o., 3 days) mg/kg | Inhibition (%) |
|---|---|---|
| Example 16 | 10 | 96 |
| Example 15 | 10 | 92 |
| Example 14 | 10 | 81 |
| Example 31 | 10 | 85 |
| Example 20 | 10 | 91 |
| Example 30 | 10 | 89 |
| Example 29 | 10 | 91 |
| Example 22 | 10 | 83 |
| Example 32 | 10 | 82 |
| Example 34 | 10 | 90 |
| Example 35 | 10 | 93 |
| Example 36 | 10 | 89 |
| Example 38 | 10 | 84 |
| Example 39 | 10 | 84 |
| Example 40 | 10 | 82 |
| Example 41 | 10 | 89 |
| Example 42 | 10 | 95 |
| Example 43 | 10 | 85 |
| Example 44 | 10 | 84 |
| Example 45 | 10 | 85 |
| Example 46 | 10 | 94 |
| Example 47 | 10 | 89 |
| Example 50, Peak 1 | 10 | 96 |
| Example 50, Peak 2 | 10 | 95 |
| Example 52, Peak 1 | 10 | 93 |
| Example 7 of WO98/25916 | 10 | 68.1 |
| 10-[(3Rs,4Rs)-7-hydroxy-3-(4-hydroxyphenyl)-3-methyl-thiochroman-4-yl]-2-(4,4,5,5,5-pentafluoropentyl)decanoic acid | 10 | 75 |

The results shown in Table 3 above indicate that the compounds of the present invention show a superior inhibitory activity against the estradiol-induced increase in uterine weight, as compared to the anti-estrogenic compounds: the compound described in Example 7 of WO98/25916 and 10-[(3RS,4RS)-7-hydroxy-3-(4-hydroxyphenyl)-3-methylthiochroman-4-yl]-2-(4,4,5,5,5-pentafluoropentyl)decanoic acid.

INDUSTRIAL APPLICABILITY

The compounds of the present invention are advantageous in pharmaceutical use because they have an excellent anti-estrogenic activity as well as providing a sufficiently high activity even when administered orally.

What is claimed is:

1. A compound having the following formula (1):

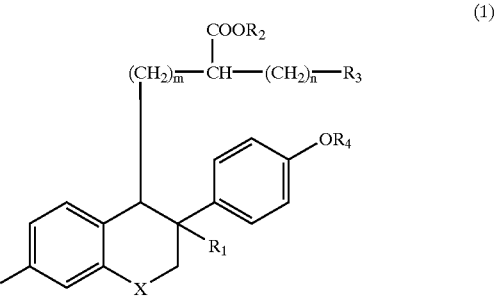

in which $R_1$ represents an ethyl group, a n-propyl group, an i-propyl group or a butyl group;

$R_2$ represents a hydrogen atom or a salt-forming metal;

$R_3$ represents a linear or branched $C_1$–$C_7$ halogenoalkyl group;

each of $R_4$ and $R_5$ independently represents a hydrogen atom, an optionally substituted linear or branched $C_1$–$C_3$ alkyl group, an acyl group or a salt-forming metal;

X represents an oxygen atom or a sulfur atom;

m represents an integer of 2 to 14; and n represents an integer of 2 to 7;

or an enantiomer of the compound, or a hydrate or a pharmaceutically acceptable salt of the compound or its enantiomer.

2. The compound according to claim 1, wherein each of $R_4$ and $R_5$ is independently a hydrogen atom or a salt-forming metal, or an enantiomer of the compound, or a hydrate or a pharmaceutically acceptable salt of the compound or its enantiomer.

3. The compound according to claim 1, wherein $R_3$ in formula (1) is a linear or branched $C_1$–$C_7$ fluoroalkyl group, or an enantiomer of the compound, or a hydrate or a pharmaceutically acceptable salt of the compound or its enantiomer.

4. The compound according to claim 1, wherein $R_3$ in formula (1) is a linear or branched $C_1$–$C_5$ perhalogenoalkyl group or a group of the following formula (2):

(2)

in which
each of $R_6$ and $R_7$ is a linear or branched $C_1$–$C_3$ perhalogenoalkyl group,
or an enantiomer of the compound, or a hydrate or a pharmaceutically acceptable salt of the compound or its enantiomer.

5. The compound according to claim 3, wherein $R_3$ in formula (1) is a linear or branched $C_1$–$C_5$ perfluoroalkyl group or a group of the following formula (2):

(2)

in which
each of $R_6$ and $R_7$ is a linear or branched $C_1$–$C_3$ perfluoroalkyl group,
or an enantiomer of the compound, or a hydrate or a pharmaceutically acceptable salt of the compound or its enantiomer.

6. The compound according to claim 1, wherein $R_3$ in formula (1) is a linear or branched $C_2$–$C_4$ perfluoroalkyl group, or an enantiomer of the compound, or a hydrate or a pharmaceutically acceptable salt of the compound or its enantiomer.

7. The compound according to claim 1, wherein m in formula (1) is an integer of 6 to 10, or an enantiomer of the compound, or a hydrate or a pharmaceutically acceptable salt of the compound or its enantiomer.

8. The compound according to claim 1, wherein m in formula (1) is an integer of 8 to 10, or an enantiomer of the compound, or a hydrate or a pharmaceutically acceptable salt of the compound or its enantiomer.

9. The compound according to claim 1, wherein n in formula (1) is an integer of 2 to 6, or an enantiomer of the compound, or a hydrate or a pharmaceutically acceptable salt of the compound or its enantiomer.

10. The compound according to claim 1, wherein $R_1$ in formula (1) is an ethyl group or an n-propyl group, or an enantiomer of the compound, or a hydrate or a pharmaceutically acceptable salt of the compound or its enantiomer.

11. The compound according to claim 1, wherein in formula (1), $R_1$ is an ethyl group, an n-propyl group or a n-butyl group; $R_2$ is a hydrogen atom, an alkali metal or an alkaline earth metal; $R_3$ is a perfluoroethyl group, a perfluoro-n-propyl group, a perfluoro-n-butyl group or a 1,1,1,3,3,3-hexafluoroisopropyl group; X is an oxygen atom or a sulfur atom; m is an integer of 8 or 9; and n is an integer of 2 to 6; or an enantiomer of the compound, or a hydrate or a pharmaceutically acceptable salt of the compound or its enantiomer.

12. The compound according to claim 1, wherein in formula (1):

a) $R_1$ is an ethyl group; $R_2$ is a hydrogen atom, $R_3$ is a perfluoroethyl group, X is a sulfur atom, m is 8, and n is 3;

b) $R_1$ is an ethyl group, $R_2$ is a hydrogen atom, $R_3$ is a perfluoroethyl group, X is a sulfur atom, m is 8, and n is 4;

c) $R_1$ is an ethyl group, $R_2$ is a hydrogen atom, $R_3$ is a perfluoroethyl group, X is a sulfur atom, m is 8, and n is 5;

d) $R_1$ is an ethyl group, $R_2$ is a hydrogen atom, $R_3$ is a perfluorobutyl group, X is a sulfur atom, m is 8, and n is 2;

e) $R_1$ is an ethyl group, $R_2$ is a hydrogen atom, $R_3$ is a perfluoroethyl group, X is a sulfur atom, m is 9, and n is 3;

f) $R_1$ is an ethyl group, $R_2$ is a hydrogen atom, $R_3$ is a perfluorobutyl group, X is a sulfur atom, m is 9, and n is 2;

g) $R_1$ is an n-propyl group, $R_2$ is a hydrogen atom, $R_3$ is a perfluoroethyl group, X is a sulfur atom, m is 8, and n is 3;

h) $R_1$ is an ethyl group, $R_2$ is a hydrogen atom, $R_3$ is a perfluoroethyl group, X is an oxygen atom, m is 9, and n is 5;

i) $R_1$ is an ethyl group, $R_2$ is a hydrogen atom, $R_3$ is a perfluorobutyl group, X is an oxygen atom, m is 9, and n is 2;

j) $R_1$ is an ethyl group, $R_2$ is a hydrogen atom, $R_3$ is a perfluorobutyl group, X is an oxygen atom, m is 8, and n is 3;

k) $R_1$ is an ethyl group, $R_2$ is a hydrogen atom, $R_3$ is a perfluorobutyl group, X is an oxygen atom, m is 9, and n is 3;

l) $R_1$ is an n-propyl group, $R_2$ is a hydrogen atom, $R_3$ is a perfluoroethyl group, X is a sulfur atom, m is 8, and n is 4;

m) $R_1$ is an n-propyl group, $R_2$ is a hydrogen atom, $R_3$ is a perfluorobutyl group, X is a sulfur atom, m is 8, and n is 2;

n) $R_1$ is an n-propyl group, $R_2$ is a hydrogen atom, $R_3$ is a perfluoroethyl group, X is a sulfur atom, m is 9, and n is 3;

o) $R_1$ is an n-propyl group, $R_2$ is a hydrogen atom, $R_3$ is a perfluorobutyl group, X is a sulfur atom, m is 9, and n is 2;

p) $R_1$ is an n-propyl group, $R_2$ is a hydrogen atom, $R_3$ is a perfluoroethyl group, X is an oxygen atom, m is 8, and n is 4;

q) $R_1$ is an n-propyl group, $R_2$ is a hydrogen atom, $R_3$ is a perfluorobutyl group, X is an oxygen atom, m is 8, and n is 2;

s) $R_1$ is an n-propyl group, $R_2$ is a hydrogen atom, $R_3$ is a perfluorobutyl group, X is an oxygen atom, m is 8, and n is 3;

t) $R_1$ is an n-propyl group, $R_2$ is a hydrogen atom, $R_3$ is a perfluoroethyl group, X is an oxygen atom, m is 9, and n is 3;

u) $R_1$ is an n-propyl group, $R_2$ is a hydrogen atom, $R_3$ is a perfluoroethyl group, X is an oxygen atom, m is 9, and n is 4;

v) $R_1$ is an n-propyl group, $R_2$ is a hydrogen atom, $R_3$ is a perfluorobutyl group, X is an oxygen atom, m is 9, and n is 2;

w) $R_1$ is an n-propyl group, $R_2$ is a hydrogen atom, $R_3$ is a perfluorobutyl group, X is an oxygen atom, m is 9, and n is 3;

x) $R_1$ is an n-butyl group, $R_2$ is a hydrogen atom, $R_3$ is a perfluorobutyl group, X is an oxygen atom, m is 8, and n is 3; or y) $R_1$ is an n-propyl group, $R_2$ is a hydrogen atom, $R_3$ is a perfluorobutyl group, X is an oxygen atom, m is 8, and n is 3;

or an enantiomer of the compound, or a hydrate or a pharmaceutically acceptable salt of the compound or its enantiomer.

13. The compound according to claim 1, wherein in formula (1), the configuration of 3- and 4-position carbons in the parent scaffold (chroman or thiochroman ring) is (3RS,4RS), (3R,4R) or (3S,4S), or an enantiomer of the compound, or a hydrate or a pharmaceutically acceptable salt of the compound or its enantiomer.

14. The compound according to claim 1, wherein in formula (1), the carbon to which a carboxylic acid or its metal salt is bonded has R- or S-configuration, wherein said carbon is the carbon on the side chain which is bonded to 4-position of the parent scaffold (chroman or thiochroman ring), or a mixture thereof, or an enantiomer of the compound, or a hydrate or a pharmaceutically acceptable salt of the compound or its enantiomer.

15. The compound according to claim 1, which is selected from the group consisting of:

10-[(3RS,4RS)-3-ethyl-7-hydroxy-3-(4-hydroxyphenyl)-thiochroman-4-yl]-2-(4,4,5,5,5-pentafluoropentyl)decanoic acid;

10-[(3RS,4RS)-3-ethyl-7-hydroxy-3-(4-hydroxyphenyl)-thiochroman-4-yl]-2-(5,5,6,6,6-pentafluorohexyl)decanoic acid;

10-[(3RS,4RS)-3-ethyl-7-hydroxy-3-(4-hydroxyphenyl)-thiochroman-4-yl]-2-(6,6,7,7,7-pentafluoroheptyl)decanoic acid;

10-[(3RS,4RS)-3-ethyl-7-hydroxy-3-(4-hydroxyphenyl)-thiochroman-4-yl]-2-(3,3,4,4,5,5,6,6,6-nonafluorohexyl)-decanoic acid;

11-[(3RS,4RS)-3-ethyl-7-hydroxy-3-(4-hydroxyphenyl)-thiochroman-4-yl]-2-(4,4,5,5,5-pentafluoropentyl)undecanoic acid;

11-[(3RS,4RS)-3-ethyl-7-hydroxy-3-(4-hydroxyphenyl)-thiochroman-4-yl]-2-(3,3,4,4,5,5,6,6,6-nonafluorohexyl)-undecanoic acid;

10-[(3RS,4RS)-7-hydroxy-3-(4-hydroxyphenyl)-3-propylthiochroman-4-yl]-2-(4,4,5,5,5-pentafluoropentyl)decanoic acid;

11-[(3RS,4RS)-3-ethyl-7-hydroxy-3-(4-hydroxyphenyl)-chroman-4-yl]-2-(6,6,7,7,7-pentafluoroheptyl)undecanoic acid;

11-[(3RS,4RS)-3-ethyl-7-hydroxy-3-(4-hydroxyphenyl)-chroman-4-yl]-2-(3,3,4,4,5,5,6,6,6-nonafluorohexyl)-undecanoic acid;

10-[(3RS,4RS)-3-ethyl-7-hydroxy-3-(4-hydroxyphenyl)-chroman-4-yl]-2-(4,4,5,5,6,6,7,7,7-nonafluoroheptyl)-decanoic acid;

11-[(3RS,4RS)-3-ethyl-7-hydroxy-3-(4-hydroxyphenyl)-chroman-4-yl]-2-(4,4,5,5,6,6,7,7,7-nonafluoroheptyl)-undecanoic acid;

10-[(3RS,4RS)-7-hydroxy-3-(4-hydroxyphenyl)-3-propylthiochroman-4-yl]-2-(5,5,6,6,6-pentafluorohexyl)decanoic acid;

10-[(3RS,4RS)-7-hydroxy-3-(4-hydroxyphenyl)-3-propylthiochroman-4-yl]-2-(3,3,4,4,5,5,6,6,6-nonafluorohexyl)-decanoic acid;

11-[(3RS,4RS)-7-hydroxy-3-(4-hydroxyphenyl)-3-propylthiochroman-4-yl]-2-(4,4,5,5,5,-pentafluoropentyl)-undecanoic acid;

11-[(3RS,4RS)-7-hydroxy-3-(4-hydroxyphenyl)-3-propylthiochroman-4-yl]-2-(3,3,4,4,5,5,6,6,6-nonafluorohexyl)-undecanoic acid;

10-[(3RS,4RS)-7-hydroxy-3-(4-hydroxyphenyl)-3-propylchroman-4-yl]-2-(5,5,6,6,6-pentafluorohexyl)decanoic acid;

10-[(3RS,4RS)-7-hydroxy-3-(4-hydroxyphenyl)-3-propylchroman-4-yl]-2-(3,3,4,4,5,5,6,6,6-nonafluorohexyl)decanoic acid;

10-[(3RS,4RS)-7-hydroxy-3-(4-hydroxyphenyl)-3-propylchroman-4-yl]-2-(4,4,5,5,6,6,7,7,7-nonafluoroheptyl)-decanoic acid;

11-[(3RS,4RS)-7-hydroxy-3-(4-hydroxyphenyl)-3-propylchroman-4-yl]-2-(4,4,5,5,5-pentafluoropentyl)undecanoic acid;

11-[(3RS,4RS)-7-hydroxy-3-(4-hydroxyphenyl)-3-propylchroman-4-yl]-2-(5,5,6,6,6-pentafluorohexyl)undecanoic acid;

11-[(3RS,4RS)-7-hydroxy-3-(4-hydroxyphenyl)-3-propylchroman-4-yl]-2-(3,3,4,4,5,5,6,6,6-nonafluorohexyl)-undecanoic acid;

11-[(3RS,4RS)-7-hydroxy-3-(4-hydroxyphenyl)-3-propylchroman-4-yl]-2-(4,4,5,5,6,6,7,7,7-nonafluoroheptyl)-undecanoic acid;

10-[(3RS,4RS)-3-butyl-7-hydroxy-3-(4-hydroxyphenyl)-chroman-4-yl]-2-(4,4,5,5,6,6,7,7,7-nonafluoroheptyl)-decanoic acid; and 10-[(3RS,4RS)-7-hydroxy-3-(4-hydroxyphenyl)-3-propylthiochroman-4-yl]-2-(4,4,5,5,6,6,7,7,7-nonafluoroheptyl)-decanoic acid;

or an enantiomer of the compound, or a hydrate or a pharmaceutically acceptable salt of the compound or its enantiomer.

16. A compound represented by Peak 1 or 2 shown in the following formula:

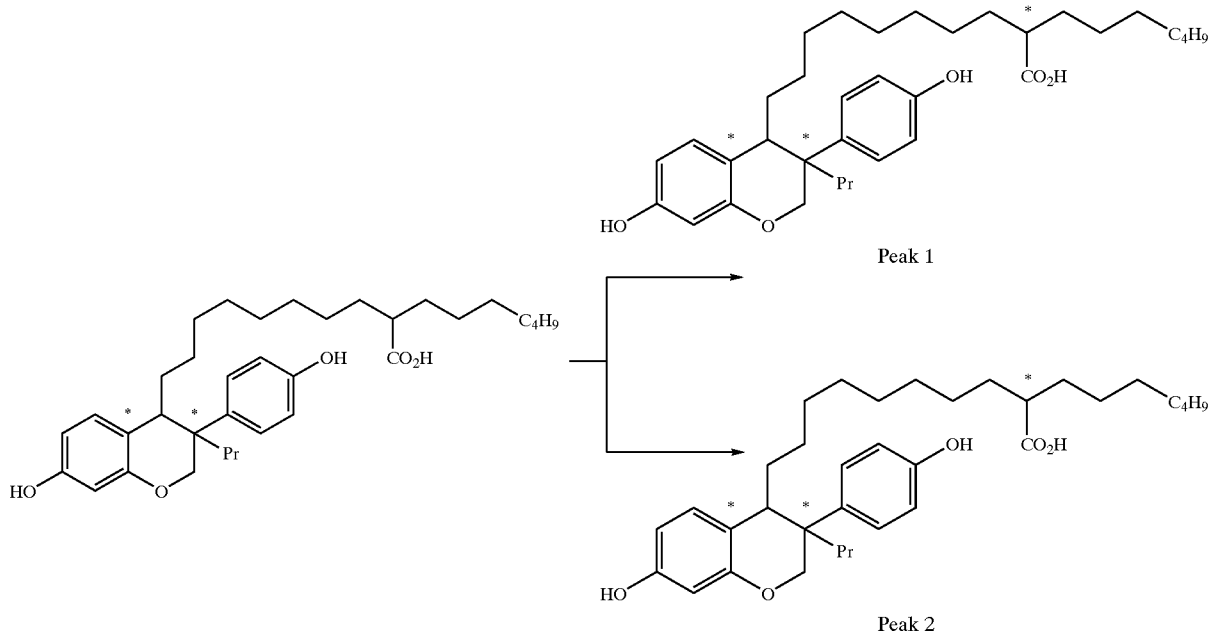

wherein said Peaks 1 and 2 are detected at retention times of 6.9 and 8.3 minutes, respectively, when optically resolved and measured under the following conditions:

Column used: CHIRALPAK AD (0.46 cm ID×25 cm L)
Mobile phase: hexane/isopropanol/acetic acid=80/20/0.1 (v/v/v)
Flow rate: 1.0 ml/min
Column temperature: 40° C.
Detection wavelength: 280 nm.

17. A compound represented by Peak 1 or 2 shown in the following formula:

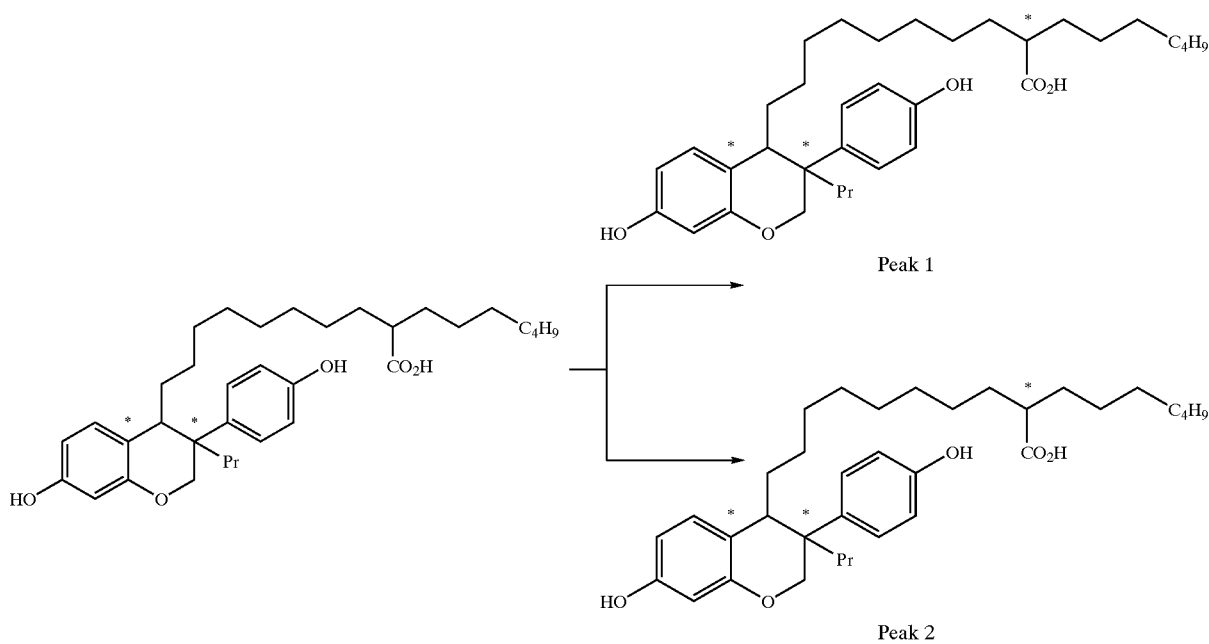

wherein said Peaks 1 and 2 are detected at retention times of 7.1 and 11.9 minutes, respectively, when optically resolved and measured under the following conditions:

Column used: CHIRALCEL OJ (0.46 cm ID×25 cm L)

Mobile phase:hexane/ethanol/acetic acid=90/10/0.1 (v/v/v)

Flow rate: 1.0 ml/min

Column temperature: 40° C.

Detection wavelength: 280 nm.

18. A pharmaceutical composition comprising as an active ingredient, at least one compound according to any one of claims 1 to 15 or enantiomer thereof, or at least one hydrate or pharmaceutically acceptable salt of the compound or its enantiomer.

19. An anti-estrogenic pharmaceutical composition comprising as an active ingredient, at least one compound according to any one of claims 1 to 17 or enantiomer thereof, or at least one hydrate or pharmaceutically acceptable salt of the compound or its enantiomer.

20. A therapeutic agent for breast cancer comprising as an active ingredient, at least one compound according to any one of claims 1 to 17 or enantiomer thereof, or at least one hydrate or pharmaceutically acceptable salt of the compound or its enantiomer.

* * * * *